United States Patent
Yoo et al.

(10) Patent No.: US 12,433,159 B2
(45) Date of Patent: Sep. 30, 2025

(54) ORGANIC COMPOUND, AND ORGANIC LIGHT EMITTING DIODE AND ORGANIC LIGHT EMITTING DEVICE INCLUDING THE SAME

(71) Applicant: LG DISPLAY CO., LTD., Seoul (KR)

(72) Inventors: Seon-Keun Yoo, Paju-si (KR); Dae-Wi Yoon, Paju-si (KR); Shin-Han Kim, Paju-si (KR); Min-Gi Hong, Paju-si (KR); Seong-Su Jeon, Paju-si (KR); Ji-Cheol Shin, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 1006 days.

(21) Appl. No.: 17/407,996

(22) Filed: Aug. 20, 2021

(65) Prior Publication Data

US 2022/0173328 A1    Jun. 2, 2022

(30) Foreign Application Priority Data

Dec. 1, 2020 (KR) .......... 10-2020-0165816

(51) Int. Cl.
| | |
|---|---|
| *H01L 51/54* | (2006.01) |
| *C07D 471/04* | (2006.01) |
| *C09K 11/06* | (2006.01) |
| *H10K 85/60* | (2023.01) |
| *H10K 50/16* | (2023.01) |
| *H10K 50/19* | (2023.01) |

(52) U.S. Cl.
CPC ....... *H10K 85/6572* (2023.02); *C07D 471/04* (2013.01); *C09K 11/06* (2013.01); *H10K 85/615* (2023.02); *H10K 85/654* (2023.02); *H10K 85/657* (2023.02); *C09K 2211/1018* (2013.01); *H10K 50/16* (2023.02); *H10K 50/19* (2023.02)

(58) Field of Classification Search
None
See application file for complete search history.

(56) References Cited

U.S. PATENT DOCUMENTS

| | | | |
|---|---|---|---|
| 2011/0210320 A1* | 9/2011 | Shin ................. | C07D 417/10 257/E51.047 |
| 2016/0043327 A1* | 2/2016 | Yoo .................. | H10K 85/615 257/40 |

FOREIGN PATENT DOCUMENTS

| | | |
|---|---|---|
| CN | 105321984 A | 2/2016 |
| CN | 107207503 A | 9/2017 |

* cited by examiner

*Primary Examiner* — Andrew K Bohaty
(74) *Attorney, Agent, or Firm* — Birch, Stewart, Kolasch & Birch, LLP

(57) ABSTRACT

The present disclosure relates to an organic compound, and an organic light emitting diode and an organic light emitting device including the same, more specifically, relates to an organic compound being represented by following Formula, an organic light emitting diode including the organic compound and an organic light emitting device including the organic light emitting diode. The organic compound is included in an electron transporting layer and/or a p-type charge generation layer of the organic light emitting diode.

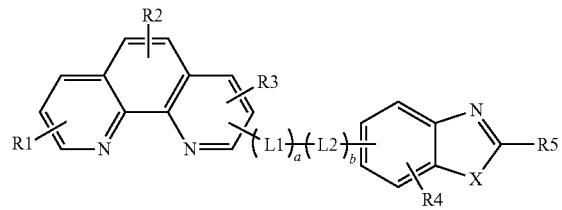

28 Claims, 4 Drawing Sheets

ORGANIC COMPOUND, AND ORGANIC LIGHT EMITTING DIODE AND ORGANIC LIGHT EMITTING DEVICE INCLUDING THE SAME

CROSS-REFERENCE TO RELATED APPLICATIONS

The present application claims the priority benefit of Korean Patent Application No. 10-2020-0165816 filed in the Republic of Korea on Dec. 1, 2020, which is hereby incorporated by reference in its entirety into the present application.

FIELD OF TECHNOLOGY

The present disclosure relates to an organic compound, and more particularly, to an organic compound having improved electron transporting efficiency, and an organic light emitting diode (OLED) and an organic light emitting device including the organic compound.

BACKGROUND OF THE INVENTION

Recently, the requirement for flat panel display devices having small occupied area is increased. Among the flat panel display devices, a technology of an organic light emitting display device, which includes an OLED, is rapidly developed.

The OLED emits light by injecting electrons from a cathode as an electron injection electrode and holes from an anode as a hole injection electrode into an organic emitting layer, combining the electrons with the holes, generating an exciton, and transforming the exciton from an excited state to a ground state. A flexible transparent substrate, for example, a plastic substrate, can be used as a base substrate where elements are formed. In addition, the OLED can be operated at a voltage (e.g., 10V or below) lower than a voltage required to operate other display devices and has low power consumption. Moreover, the light from the OLED has excellent color purity.

To provide sufficient emitting efficiency and lifespan of the OLED, an electron transporting material having sufficient electron transporting efficiency is needed.

SUMMARY OF THE INVENTION

The embodiments of the present disclosure are directed to an organic compound, an OLED and an organic light emitting device that substantially obviate one or more of the problems associated with the limitations and disadvantages of the related conventional art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages in accordance with the purpose of the embodiments of the present disclosure, as described herein, an aspect of the present disclosure provides an organic compound of Formula 1-1:

[Formula 1-1]

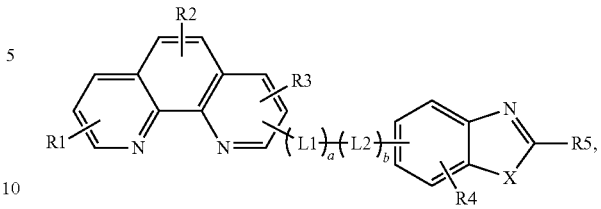

wherein X is oxygen or sulfur, and each of R1 to R5 is independently selected from the group consisting of hydrogen (H), deuterium (D), C1 to C10 alkyl group, C1 to C10 alkoxy group, C3 to C30 cycloalkyl group, C6 to C30 aryl group, C6 to C30 arylamino group and C5 to C30 heteroaryl group unsubstituted or substituted with phenyl, and wherein each of L1 and L2 is independently selected from the group consisting of C6 to C30 arylene group and C5 to C30 heteroarylene group, and each of a and b is 0 or 1.

Another aspect of the present disclosure provides an organic light emitting diode comprising a first electrode; a second electrode facing the first electrode; a first emitting part including a first emitting material layer and a first electron transporting layer and positioned between the first and second electrodes, wherein the first electron transporting layer is positioned between the first emitting material layer and the second electrode and includes a first electron transporting material, wherein the first electron transporting material is the above organic compound.

Another aspect of the present disclosure provides an organic light emitting diode comprising a first electrode; a second electrode facing the first electrode; a first emitting part including a first emitting material layer and positioned between the first and second electrodes; a second emitting part including a second emitting material layer and positioned between the first emitting part and the second electrode; and a first n-type charge generation layer including a first n-type charge generation material and positioned between the first and second emitting parts, wherein the first n-type charge generation material is the above organic compound.

Another aspect of the present disclosure provides an organic light emitting device comprising a substrate; the above organic light emitting diode positioned on the substrate; and an encapsulation film covering the organic light emitting diode.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain the principles of the present disclosure.

DETAILED DESCRIPTION OF THE EMBODIMENTS

Reference will now be made in detail to some of the examples and preferred embodiments, which are illustrated in the accompanying drawings.

In an OLED and an organic light emitting device of the present disclosure, new organic compound is applied to at least one of an electron transporting layer and an n-type charge generation layer. For example, the organic light emitting device can be an organic light emitting display device or an organic lightening device. As an example, an organic light emitting display device, which is a display device including the OLED of the present disclosure, will be mainly described. All the components of each organic light emitting device according to all embodiments of the present disclosure are operatively coupled and configured.

Figure 1:
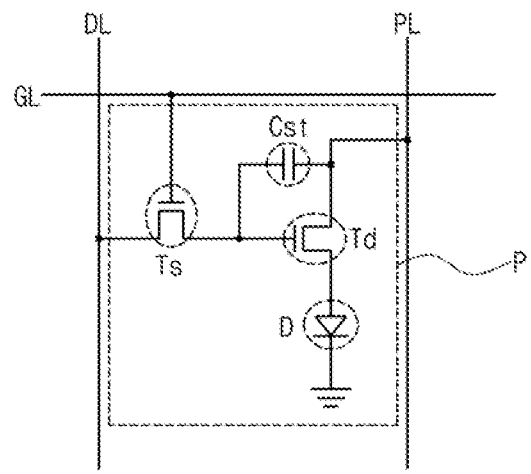
FIG. 1 is a schematic circuit diagram of an organic light emitting display device of the present disclosure.

FIG. 1 is a schematic circuit diagram illustrating an organic light emitting display device of the present disclosure.

As illustrated in FIG. 1, a gate line GL and a data line DL, which cross each other to define a pixel (pixel) P, and a power line PL are formed in an organic light display device. A switching thin film transistor (TFT) Ts, a driving TFT Td, a storage capacitor Cst and an OLED D are formed in the pixel P. The pixel P can include a red pixel, a green pixel and a blue pixel. In addition, the pixel P can further include a white pixel.

The switching thin film transistor Ts is connected to the gate line GL and the data line DL, and the driving thin film transistor Td and the storage capacitor Cst are connected between the switching thin film transistor Ts and the power line PL. The OLED D is connected to the driving thin film transistor Td. When the switching thin film transistor Ts is turned on by the gate signal applied through the gate line GL, the data signal applied through the data line DL is applied a gate electrode of the driving thin film transistor Td and one electrode of the storage capacitor Cst through the switching thin film transistor Ts.

The driving thin film transistor Td is turned on by the data signal applied into the gate electrode so that a current proportional to the data signal is supplied from the power line PL to the OLED D through the driving thin film transistor Tr. The OLED D emits light having a luminance proportional to the current flowing through the driving thin film transistor Td. In this case, the storage capacitor Cst is charge with a voltage proportional to the data signal so that the voltage of the gate electrode in the driving thin film transistor Td is kept constant during one frame. Therefore, the organic light emitting display device can display a desired image.

Figure 2:
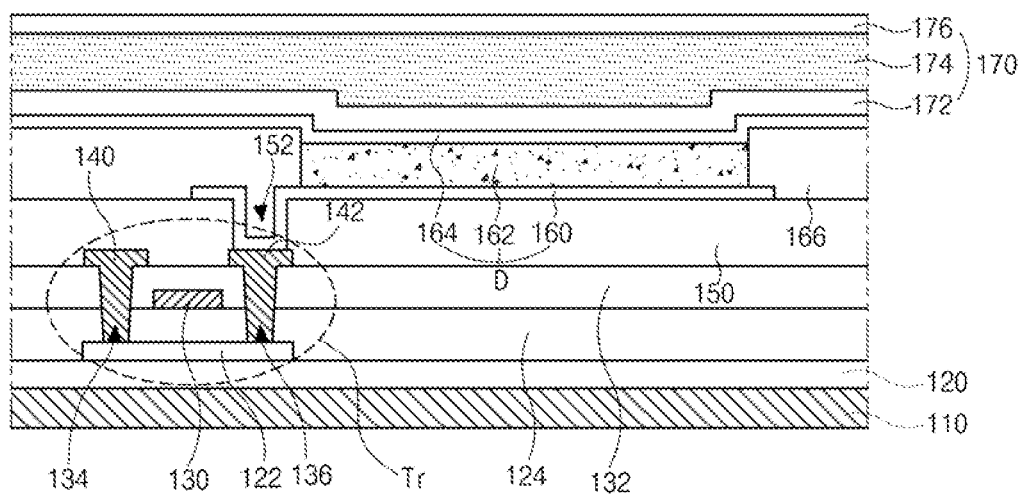
FIG. 2 is a schematic cross-sectional view of an organic light emitting device according to a first embodiment of the present disclosure.

FIG. 2 is a schematic cross-sectional view illustrating an organic light emitting display device according to a first embodiment of the present disclosure.

As illustrated in FIG. 2, the organic light emitting display device 100 includes a substrate 110, a TFT Tr and an OLED D disposed on a planarization layer 150 and connected to the TFT Tr. For example, the organic light emitting display device 100 can include a red pixel, a green pixel and a blue pixel, and the OLED D can be formed in each of the red, green and blue pixels. Namely, the OLEDs D emitting red light, green light and blue light can be provided in the red, green and blue pixels, respectively.

The substrate 110 can be a glass substrate or a flexible substrate. For example, the flexible substrate can be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 120 is formed on the substrate, and the TFT Tr is formed on the buffer layer 120. The buffer layer 120 can be omitted.

A semiconductor layer 122 is formed on the buffer layer 120. The semiconductor layer 122 can include an oxide semiconductor material or polycrystalline silicon.

When the semiconductor layer 122 includes the oxide semiconductor material, a light-shielding pattern can be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities can be doped into both sides of the semiconductor layer 122.

A gate insulating layer 124 is formed on the semiconductor layer 122. The gate insulating layer 124 can be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 2, the gate insulating layer 124 is formed on an entire surface of the substrate 110. Alternatively, the gate insulating layer 124 can be patterned to have the same shape as the gate electrode 130.

An interlayer insulating layer 132, which is formed of an insulating material, is formed on the gate electrode 130. The interlayer insulating layer 132 can be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element. Namely, the TFT Tr can correspond to the driving TFT Td (of FIG. 1).

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode can be positioned under the semiconductor layer, and the source and drain electrodes can be positioned over the semiconductor layer such that the TFT Tr can have an inverted staggered structure. In this instance, the semiconductor layer can include amorphous silicon.

The gate line and the data line cross each other to define the pixel, and the switching TFT is formed to be connected to the gate and data lines. The switching TFT is connected to the TFT Tr as the driving element.

In addition, the power line, which can be formed to be parallel to and spaced apart from one of the gate and data lines, and the storage capacitor for maintaining the voltage of the gate electrode of the TFT Tr in one frame can be further formed.

A planarization layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel and on the planarization layer 150. The first electrode 160 can be an anode and can be formed of a conductive material, e.g., a transparent conductive oxide (TCO), having a relatively high work function. For example, the first electrode 160 can be formed of indium-tin-oxide (ITO), indium-zinc-oxide (IZO), indium-tin-zinc-oxide (ITZO), tin oxide (SnO), zinc oxide (ZnO), indium-copper-oxide (ICO) or aluminum-zinc-oxide (Al:ZnO, AZO).

When the organic light emitting display device 100 is operated in a bottom-emission type, the first electrode 160 can have a single-layered structure of the transparent conductive oxide. When the organic light emitting display device 100 is operated in a top-emission type, a reflection electrode or a reflection layer can be formed under the first electrode 160. For example, the reflection electrode or the reflection layer can be formed of silver (Ag) or aluminum-palladium-copper (APC) alloy. In this instance, the first electrode 160 can have a triple-layered structure of ITO/Ag/ITO or ITO/APC/ITO.

A bank layer 166 is formed on the planarization layer 150 to cover an edge of the first electrode 160. Namely, the bank layer 166 is positioned at a boundary of the pixel and exposes a center of the first electrode 160 in the pixel.

An organic emitting layer 162 is formed on the first electrode 160. The organic emitting layer 162 includes an emitting material layer (EML) and an electron transporting layer (ETL) on (or over) the EML. The organic emitting layer 162 can further include at least one of a hole injection layer (HIL), a hole transporting layer (HTL), an electron blocking layer (EBL), a hole blocking layer (HBL) and an electron injection layer (EIL). As described below, the ETL includes a compound including a benzothiazole moiety or a benzoxazole moiety and a phenanthroline moiety, where the benzothiazole moiety or the benzoxazole moiety is connected (linked, combined or joined) to the phenanthroline moiety directly or through a linker. As a result, the electron is efficiently provided from the ETL into the EML.

The second electrode 164 is formed over the substrate 110 where the organic emitting layer 162 is formed. The second electrode 164 covers an entire surface of the display area and can be formed of a conductive material having a relatively low work function to serve as a cathode. For example, the second electrode 164 can be formed of aluminum (Al), magnesium (Mg), silver (Ag) or their alloy, e.g., Al—Mg alloy (AlMg) or Ag—Mg alloy (MgAg). In the top-emission type organic light emitting display device 100, the second electrode 164 can have a thin profile (small thickness) to provide a light transmittance property (or a semi-transmittance property).

Namely, one of the first and second electrodes 160 and 164 is a transparent (or semi-transparent) electrode, and the other one of the first and second electrodes 160 and 164 is a reflection electrode.

The first electrode 160, the organic emitting layer 162 and the second electrode 164 constitute the OLED D.

An encapsulation film 170 is formed on the second electrode 164 to prevent penetration of moisture into the OLED D. The encapsulation film 170 includes a first inorganic insulating layer 172, an organic insulating layer 174 and a second inorganic insulating layer 176 sequentially stacked, but it is not limited thereto. The encapsulation film 170 can be omitted.

The organic light emitting display device 100 can further include a color filter layer. The color filter layer can include a red color filter, a green color filter and a blue color filter respectively corresponding to the red pixel, the green pixel and the blue pixel. The color purity of the organic light emitting display device 100 can be improved by the color filter layer.

The organic light emitting display device 100 can further include a polarization plate for reducing an ambient light reflection. For example, the polarization plate can be a circular polarization plate. In the bottom-emission type organic light emitting display device 100, the polarization plate can be disposed under the substrate 110. In the top-emission type organic light emitting display device 100, the polarization plate can be disposed on or over the encapsulation film 170.

In addition, in the top-emission type organic light emitting display device 100, a cover window can be attached to the encapsulation film 170 or the polarization plate. In this instance, the substrate 110 and the cover window have a flexible property such that a flexible organic light emitting display device can be provided.

Figure 3:
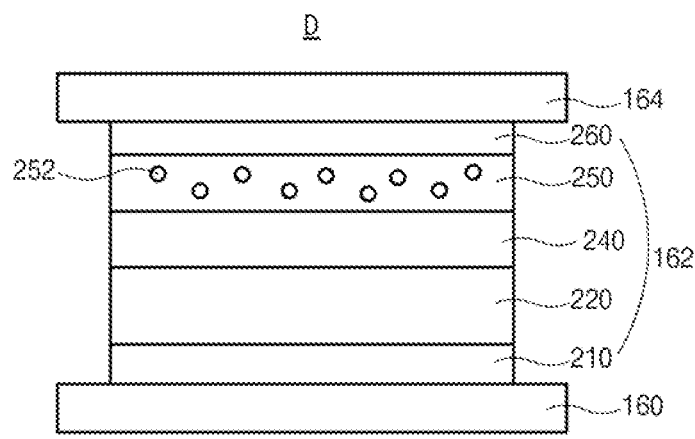
FIG. 3 is a schematic cross-sectional view of an OLED according to a second embodiment of the present disclosure.

FIG. 3 is a schematic cross-sectional view illustrating an OLED according to a second embodiment.

As shown in FIG. 3, the OLED D includes the first and second electrodes 160 and 164 facing each other and the organic emitting layer 162 between the first and second electrodes 160 and 164. The organic emitting layer 162 includes an EML 240 between the first and second electrodes 160 and 164 and an ETL 250 between the second electrode 164 and the EML 240.

The first electrode 160 is an anode, and the second electrode 164 is a cathode. One of the first and second electrodes 160 and 164 is a transparent electrode (or a semi-transparent electrode), and the other one of the first and second electrodes 160 and 164 is a reflection electrode.

The organic emitting layer 162 can further include an HTL 220 between the first electrode 160 and the EML 240.

In addition, the organic emitting layer 162 can further include at least one of an HIL 210 between the first electrode 160 and the HTL 220 and an EIL 260 between the second electrode 164 and the ETL 250.

The organic emitting layer 162 can further include at least one of an EBL between the HTL 220 and the EML 240 and an HBL between the ETL 250 and the EML 240.

For example, the HIL 210 can include at least one compound selected from the group consisting of 4,4',4"-tris (3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (1T-NATA), 4,4',4"-tris(N-(naphthalene-2-yl)-N-phenyl-amino)triphenylamine (2T-NATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPB or NPD), 1,4,5,8,9,11-hexaazatriphenylenehexacarbonitrile(dipyrazino[2,3-f:2'3'-h]quinoxaline-2,3,6,7,10,11-hexacarbonitrile (HAT-CN), 1,3,5-tris[4-(diphenylamino) phenyl]benzene (TDAPB), poly(3,4-ethylenedioxythiphene)polystyrene sulfonate (PEDOT/PSS) and N-(biphenyl-4-yl)-9,9-dimethyl-N-(4-(9-phenyl-9H-carbazol-3-yl)phenyl)-9H-fluoren-2-amine, but it is not limited thereto.

The HTL220 can include at least one compound selected from the group consisting of N,N'-diphenyl-N,N'-bis(3-methylphenyl)-1,1'-biphenyl-4,4'-diamine (TPD), NPB (or NPD), 4,4'-bis(N-carbazolyl)-1,1'-biphenyl (CBP), poly[N, N'-bis(4-butylpnehyl)-N,N'-bis(phenyl)-benzidine](poly-TPD), (poly[(9,9-dioctylfluorenyl-2,7-diyl)-co-(4,4'-(N-(4-sec-buty 1phenyl)diphenylamine))](TFB), di-[4-(N,N-di-p-tolyl-amino)-phenyl]cyclohexane (TAPC), 3,5-di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, and N-(biphenyl-4-yl)-N-(4-(9-phenyl-9H-carbazol-3-yl)phenyl)biphenyl-4-amine, but it is not limited thereto.

The EBL can include at least one compound selected from the group consisting of TCTA, tris[4-(diethylamino)phenyl] amine, N-(biphenyl-4-yl)-9,9-dimethyl-N-(4-(9-phenyl-9H-carbazol-3-yl)phenyl)-9H-fluoren-2-amine, TAPC, MTDATA, 1,3-bis(carbazol-9-yl)benzene (mCP), 3,3'-bis (N-carbazolyl)-1,1'-biphenyl(mCBP), CuPc, N,N'-bis[4-[bis (3-methylphenyl)amino]phenyl]-N,N'-diphenyl-[1,1'-biphenyl]-4,4'-diamine (DNTPD), TDAPB, DCDPA, and 2,8-bis (9-phenyl-9H-carbazol-3-yl)dibenzo[b,d]thiophene, but it is not limited thereto.

The HBL can include at least one compound selected from the group consisting of tris-(8-hydroxyquinoline aluminum (Alq$_3$), 2-biphenyl-4-yl-5-(4-t-butylphenyl)-1,3,4-oxadiazole (PBD), spiro-PBD, lithium quinolate (Liq), 2,2', 2"-(1,3,5-benzinetriyl)-tris(1-phenyl-1-H benzimidazole) (TPBi), bis(2-methyl-8-quinolinolato-N1,O8)-(1,1'-biphenyl-4-olato)aluminum (BAlq), 4,7-diphenyl-1,10-phenanthroline (Bphen), 2,9-bis(naphthalene-2-yl)4,7-diphenyl-1,10-phenanthroline (NBphen), 2,9-dimethyl-4,7-diphenyl-1,10-phenathroline (BCP), 3-(4-biphenyl)-4-phenyl-5-tert-butylphenyl-1,2,4-triazole (TAZ), 4-(naphthalen-1-yl)-3,5-diphenyl-4H-1,2,4-triazole (NTAZ), 1,3,5-trip-pyrid-3-yl-phenyl)benzene (TpPyPB), 2,4,6-tris(3'-(pyridin-3-yl)biphenyl-3-yl)1,3,5-triazine (TmPPPyTz), Poly[9,9-bis(3'-((N,N-dimethyl)-N-ethylammonium)-propyl)-2,7-fluorene]-alt-2,7-(9,9-dioctylfluorene)](PFNBr), tris(phenylquinoxaline (TPQ), and diphenyl-4-triphenylsilyl-phenylphosphine oxide (TSPO1), but it is not limited thereto.

The EIL 260 can include at least one of an alkali metal, such as Li, an alkali halide compound, such as LiF, CsF, NaF, or BaF$_2$, and an organo-metallic compound, such as Liq, lithium benzoate, or sodium stearate, but it is not limited thereto.

The EML 240 in the red pixel includes a host and a red dopant, the EML 240 in the green pixel includes a host and a green dopant, and the EML 240 in the blue pixel includes a host and a blue dopant. Each of the red dopant, the green dopant and the blue dopant can be one of a fluorescent compound, a phosphorescent compound and a delayed fluorescent compound.

For example, in the EML 240 of the red pixel, the host can be 4,4'-bis(carbazol-9-yl)biphenyl (CBP), and the red dopant can be selected from the group consisting of bis(1-phenylisoquinoline)acetylacetonate iridium (PIQIr(acac)), bis(1-phenylquinoline)acetylacetonate iridium (PQIr(acac)), tris(1-phenylquinoline)iridium (PQIr), and octaethylporphyrin platinum (PtOEP). The EML 240 in the red pixel can provide the light having a wavelength range (e.g., an emission wavelength range) of about 600 to 650 nm.

In the EML 240 of the green pixel, the host can be CBP, and the green dopant can be fac-tris(2-phenylpyridine) iridium (Ir(ppy)$_3$) or tris(8-hydroxyquinolino)aluminum (Alq$_3$). The EML 240 in the green pixel can provide the light having a wavelength range of about 510 to 570 nm.

In the EML 240 of the blue pixel, the host can be an anthracene derivative, and the blue dopant can be a pyrene derivative. For example, the host can be a compound in Formula 5, and the blue dopant can be a compound in Formula 6. In the EML 240 of the blue pixel, the blue dopant can have a weight % of 1 to 20, preferably 1 to 10. The EML 240 in the blue pixel can provide the light having a wavelength range of about 440 to 480 nm.

The ETL 250 includes an organic compound of the present disclosure as an electron transporting material 252. Namely, the organic compound including a benzothiazole moiety or a benzoxazole moiety and a phenanthroline moiety, where the benzothiazole moiety or the benzoxazole moiety is connected (linked, combined or joined) to the phenanthroline moiety directly or through a linker, is included in the ETL 250. The organic compound of the present disclosure is represented by Formula 1-1.

[Formula 1-1]

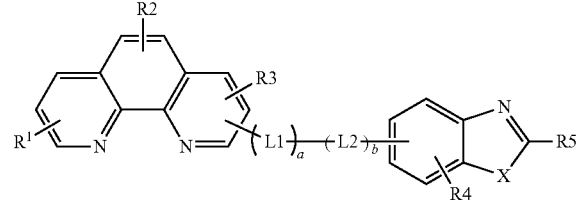

In Formula 1-1, X is oxygen (O) or sulfur (S), and each of R1 to R5 is independently selected from the group consisting of hydrogen (H), deuterium (D), C1 to C10 alkyl group, C1 to C10 alkoxy group, C3 to C30 cycloalkyl group, C6 to C30 aryl group, C6 to C30 arylamino group and C5 to C30 heteroaryl group unsubstituted or substituted with phenyl. Each of L1 and L2 is independently selected from the group consisting of C6 to C30 arylene group and C5 to C30 heteroarylene group, and each of a and b is 0 or 1.

For example, C6 to C30 aryl can be selected from the group consisting of phenyl, biphenyl, terphenyl, naphthyl, anthracenyl, pentanenyl, indenyl, indenoindenyl, heptalenyl, biphenylenyl, indacenyl, phenanthrenyl, benzophenanthrenyl, dibenzophenanthrenyl, azulenyl, pyrenyl, fluoranthenyl, triphenylenyl, chrysenyl, tetraphenyl, tetrasenyl, picenyl, pentaphenyl, pentacenyl, fluorenyl, indenofluorenyl and spiro-fluorenyl. Except for being a divalent group, C6 to C30 arylene is the same as the above C6 to C30 aryl.

For example, C5 to C30 heteroaryl (or heteroaryele) can be selected from the group consisting of pyrrolyl, pyridinyl, pyrimidinyl, pyrazinyl, pyridazinyl, triazinyl, tetrazinyl, imidazolyl, pyrazolyl, indolyl, isoindolyl, indazolyl, indolizinyl, pyrrolizinyl, carbazolyl, benzocarbazolyl, dibenzocarbazolyl, indolocarbazolyl, indenocarbazolyl, benzofurocarbazolyl, benzothienocarbazolyl, quinolinyl, isoquinolinyl, phthalazinyl, quinoxalinyl, cinnolinyl, quinazolinyl, quinolinyl, purinyl, phthalazinyl, quinoxalinyl, benzoquinolinyl, benzoisoquinolinyl, benzoquinazolinyl, benzoquinoxalinyl, acridinyl, phenanthrolinyl, perimidinyl, phenanthridinyl, pteridinyl, cinnolinyl, naphtharidinyl, furanyl, oxazinyl, oxazolyl, oxadiazolyl, triazolyl, dioxynyl, benzofuranyl, dibenzofuranyl, thiopyranyl, xantenyl, chromanyl,isochromanyl, thioazinyl, thiophenyl, benzothiophenyl, dibenzothiophenyl, difuropyrazinyl, benzofurodibenzofuranyl, benzothienobenzothiophenyl, benzothienodibenzothiophenyl, benzothienobenzofuranyl, and benzothienodibenzofuranyl. Except for being a divalent group, C5 to C30 heteroaryele is the same as the above C5 to C30 heteroaryl.

In Formula 1-1, C1 to C10 alkyl group, C1 to C10 alkoxy group, C3 to C30 cycloalkyl group, C6 to C30 aryl group, C6 to C30 arylamino group, C5 to C30 heteroaryl group, C6 to C30 arylene group and C5 to C30 heteroarylene group can be unsubstituted or substituted with D and/or phenyl.

For example, each of R1 and R4 can be independently H or D, and each of L1 and L2 can be independently selected from phenylene, naphthylene and anthracenylene. At least one of a and b can be 1, and R5 can be selected from phenyl, naphthyl, quinolinyl, pyridyl, diphenylpyridyl and quinoxalinyl.

In an exemplary embodiment of the present disclosure, each of R1 and R4 can be H, each of L1 and L2 can be independently selected from phenylene, naphthylene and anthracenylene, and R5 can be phenyl. In further exemplary embodiment of the present disclosure, each of R1 and R4 can be H, each of L1 and L2 can be naphthylene, and R5 can be phenyl. (a=1 and b=0)

The organic compound of the present disclosure has a structure including the benzothiazole moiety or the benzoxazole moiety and the phenanthroline moiety, and the benzothiazole moiety or the benzoxazole moiety is connected (linked, combined or joined) to the phenanthroline moiety directly or through a linker, e.g., L1 and/or L2. As a result, the organic compound has high electron transporting efficiency (property). For example, in the organic compound of the present disclosure, the benzothiazole moiety or the benzoxazole moiety is connected (linked, combined or joined) to a second position of the phenanthroline moiety directly or through the linker. The organic compound of the present disclosure can be represented by Formula 1-2.

[Formula 1-2]

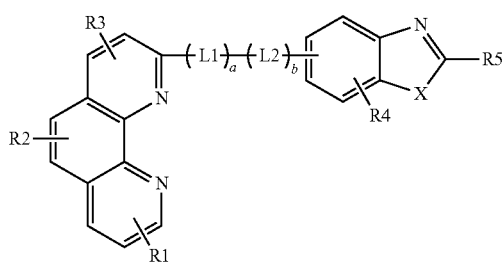

For example, the organic compound of the present disclosure is one of the compounds in Formula 2.

[Formula 2]

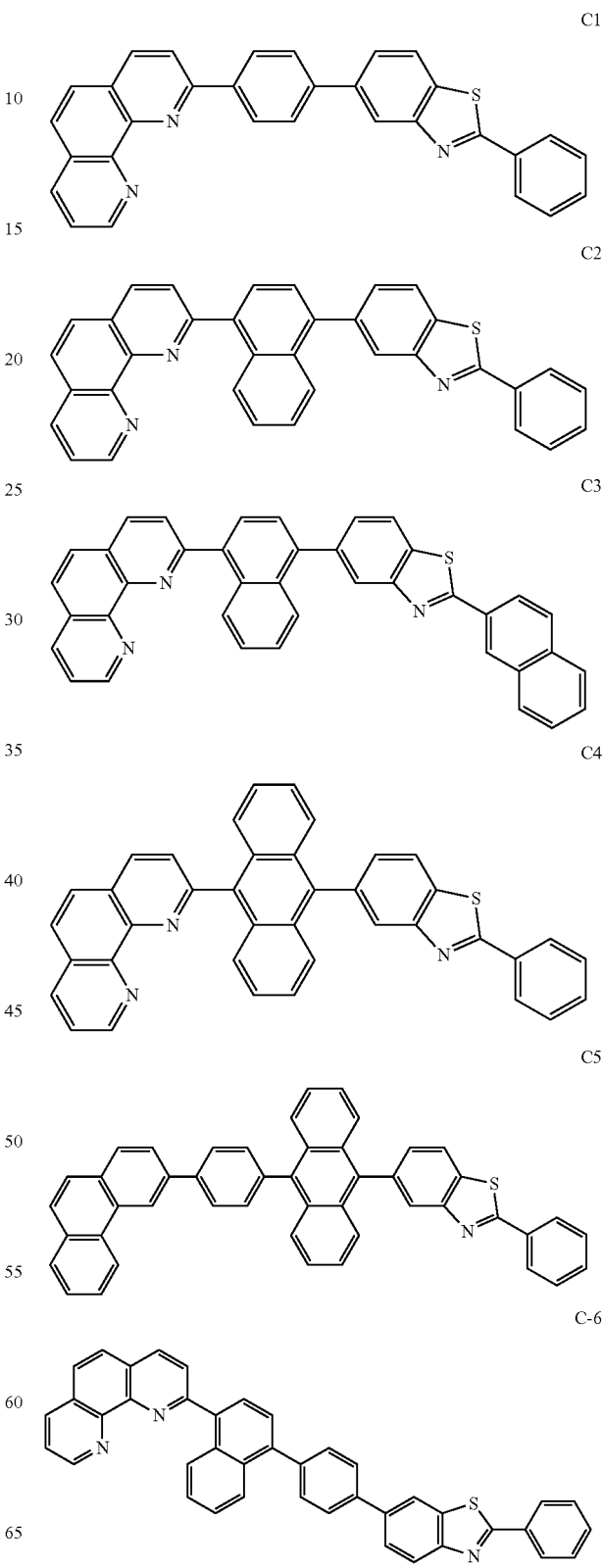

-continued
C7
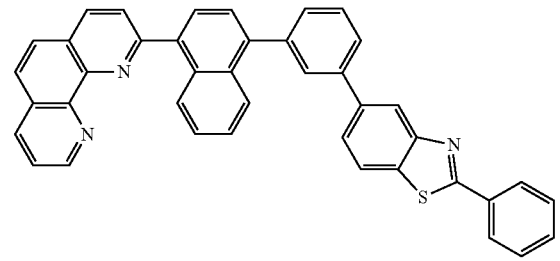
C8
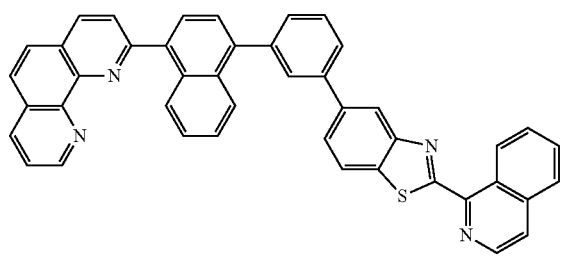
C9
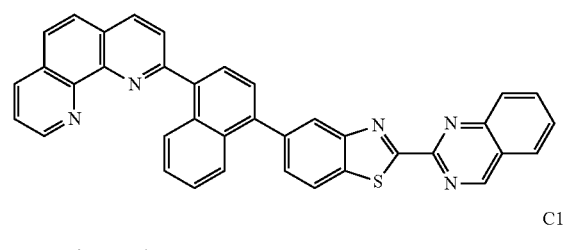
C10
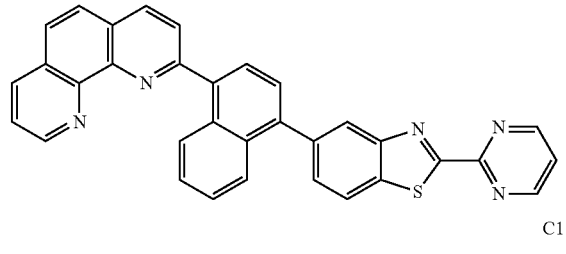
C11
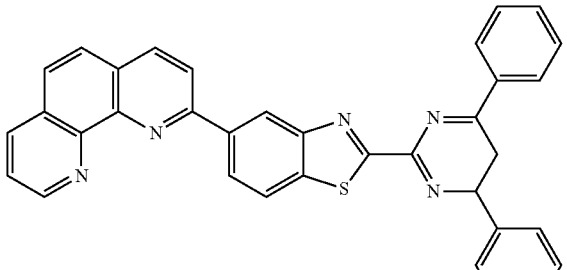
C12
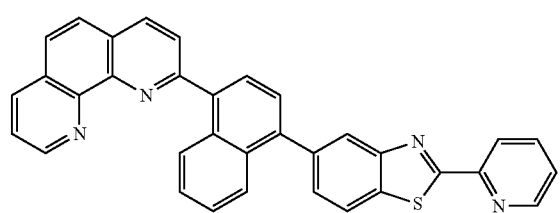
-continued
C13
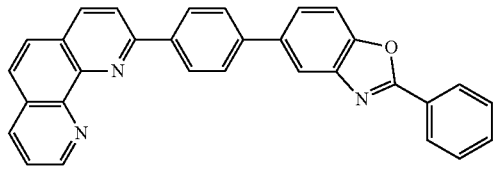
C14
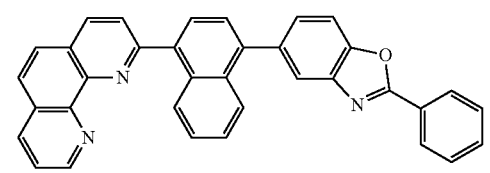
C15
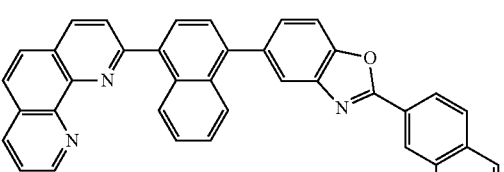
C16
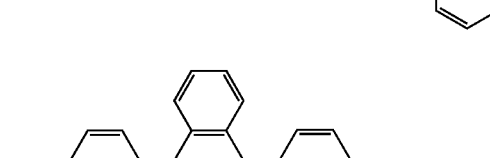
C17
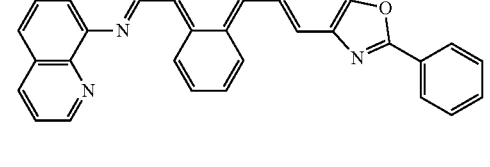
C18
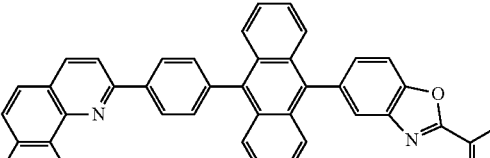
C19
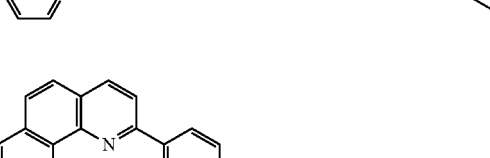

14

Synthesis

1. Synthesis of the Compound C2

(1) Compound A

[Reaction Formula 1-1]

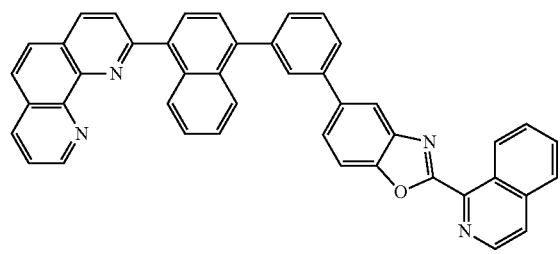

In a round-bottom flask, 1-(1-bromonaphthalen-4-yl)ethanone (29 g, 0.058 mol), 8-aminoquinoline-7-carbaldehyde (20 g, 0.058 mol), absolute ethanol (EtOH, 800 ml), and potassium hydroxide (KOH, 13 g) were added. The temperature of the mixture was raised to reflux and stirred for 15 hours. After cooling the reaction solution to room temperature, the organic layer was recovered by extraction with methylene dichloride (MC) and water. After the organic layer was concentrated under reduced pressure and was recrystallized using ethyl acetate (EA) to obtain the compound A (23 g).

(2) Compound C2

[Reaction Formula 1-2]

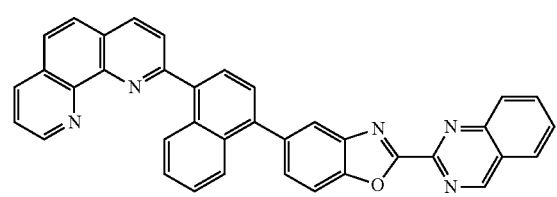

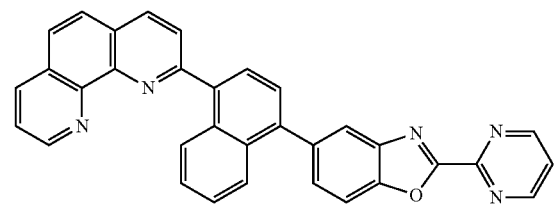

-continued

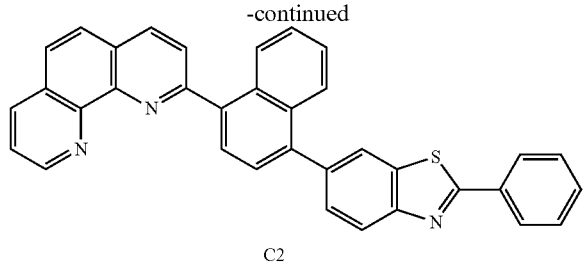

C2

In a round-bottom flask, the compound A (5 g, 13 mmol), 6-(4,4,5,5-tetramethyl-1,3,2-dioxaborolan-2-yl)-2-phenylbenzo[d]thiazole (5.5 g, 16 mmol), tetrakis(triphenylphosphine) palladium(0) (0.6 g, 0.05 mmol), toluene (100 ml), EtOH (30 ml), and 4M $K_2CO_3$ (potassium carbonate, 15 ml) were added and stirred/refluxed for 12 hours. After completion of the reaction, the reaction solution was filtered to obtain a crude product. The crude product was recrystallized using a solvent of $CHCl_3$ (chloroform) to obtain the compound C2 (5.3 g).

2. Synthesis of the Compound C4

[Reaction Formula 2]

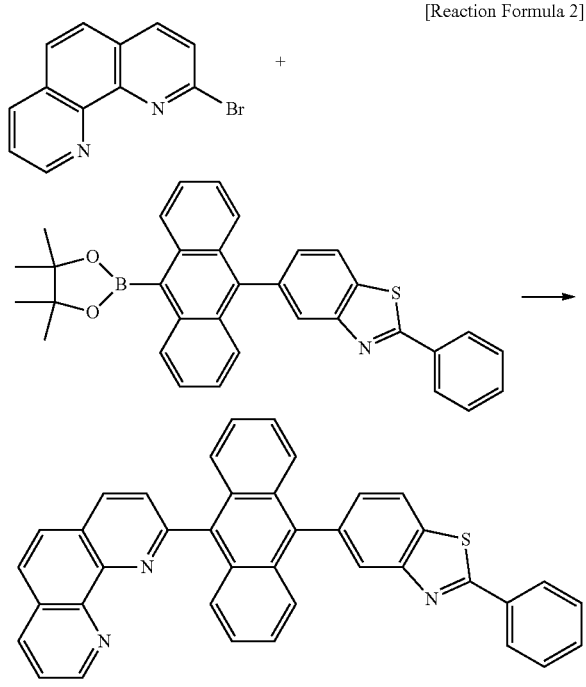

C4

In a round-bottom flask, 2-bromophenanthroline (5 g, 19 mmol), 5-(10-(4,4,5,5-tetramethyl-1,3,2-dioxaborolan-2-yl)anthracen-9-yl)-2-phenylbenzo[d]thiazole (11.9 g, 36 mmol), tetrakis(triphenylphosphine) palladium(0) (0.9 g, 0.08 mmol), toluene (100 ml), EtOH (30 ml), and 4M $K_2CO_3$ (15 ml) were added and stirred/refluxed for 12 hours. After completion of the reaction, the reaction solution was filtered to obtain a crude product. The crude product was recrystallized using a solvent of CHCl to obtain the compound C4 (7.8 g).

3. Synthesis of the Compound C6

[Reaction Formula 3]

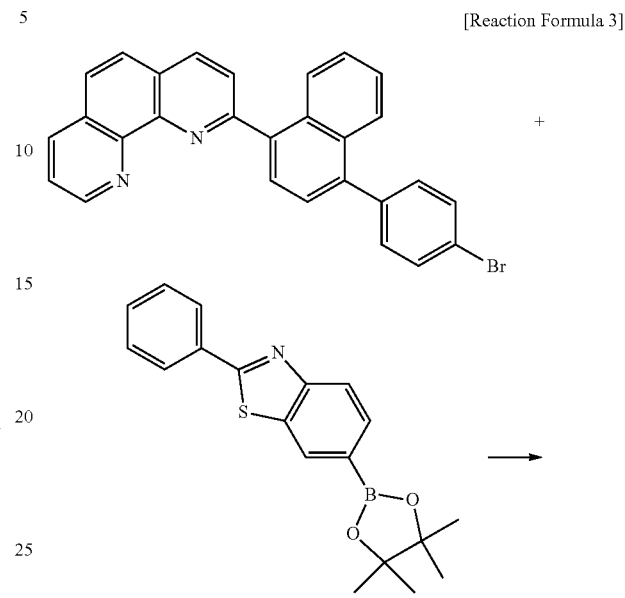

C6

In a round-bottom flask, 2-(1-(4-bromophenyl) naphthalen-4-yl)-1,10-phenanthroline (5 g, 11 mmol), 6-(4,4,5,5-tetramethyl-1,3,2-dioxaborolan-2-yl)-2-phenylbenzo[d]thiazole (5.1 g, 15 mmol), tetrakis(triphenylphosphine) palladium(0) (0.5 g, 0.04 mmol), toluene (100 ml), EtOH (25 ml), and 4M $K_2CO_3$ (15 ml) were added and stirred/refluxed for 12 hours. After completion of the reaction, the reaction solution was filtered to obtain a crude product. The crude product was recrystallized using a solvent of $CHCl_3$ to obtain the compound C6 (4.8 g).

4. Synthesis of the Compound C8

[Reaction Formula 4]

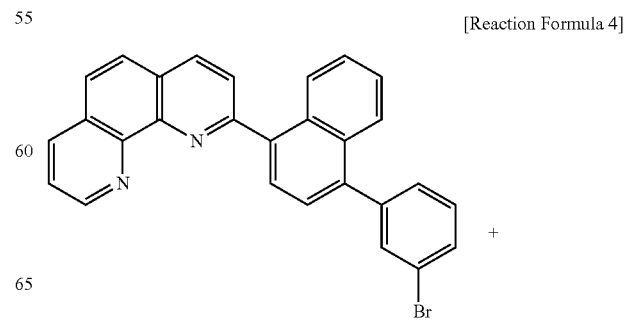

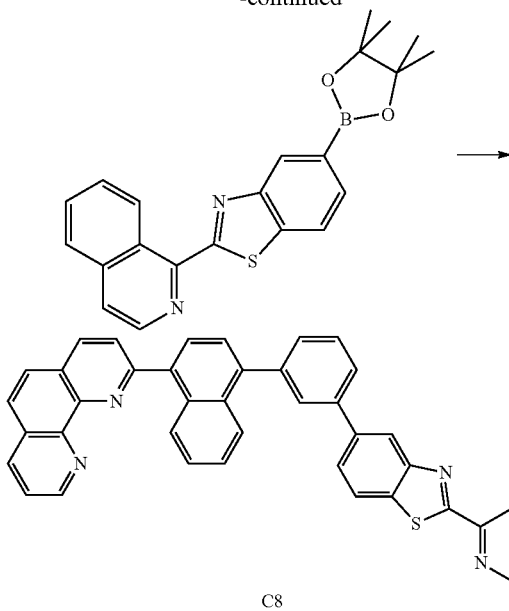

C8

In a round-bottom flask, 2-(1-(3-bromophenyl) naphthalen-4-yl)-1,10-phenanthroline (5 g, 11 mmol), 1-(5-(4,4,5,5-tetramethyl-1,3,2-dioxaborolan-2-yl) benzo[d]thiazol-2-yl) isoquinoline (5.9 g, 14 mmol), tetrakis (triphenylphosphine) palladium(0) (0.5 g, 0.04 mmol), toluene (100 ml), EtOH (30 ml), and 4M K$_2$CO$_3$ (15 ml) were added and stirred/refluxed for 12 hours. After completion of the reaction, the reaction solution was filtered to obtain a crude product. The crude product was recrystallized using a solvent of CHCl$_3$ to obtain the compound C8 (5.3 g).

5. Synthesis of the Compound C10

[Reaction Formula 5]

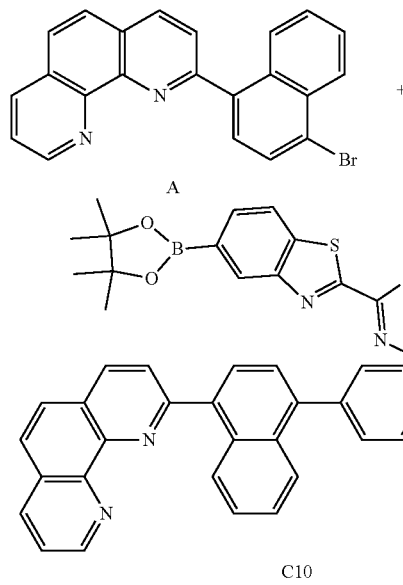

C10

In a round-bottom flask, the compound A (5 g, 13 mmol), 5-(4,4,5,5-tetramethyl-1,3,2-dioxaborolan-2-yl)-2-(pyrimidin-2-yl)benzo[d]thiazol (6.2 g, 18 mmol), tetrakis(triphenylphosphine)palladium(0) (0.6 g, 0.05 mmol), toluene (100 ml), EtOH (30 ml), and 4M K$_2$CO$_3$ (15 ml) were added and stirred/refluxed for 12 hours. After completion of the reaction, the reaction solution was filtered to obtain a crude product. The crude product was recrystallized using a solvent of CHCl to obtain the compound C10 (5.3 g).

6. Synthesis of the Compound C14

[Reaction Formula 6]

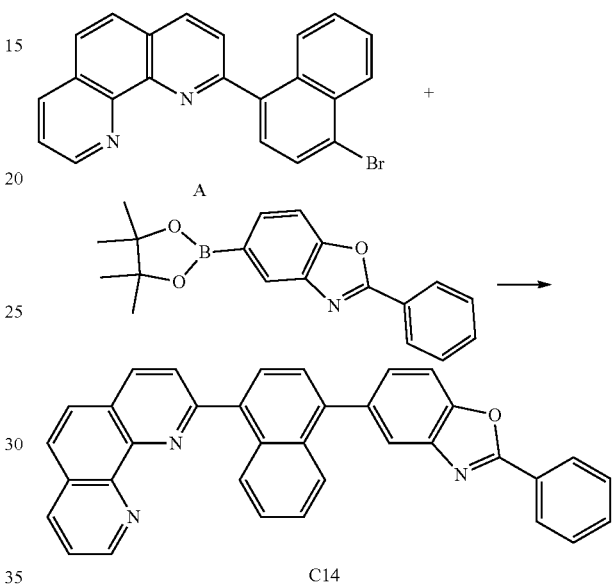

C14

In a round-bottom flask, the compound A (5 g, 13 mmol), 5-(4,4,5,5-tetramethyl-1,3,2-dioxaborolan-2-yl)-2-phenyl-benzo[d]oxazole (5.0 g, 16 mmol), tetrakis(triphenylphosphine) palladium(0) (0.6 g, 0.05 mmol), toluene (100 ml), EtOH (30 ml), and 4M K$_2$CO$_3$ (15 ml) were added and stirred/refluxed for 12 hours. After completion of the reaction, the reaction solution was filtered to obtain a crude product. The crude product was recrystallized using a solvent of CHCl$_3$ to obtain the compound C14 (4.6 g).

7. Synthesis of the Compound C16

[Reaction Formula 7]

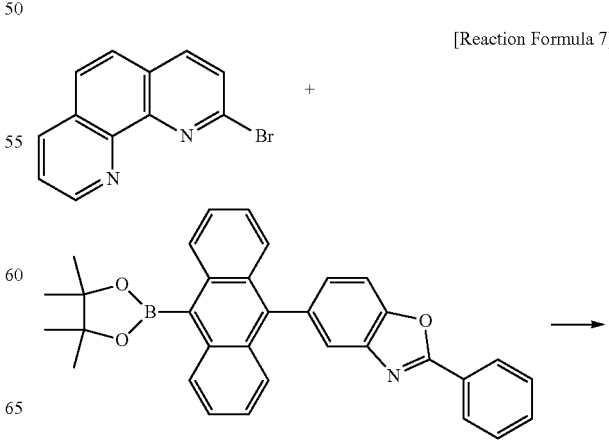

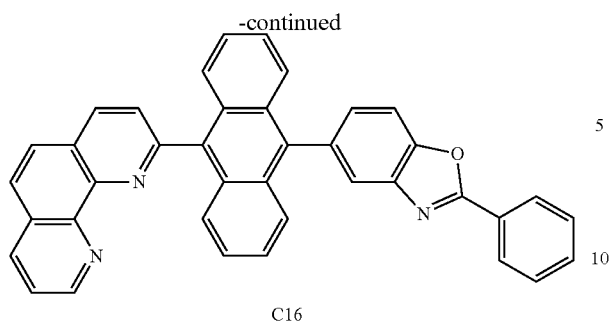

C16

In a round-bottom flask, 2-bromophenanthroline (5 g, 19 mmol), 5-(10-(4,4,5,5-tetramethyl-1,3,2-dioxaborolan-2-yl)anthracen-9-yl)-2-phenylbenzo[d]oxazole (13.4 g, 36 mmol), tetrakis(triphenylphosphine)palladium(0) (0.9 g, 0.08 mmol), toluene (100 ml), EtOH (30 ml), and 4M K₂CO₃ (15 ml) were added and stirred/refluxed for 12 hours. After completion of the reaction, the reaction solution was filtered to obtain a crude product. The crude product was recrystallized using a solvent of CHCl₃ to obtain the compound C16 (7.8 g).

8. Synthesis of the Compound C18

[Reaction Formula 8]

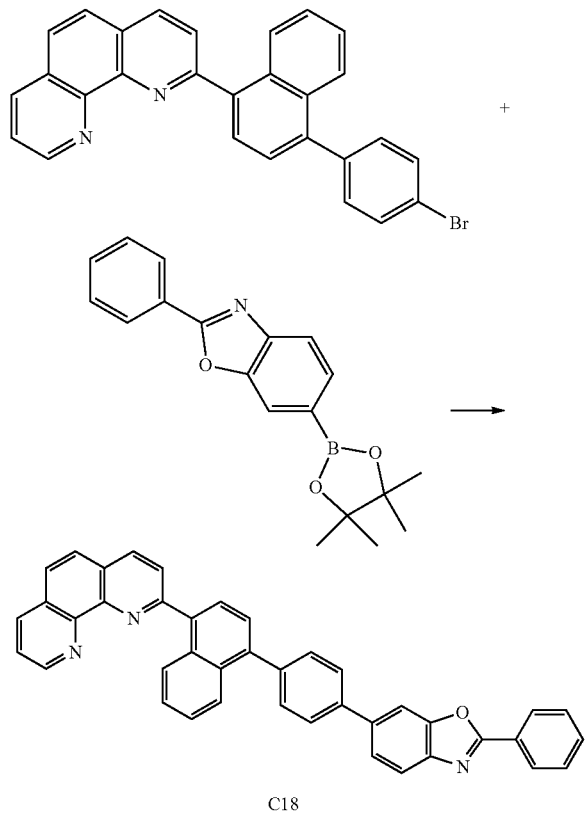

C18

In a round-bottom flask, 2-(1-(4-bromophenyl) naphthalen-4-yl)-1,10-phenanthroline (5 g, 11 mmol), 6-(4,4,5,5-tetramethyl-1,3,2-dioxaborolan-2-yl)-2-phenylbenzo[d]oxazole (4.9 g, 15 mmol), tetrakis(triphenylphosphine)palladium(0) (0.5 g, 0.04 mmol), toluene (100 ml), EtOH (25 ml), and 4M K₂CO₃ (15 ml) were added and stirred/refluxed for 12 hours. After completion of the reaction, the reaction solution was filtered to obtain a crude product. The crude product was recrystallized using a solvent of CHCl to obtain the compound C18 (4.7 g).

9. Synthesis of the Compound C20

[Reaction Formula 9]

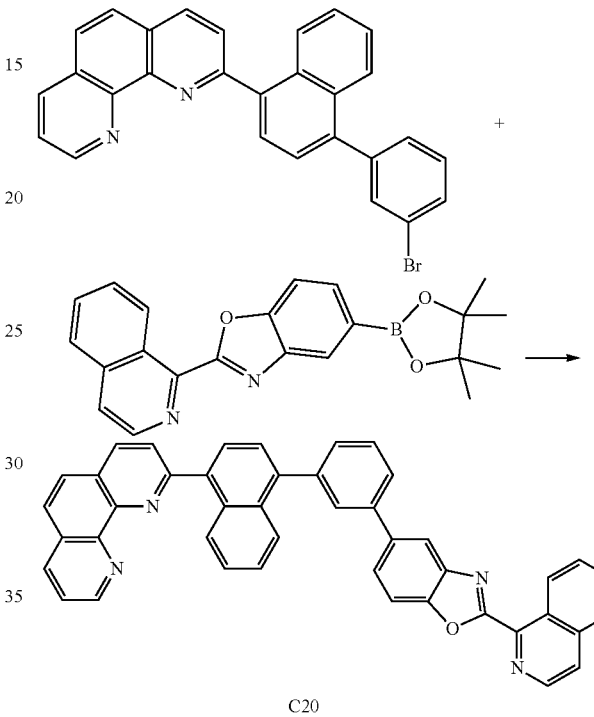

C20

In a round-bottom flask, 2-(1-(3-bromophenyl) naphthalen-4-yl)-1,10-phenanthroline (5 g, 11 mmol), 1-(5-(4,4,5,5-tetramethyl-1,3,2-dioxaborolan-2-yl)benzo[d]oxazol-2-yl) isoquinoline (5.6 g, 14 mmol), tetrakis(triphenylphosphine)palladium(0) (0.5 g, 0.04 mmol), toluene (100 ml), EtOH (30 ml), and 4M K₂CO₃ (15 ml) were added and stirred/refluxed for 12 hours. After completion of the reaction, the reaction solution was filtered to obtain a crude product. The crude product was recrystallized using a solvent of CHCl₃ to obtain the compound C20 (4.7 g).

10. Synthesis of the Compound C22

[Reaction Formula 10]

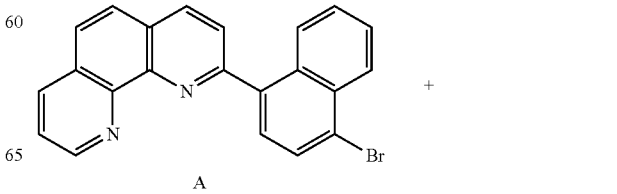

A

-continued

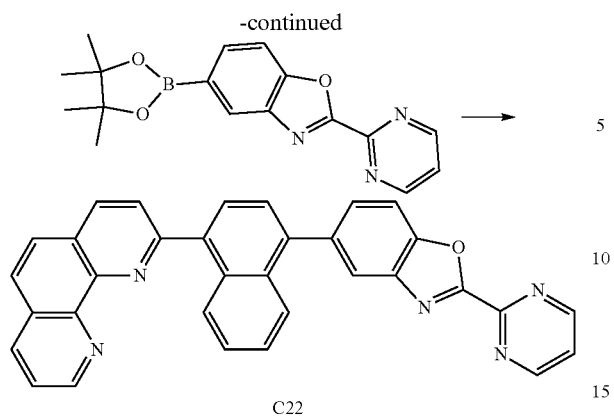

C22

In a round-bottom flask, the compound A (5 g, 13 mmol), 5-(4,4,5,5-tetramethyl-1,3,2-dioxaborolan-2-yl)-2-(pyrimidin-2-yl(benzo[d]oxazole (5.9 g, 18 mmol), tetrakis(triphenylphosphine)palladium(0) (0.6 g, 0.05 mmol), toluene (100 ml), EtOH (30 ml), and 4M K$_2$CO$_3$ (15 ml) were added and stirred/refluxed for 12 hours. After completion of the reaction, the reaction solution was filtered to obtain a crude product. The crude product was recrystallized using a solvent of CHCl$_3$ to obtain the compound C22 (4.1 g).

Since in the OLED D of the present disclosure, the ETL 250 includes the electron transporting material 252 being the organic compound of the present disclosure, the electron transporting property from the second electrode 164 being the cathode into the EML 240 is improved. Accordingly, in the OLED D and the organic light emitting display device 100, the driving voltage is decreased, and the emitting efficiency and the lifespan are increased.

[OLED]

On the anode (ITO), the HIL (100 Å, the compound in Formula 3), the HTL (1000 Å, the compound in Formula 4), the EML (250 Å, the host (the compound in Formula 5) and the dopant (the compound in Formula 6, 3 wt %)), the ETL (300 Å), the EIL (LiF, 20 Å) and the cathode (Al) were sequentially deposited to form the OLED.

1. Comparative Examples
(1) Comparative Example 1 (Ref1)
The ETL is formed using the compound in Formula 7.
(2) Comparative Example 2 (Ref2)
The ETL is formed using the compound in Formula 8.
2. Examples
(1) Example 1 (Ex1)
The ETL is formed using the compound C2 in Formula 2.
(2) Example 2 (Ex2)
The ETL is formed using the compound C4 in Formula 2.
(3) Example 3 (Ex3)
The ETL is formed using the compound C6 in Formula 2.
(4) Example 4 (Ex4)
The ETL is formed using the compound C8 in Formula 2.
(5) Example 5 (Ex5)
The ETL is formed using the compound C10 in Formula 2.
(6) Example 6 (Ex6)
The ETL is formed using the compound C14 in Formula 2.
(7) Example 7 (Ex7)
The ETL is formed using the compound C16 in Formula 2.
(8) Example 8 (Ex8)
The ETL is formed using the compound C18 in Formula 2.
(9) Example 9 (Ex9)
The ETL is formed using the compound C20 in Formula 2.
(10) Example 10 (Ex10)
The ETL is formed using the compound C22 in Formula 2.

[Formula 3]

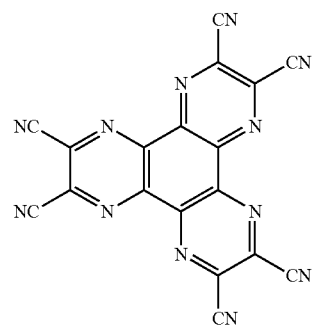

[Formula 4]

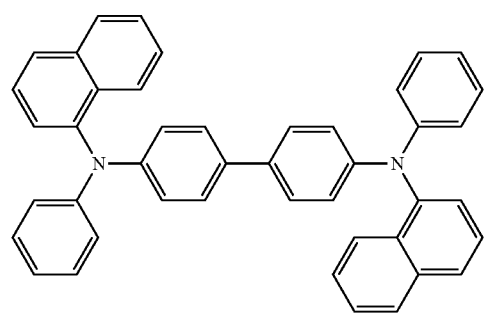

[Formula 5]

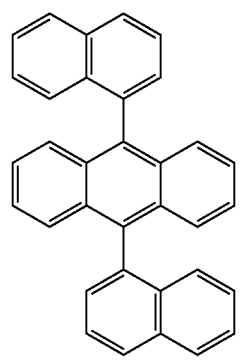

[Formula 6]

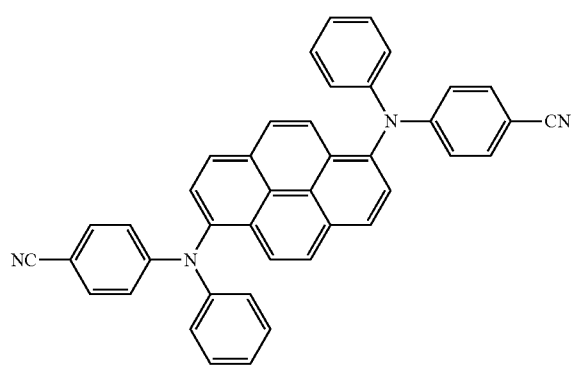

[Formula 7]

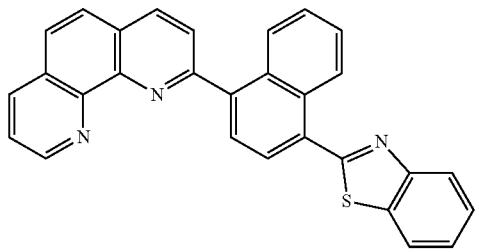

[Formula 8]

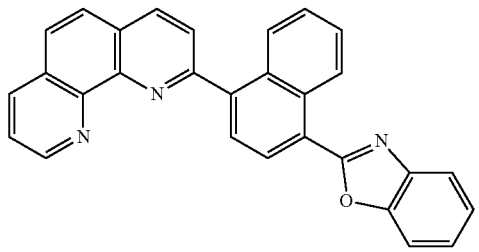

The properties, i.e., the driving voltage difference (ΔV), the efficiency, and the lifespan, of the OLEDs manufactured in Comparative Example 1 and Examples 1 to 5 are measured and listed in Table 1, and The properties, i.e., the driving voltage difference (ΔV), the efficiency, and the lifespan, of the OLEDs manufactured in Comparative Example 2 and Examples 6 to 10 are measured and listed in Table 2.

TABLE 1

|  | ETL | ΔV | efficiency | lifespan |
|---|---|---|---|---|
| Ref1 | Formula 7 | 0 V | 100% | 100% |
| Ex1 | C2 | 0 V | 118% | 115% |
| Ex2 | C4 | −0.1 V | 111% | 108% |
| Ex3 | C6 | −0 1 V | 105% | 111% |
| Ex4 | C8 | −0.2 V | 102% | 100% |
| Ex5 | C10 | −0.3 V | 95% | 86% |

TABLE 2

|  | ETL | ΔV | efficiency | lifespan |
|---|---|---|---|---|
| Ref2 | Formula 7 | 0 V | 100% | 100% |
| Ex6 | C14 | 0 V | 112% | 120% |
| Ex7 | C16 | −0.1 V | 109% | 114% |
| Ex8 | C18 | −0.1 V | 101% | 112% |
| Ex9 | C20 | −0.2 V | 98% | 103% |
| Ex10 | C22 | −0.3 V | 93% | 86% |

As shown in Tables 1 and 2, in the OLED of Ex1 to Ex10 using the organic compound of the present disclosure, where the benzothiazole moiety or the benzoxazole moiety is connected (linked, combined or joined) to the phenanthroline moiety directly or through the linker, in the ETL, the OLED has advantages in the driving voltage, the emitting efficiency and the lifespan.

In addition, in comparison to the compounds used in the OLED of Ref1 and Ref2, a thiazole part of the benzothiazole moiety or an oxazole part of the benzoxazole moiety is connected to the phenanthroline moiety directly or through the linker in the organic compound of the present disclosure, and the organic compound is included in the ETL. As a result, in the OLED, the driving voltage is further reduced, and the emitting efficiency and the lifespan are further improved.

Figure 4:
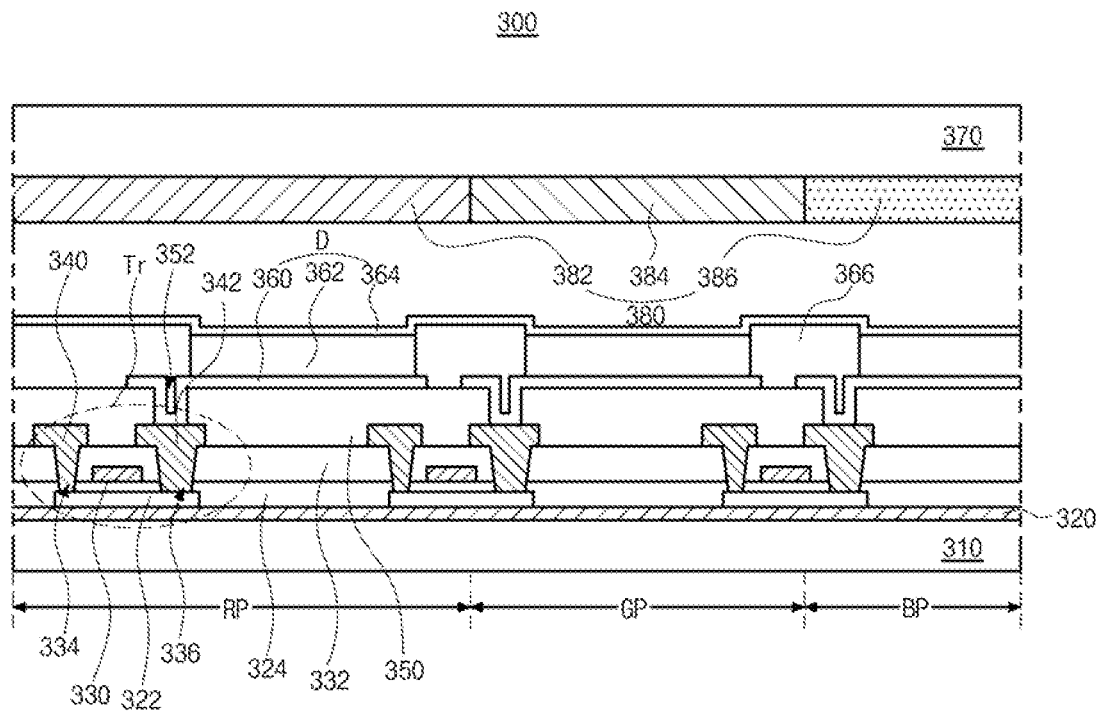
FIG. 4 is a schematic cross-sectional view of an organic light emitting device according to a third embodiment of the present disclosure.
Figure 5:
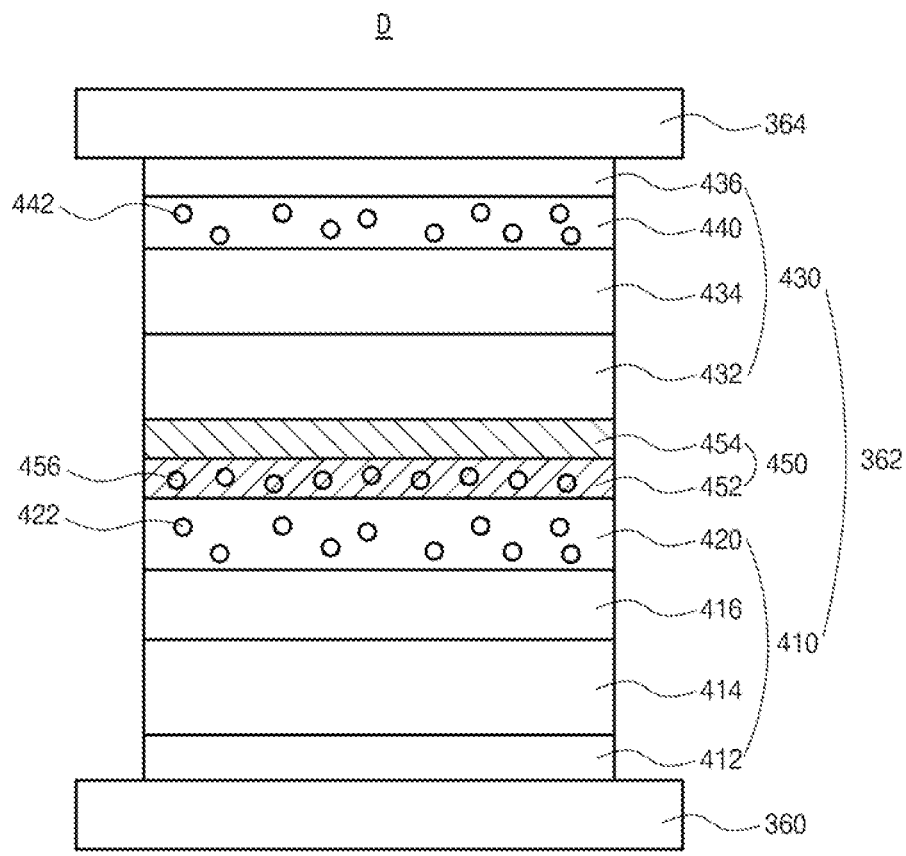
FIG. 5 is a schematic cross-sectional view of an OLED according to a fourth embodiment of the present disclosure.
Figure 6:
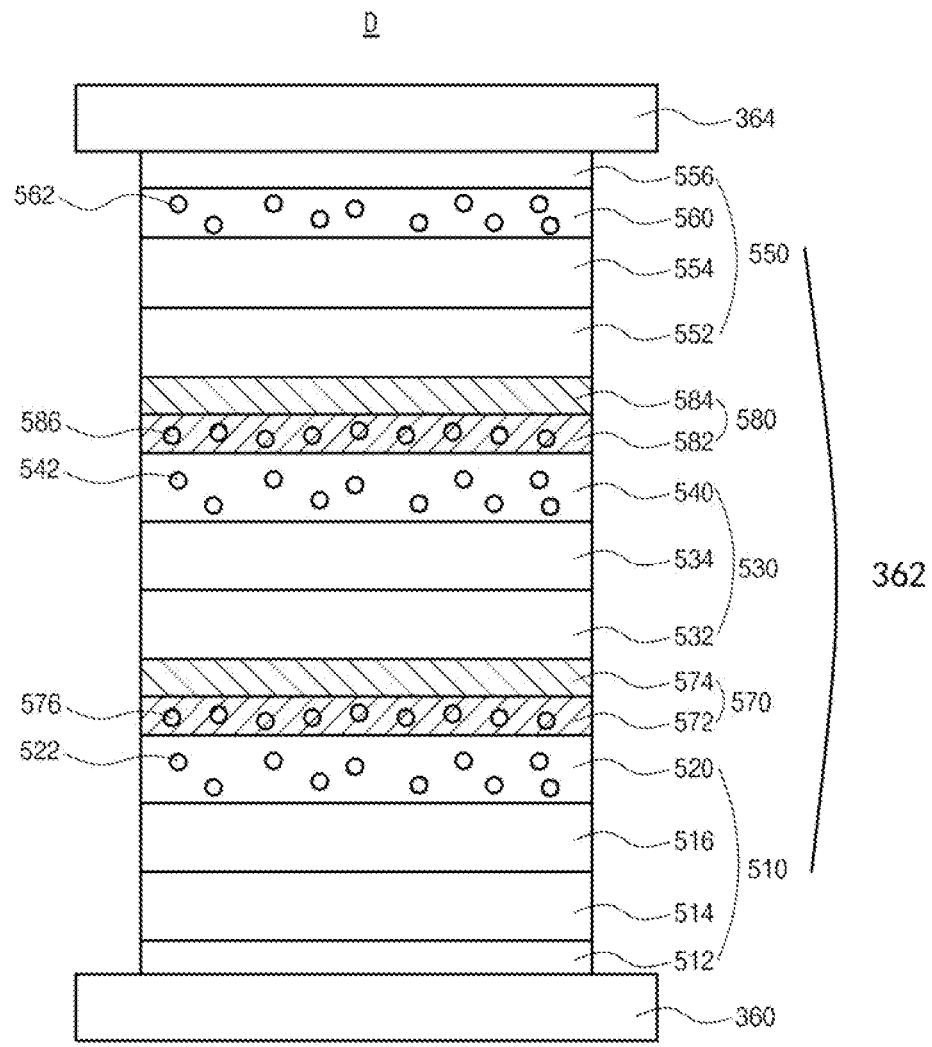
FIG. 6 is a schematic cross-sectional view of an OLED device according to a fifth embodiment of the present disclosure.

FIG. 4 is a schematic cross-sectional view of an organic light emitting device according to a third embodiment of the present disclosure. FIG. 5 is a schematic cross-sectional view of an OLED according to a fourth embodiment of the present disclosure, and FIG. 6 is a schematic cross-sectional view of an OLED device according to a fifth embodiment of the present disclosure.

As shown in FIG. 4, the organic light emitting display device 300 includes a first substrate 310, where a red pixel BP, a green pixel GP and a blue pixel BP are defined, a second substrate 370 facing the first substrate 310, an OLED D, which is positioned between the first and second substrates 310 and 370 and providing white emission, and a color filter layer 380 between the OLED D and the second substrate 370.

Each of the first and second substrates 310 and 370 can be a glass substrate or a flexible substrate. For example, each of the first and second substrates 310 and 370 can be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 320 is formed on the first substrate, and the TFT Tr corresponding to each of the red, green and blue pixels RP, GP and BP is formed on the buffer layer 320. The buffer layer 320 can be omitted.

A semiconductor layer 322 is formed on the buffer layer 320. The semiconductor layer 322 can include an oxide semiconductor material or polycrystalline silicon.

A gate insulating layer 324 is formed on the semiconductor layer 322. The gate insulating layer 324 can be formed of an inorganic insulating material such as silicon oxide or silicon nitride.

A gate electrode 330, which is formed of a conductive material, e.g., metal, is formed on the gate insulating layer 324 to correspond to a center of the semiconductor layer 322.

An interlayer insulating layer 332, which is formed of an insulating material, is formed on the gate electrode 330. The interlayer insulating layer 332 can be formed of an inorganic insulating material, e.g., silicon oxide or silicon nitride, or an organic insulating material, e.g., benzocyclobutene or photo-acryl.

The interlayer insulating layer 332 includes first and second contact holes 334 and 336 exposing both sides of the semiconductor layer 322. The first and second contact holes 334 and 336 are positioned at both sides of the gate electrode 330 to be spaced apart from the gate electrode 330.

A source electrode 340 and a drain electrode 342, which are formed of a conductive material, e.g., metal, are formed on the interlayer insulating layer 332.

The source electrode 340 and the drain electrode 342 are spaced apart from each other with respect to the gate electrode 330 and respectively contact both sides of the semiconductor layer 322 through the first and second contact holes 334 and 336.

The semiconductor layer 322, the gate electrode 330, the source electrode 340 and the drain electrode 342 constitute the TFT Tr. The TFT Tr serves as a driving element. Namely, the TFT Tr can correspond to the driving TFT Td (of FIG. 1).

The gate line and the data line cross each other to define the pixel, and the switching TFT is formed to be connected to the gate and data lines. The switching TFT is connected to the TFT Tr as the driving element.

In addition, the power line, which can be formed to be parallel to and spaced apart from one of the gate and data lines, and the storage capacitor for maintaining the voltage of the gate electrode of the TFT Tr in one frame can be further formed.

A planarization layer 350, which includes a drain contact hole 352 exposing the drain electrode 342 of the TFT Tr, is formed to cover the TFT Tr.

A first electrode 360, which is connected to the drain electrode 342 of the TFT Tr through the drain contact hole 352, is separately formed in each pixel and on the planarization layer 350. The first electrode 360 can be an anode and can be formed of a conductive material, e.g., a transparent conductive oxide (TCO), having a relatively high work function. The first electrode 360 can further include a reflection electrode or a reflection layer. For example, the reflection electrode or the reflection layer can be formed of silver (Ag) or aluminum-palladium-copper (APC) alloy. In the top-emission type organic light emitting display device 300, the first electrode 360 can have a triple-layered structure of ITO/Ag/ITO or ITO/AP C/ITO.

A bank layer 366 is formed on the planarization layer 350 to cover an edge of the first electrode 360. Namely, the bank layer 366 is positioned at a boundary of the pixel and exposes a center of the first electrode 360 in the pixel. Since the OLED D emits the white light in the red, green and blue pixels RP, GP and BP, the organic emitting layer 362 can be formed as a common layer in the red, green and blue pixels RP, GP and BP without separation. The bank layer 366 can be formed to prevent a current leakage at an edge of the first electrode 360 and can be omitted.

An organic emitting layer 362 is formed on the first electrode 360.

Referring to FIG. 5, the OLED D includes the first and second electrodes 360 and 364 facing each other and the organic emitting layer 362 between the first and second electrodes 360 and 364. The organic emitting layer 362 includes a first emitting part 410 including a first EML 416 and a first ETL 420, a second emitting part 430 including a second EML 434 and a second ETL 440, and a charge generation layer (CGL) 450 between the first and second emitting parts 410 and 430.

The CGL 450 is positioned between the first and second emitting parts 410 and 430, and the first emitting part 410, the CGL 450 and the second emitting part 430 are sequentially stacked on the first electrode 360. Namely, the first emitting part 410 is positioned between the first electrode 360 and the CGL 450, and the second emitting part 430 is positioned between the second electrode 364 and the CGL 450.

In the first emitting part 410, the first ETL 420 is positioned on or over the first EML 416.

The first emitting part 410 can further include a first HTL 414 between the first electrode 360 and the first EML 416. In addition, the first emitting part 410 can further include an HIL 412 between the first electrode 360 and the first HTL 414.

The first emitting part 410 can further include at least one of an EBL between the first HTL 414 and the first EML 416 and an HBL between the first EML 416 and the first ETL 420.

In the second emitting part 430, the second ETL 440 is positioned on or over the second EML 434.

The second emitting part 430 can further include a second HTL 432 between the second EML 434 and the CGL 450.

In addition, the second emitting part 430 can further include an EIL 436 between the second electrode 364 and the second ETL 440.

The second emitting part 430 can further include at least one of an EBL between the second HTL 432 and the second EML 434 and an HBL between the second EML 434 and the second ETL 440.

One of the first and second EMLs 416 and 434 provides blue light, and the other one of the first and second EMLs 416 and 434 provides yellow-green light. For example, the first EML 416 can provide blue light and can include a host and a blue dopant. The second EML 434 can provide yellow-green light and can include a host and a yellow-green dopant. Alternatively, the second EML 434 can have a double-layered structure of a first layer emitting red light and a second layer emitting green light. In this instance, the first layer emitting red light can include a host and a red dopant, and the second layer emitting green light can include a host and a green dopant.

For example, in the first EML 416 emitting blue light, a host can be an anthracene derivative, and a blue dopant can be a pyrene derivative.

The CGL 450 includes an n-type CGL 452 and a p-type CGL 454. The n-type CGL 452 is positioned between the first ETL 420 and the second HTL 432, and the p-type CGL 454 is positioned between the n-type CGL 452 and the second HTL 432.

The n-type CGL 452 provides the electron toward the first ETL 420, and the electron is transferred into the first EML 416 through the first ETL 420. The p-type CGL 454 provides the hole toward the second HTL 432, and the hole is transferred into the second EML 434 through the second HTL 432. As a result, in the OLED D having a two-stack (double-stack) structure, the driving voltage is reduced, and the emitting efficiency is improved.

The p-type CGL 454 can be formed of an organic material doped with metal or p-type dopant. For example, the metal doped into the p-type CGL 454 can be selected from the group consisting of Al, Cu, Fe, Pb, Zn, Au, Pt, W, In, Mo, Ni and Ti, and the p-type dopant can be F4-TCNQ. The organic material for the p-type CGL 454 can be selected from the group consisting of NPB, TPD, N,N,N',N'-tetranaphthalenyl-benzidine (TNB) and HAT-CN.

Alternatively, the p-type CGL 454 can include the compound in Formula 9-1 or 9-2.

[Formula 9-1]

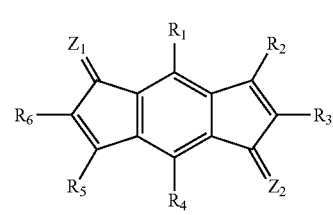

[Formula 9-2]

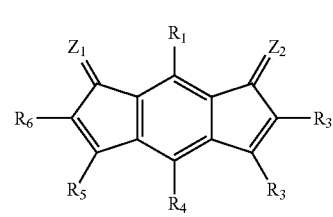

In Formula 9-1 and 9-2, each of $R_1$ to $R_6$ is independently selected from the group consisting of H, C6 to C30 aryl group, C6 to C30 heteroaryl group, C1 to C12 alkyl group, C1 to C12 alkoxy group, C2 to C12 ether group, cyano, fluorine, trifluoromethyl, trifluoromethoxy and trimethylsilyl, and at least one of $R_1$ to $R_6$ is cyano.

Each of Z1 and Z2 is independently represented by Formula 10.

[Formula 10]

In Formula 10, each of A and B is independently selected from the group consisting of H, C6 to C30 aryl group, C6 to C30 heteroaryl group, C1 to C12 alkyl group, C1 to C12 alkoxy group, C2 to C12 ether group, cyano, fluorine, trifluoromethyl, trifluoromethoxy and trimethylsilyl. Formula 10 attaches to the structure of Formula 9-1 or 9-2 at a carbon between A and B of Formula 10 through a double bond of Formula 9-1 or 9-2.

In Formulas 9-1, 9-2 and 10, aryl group, heteroaryl group, alkyl group, alkoxy group and ether group can be unsubstituted or substituted with at least one of C6 to C30 aryl group, C6 to C30 heteroaryl group, C1 to C12 alkyl group, cyano, fluorine, trifluoromethyl, trifluoromethoxy and trimethylsilyl.

The compound in Formula 9-1 or 9-2 can be one of the compounds in Formula 11.

[Formula 11]

A01

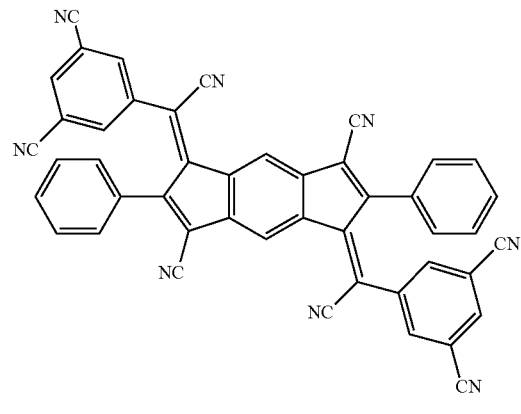

A02

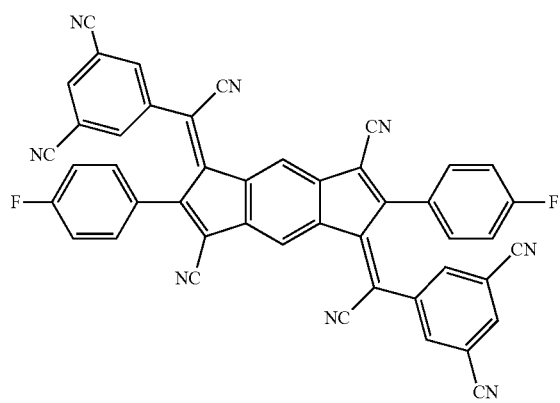

A03

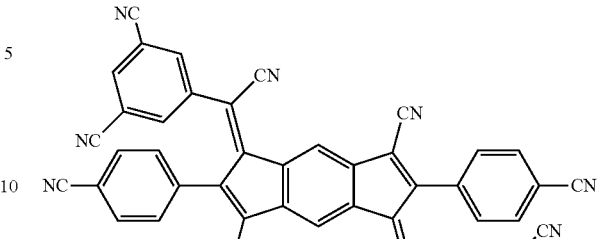

A04

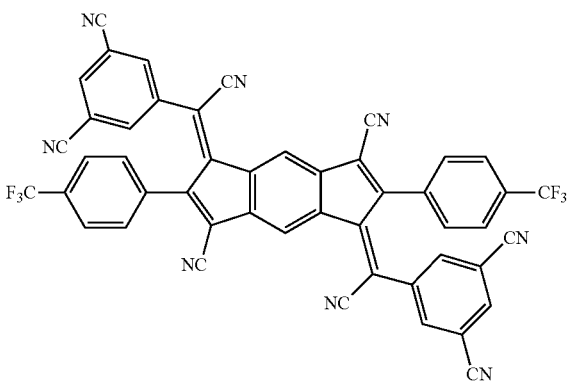

A05

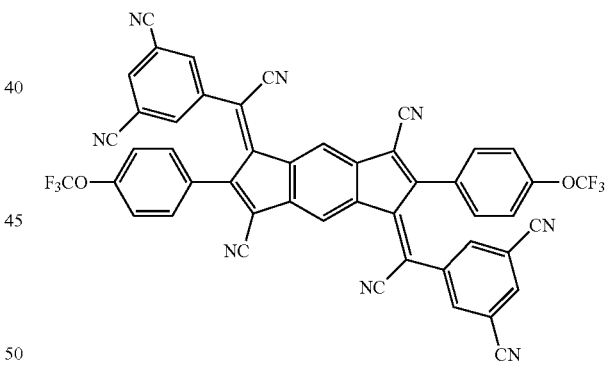

A06

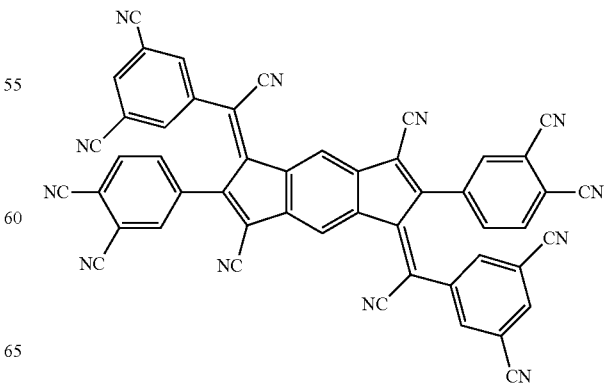

-continued
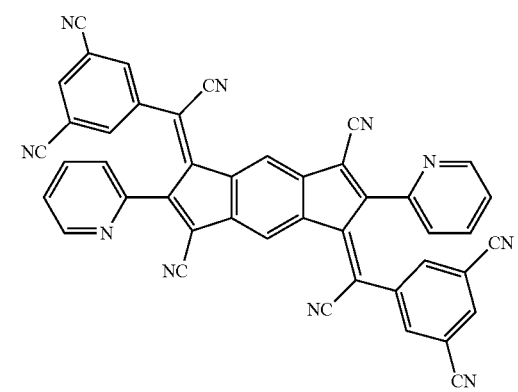
A07
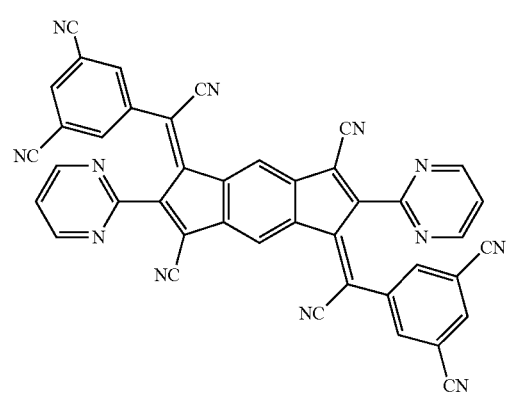
A08
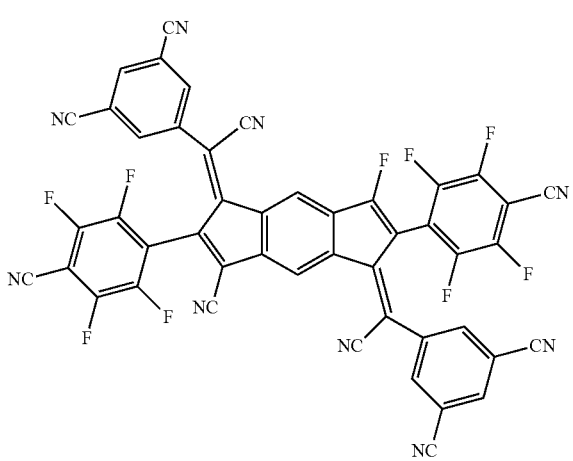
A09
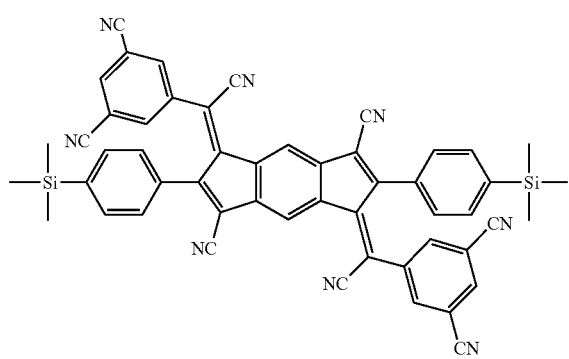
A10
-continued
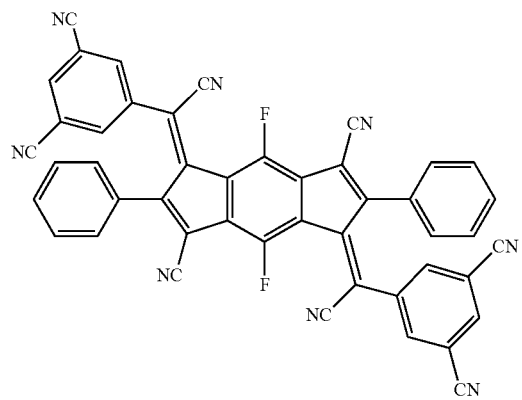
A11
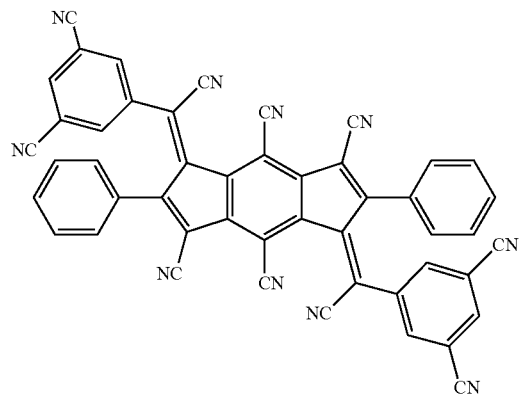
A12
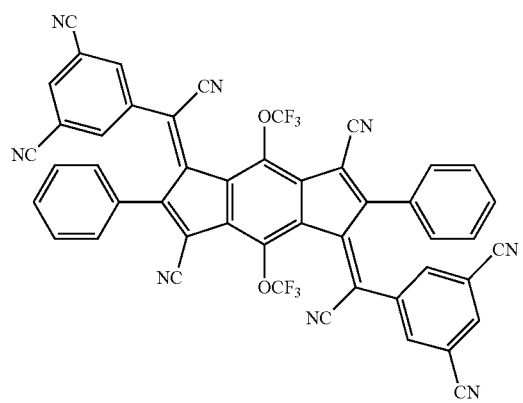
A13
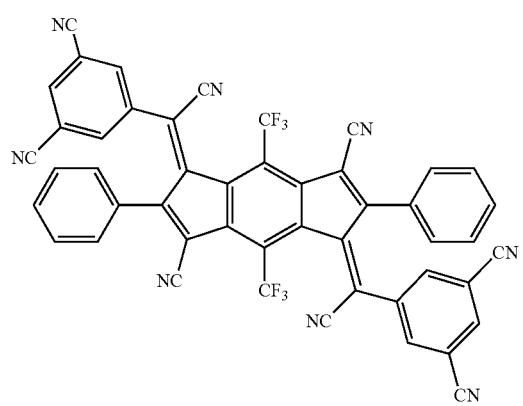
A14

A15
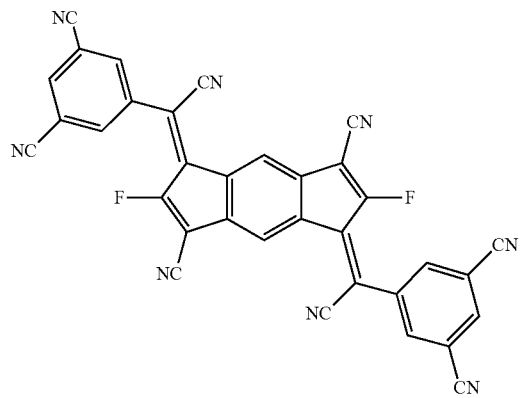
A16
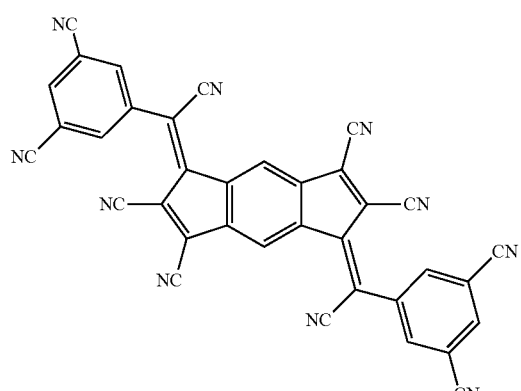
A17
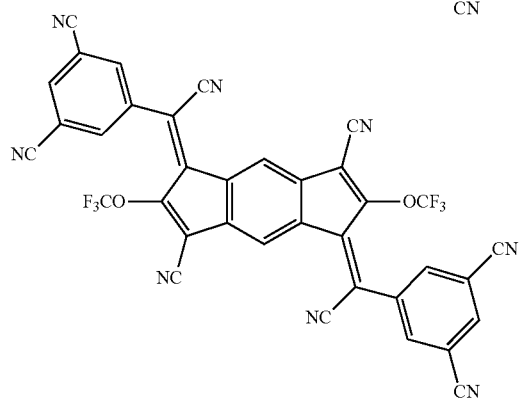
A18
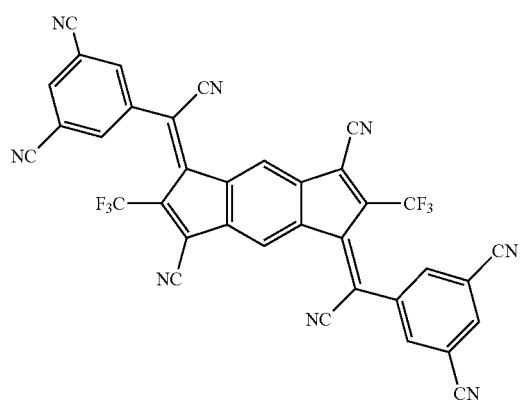
A19
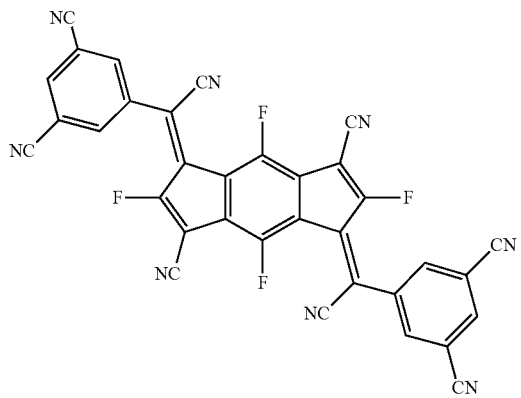
A20
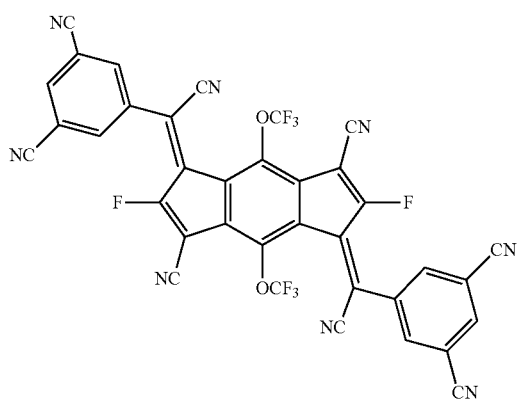
A21
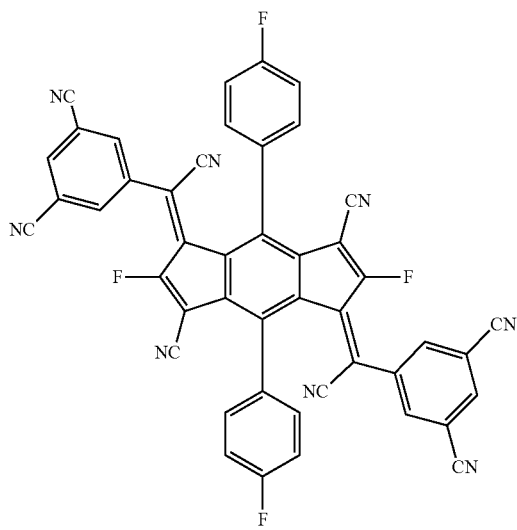

-continued
A22
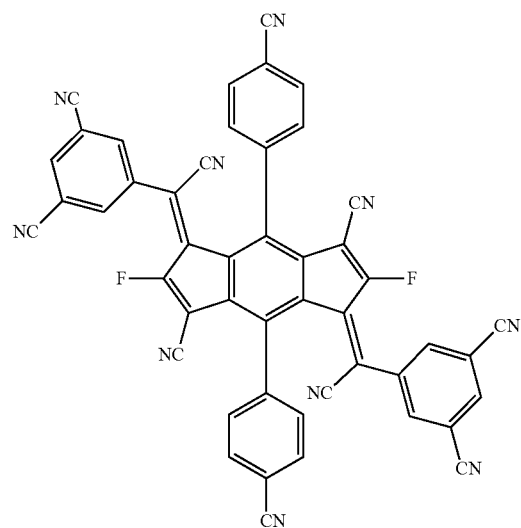
A23
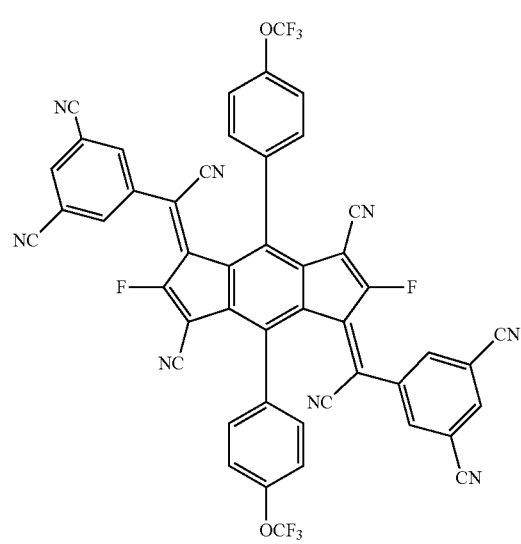
A24
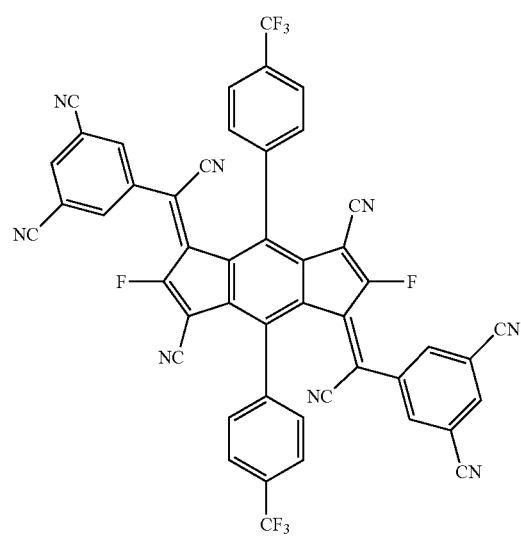
-continued
A25
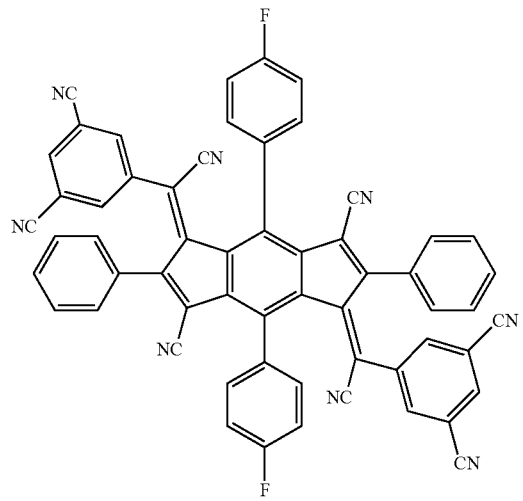
A26
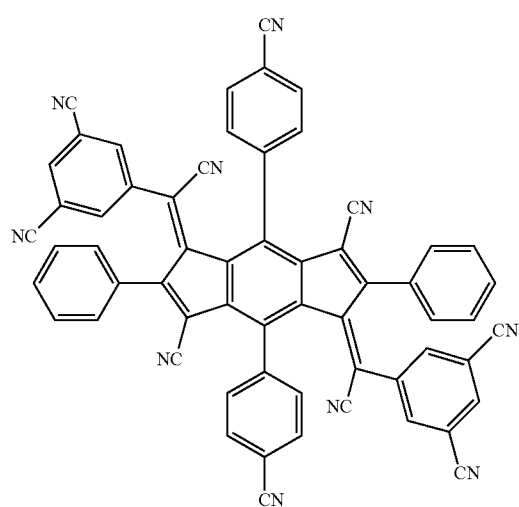
A27
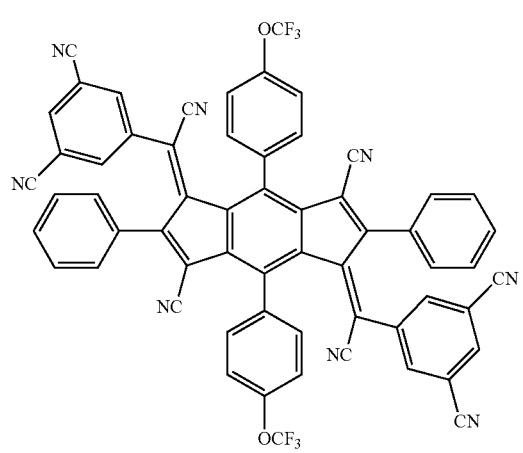

-continued
A28
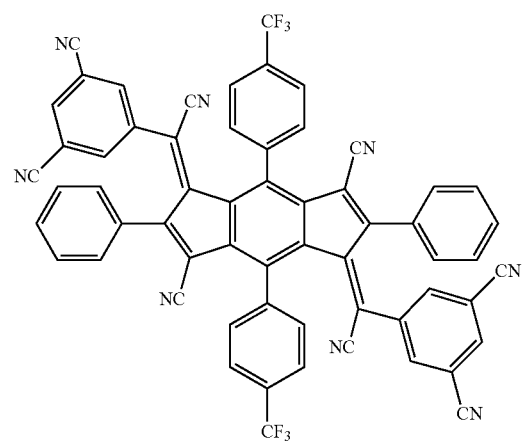
A29
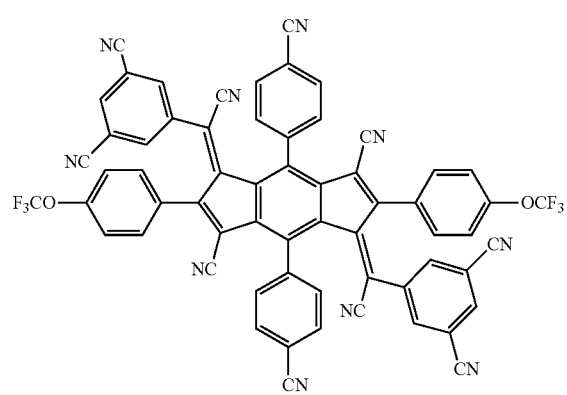
A30
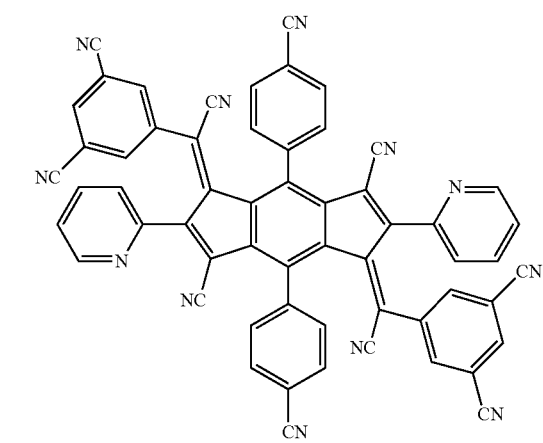
A31
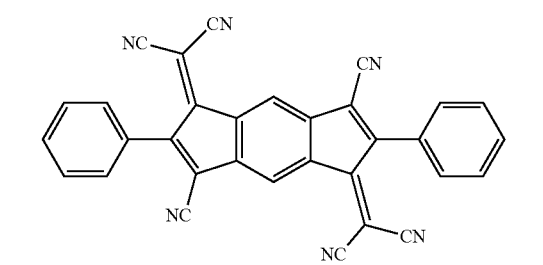
-continued
A32
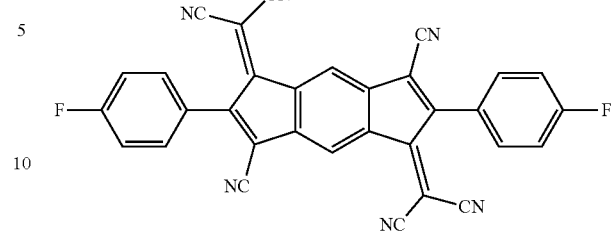
A33
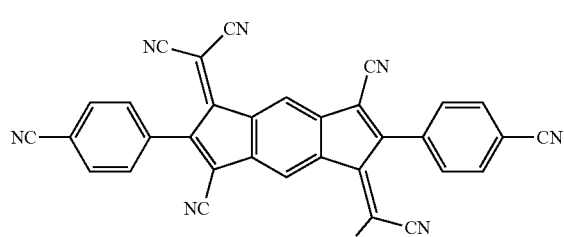
A34
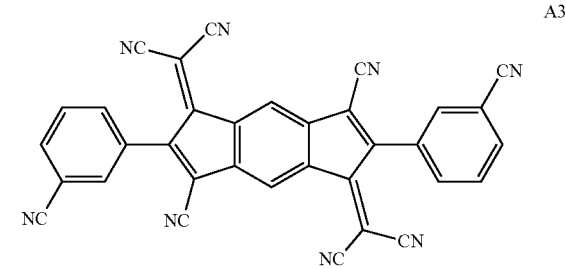
A35
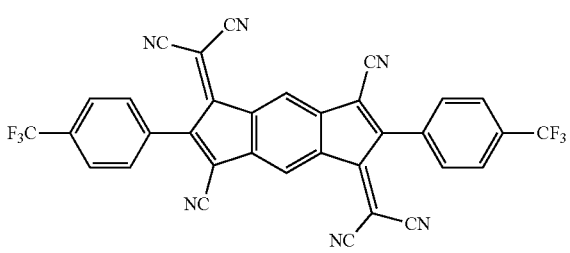
A36
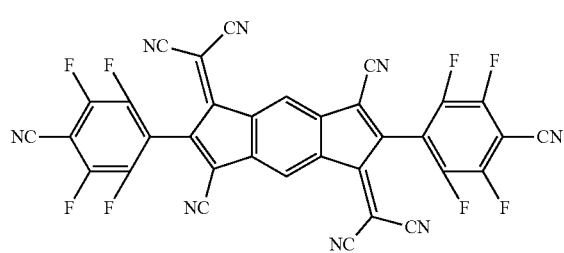
A37
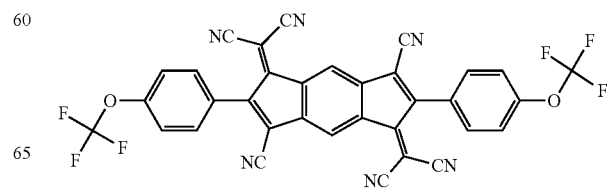

-continued
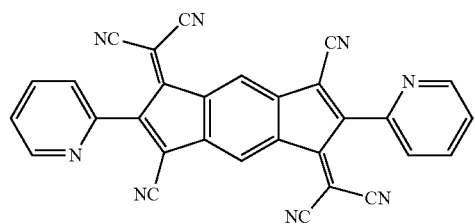
A38
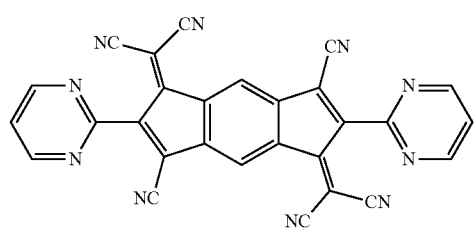
A39
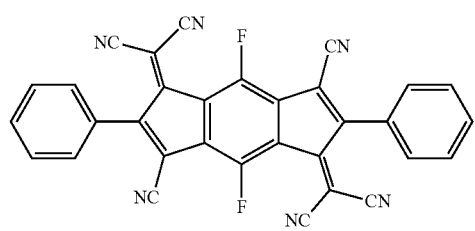
A40
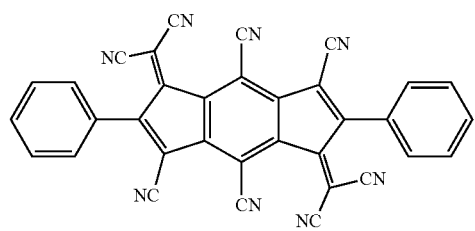
A41
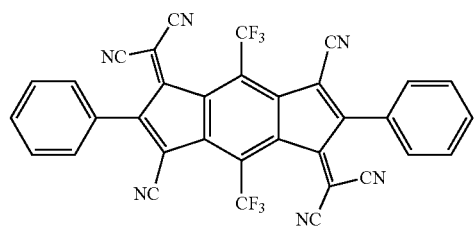
A42
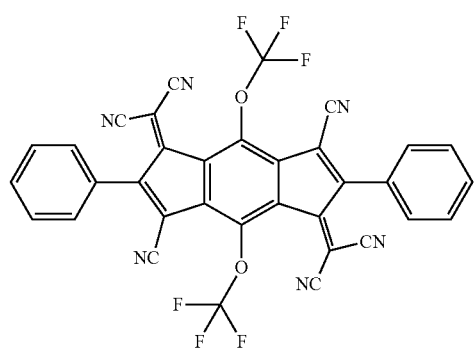
A43
-continued
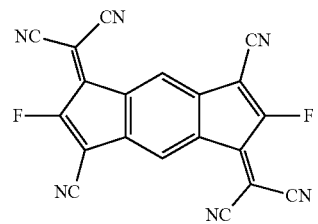
A44
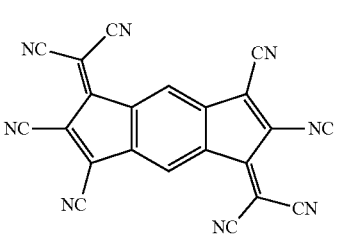
A45
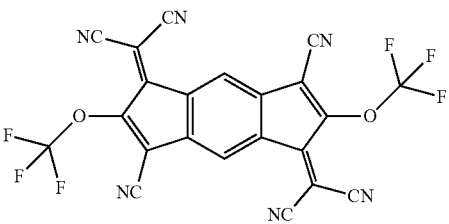
A46
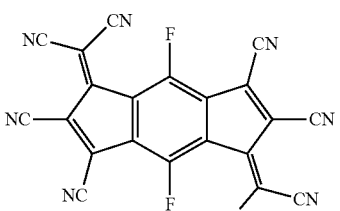
A47
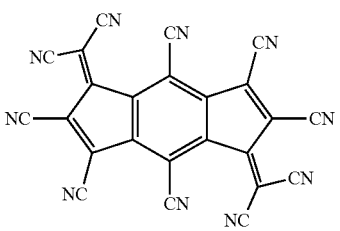
A48
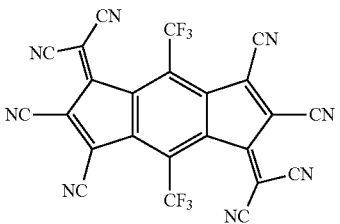
A49

-continued
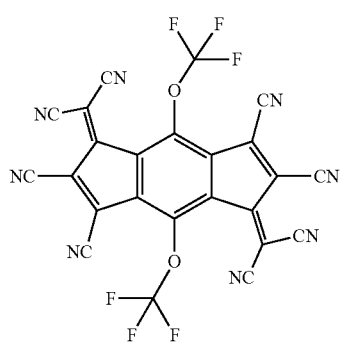
A50
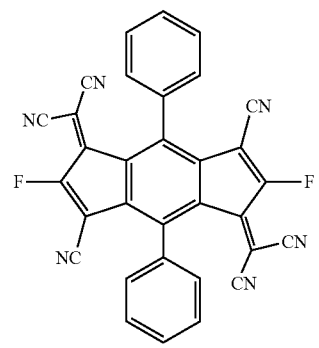
A51
A52
A53
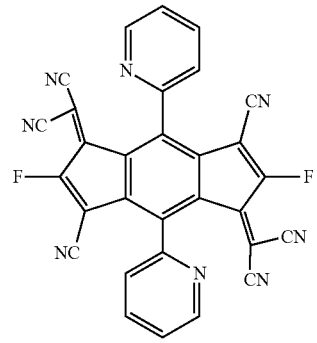
A54
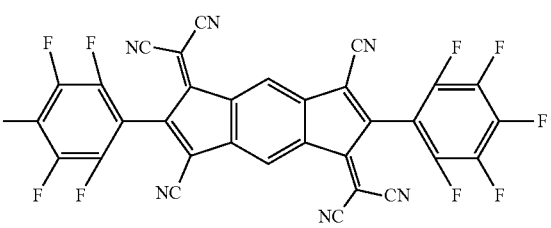
A55
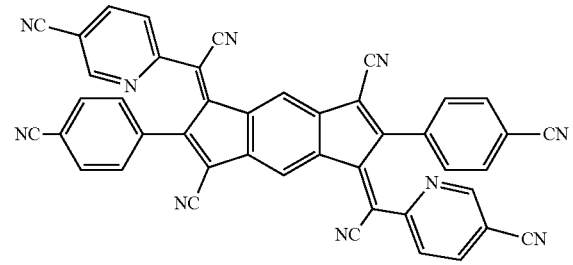
A56
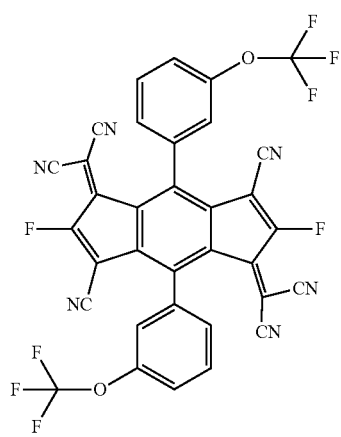
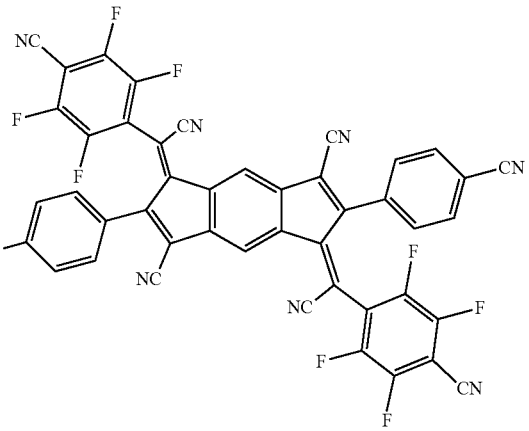
A57

A58
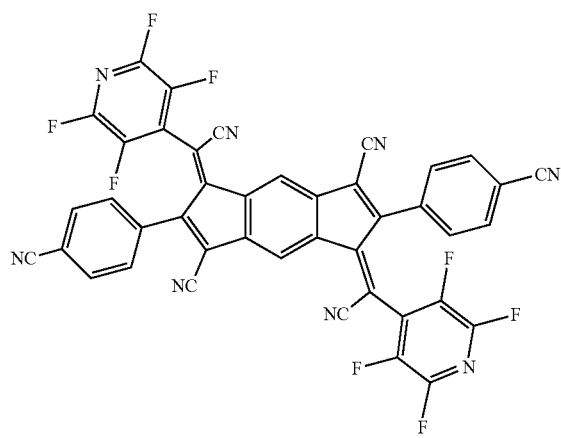
A59
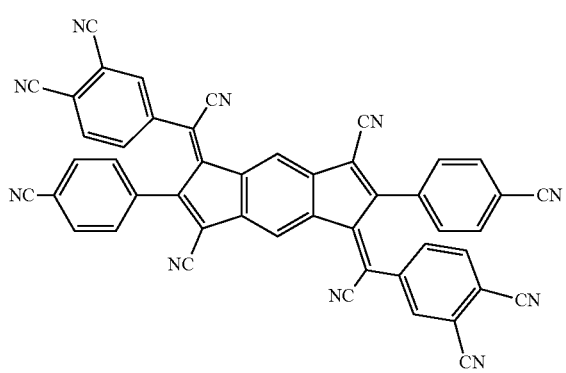
A60
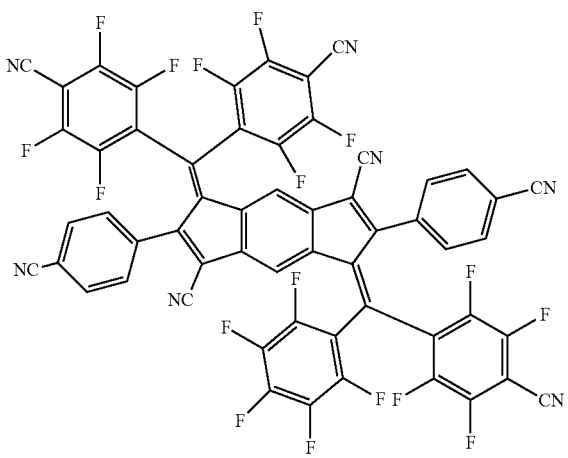
A61
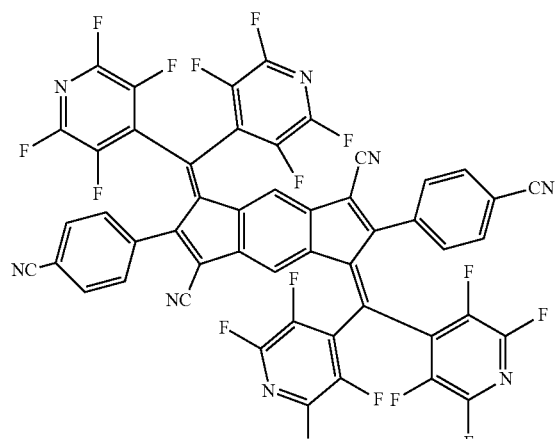
A62
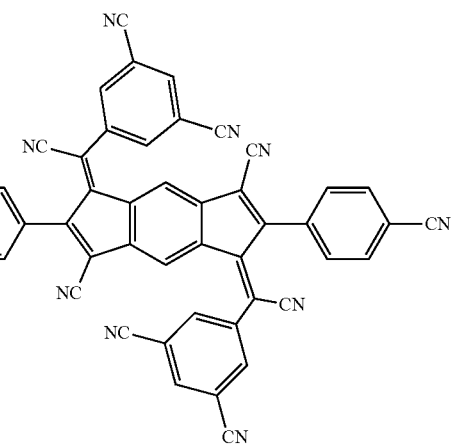
A63
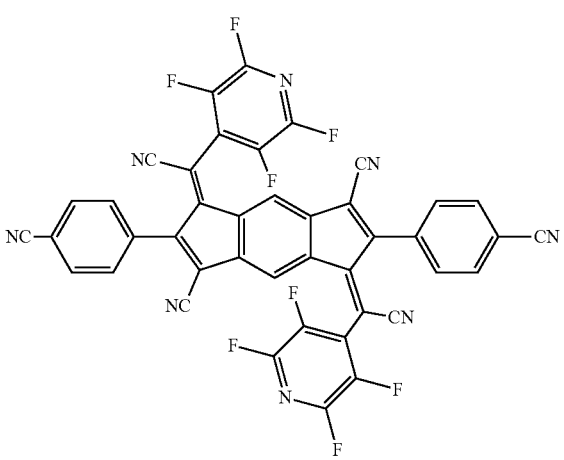
A64
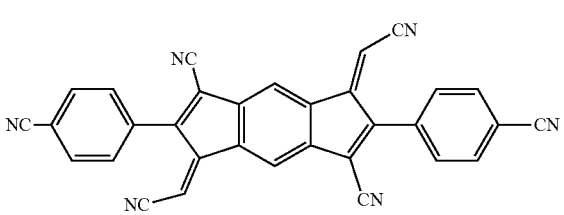

-continued
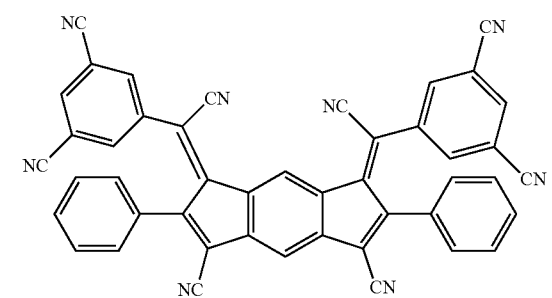
B1
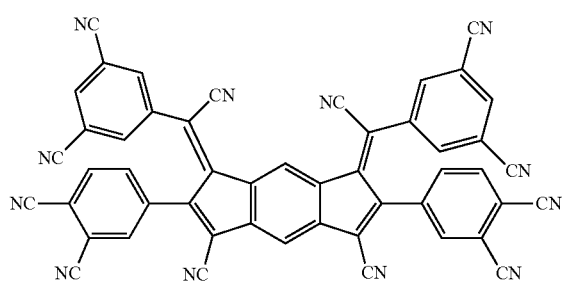
B6
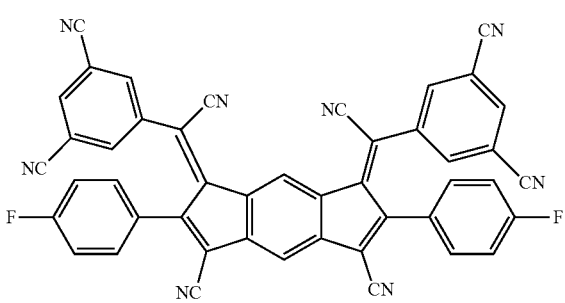
B2
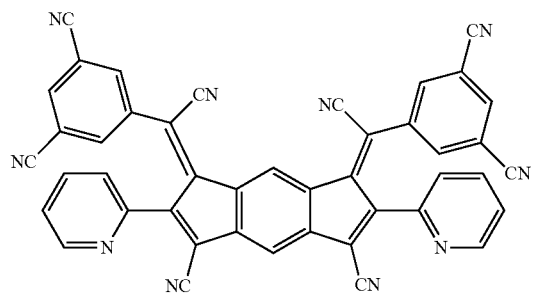
B7
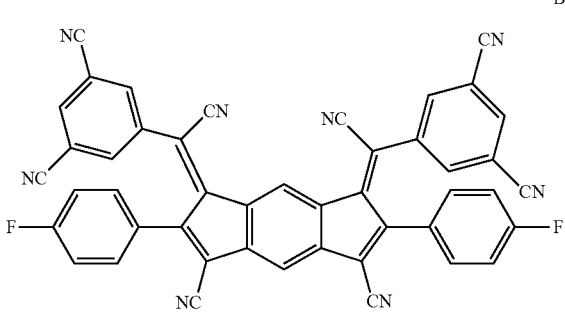
B3
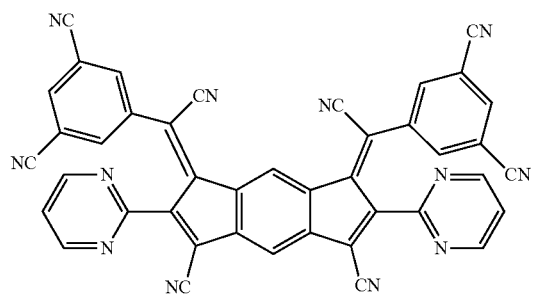
B8
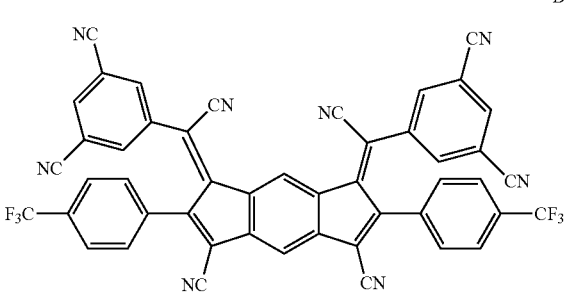
B4
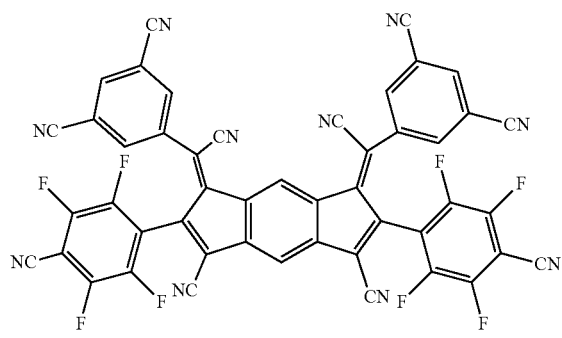
B9
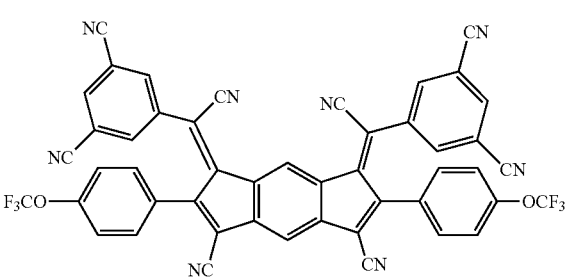
B5
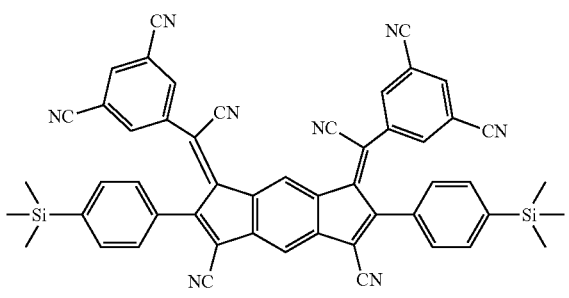
B10

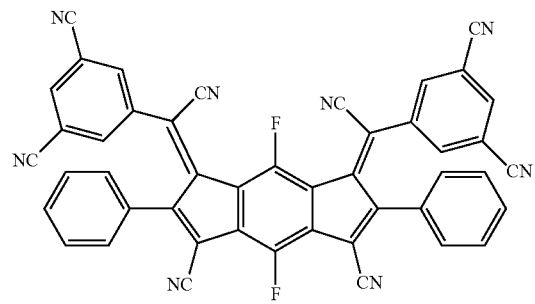
B11
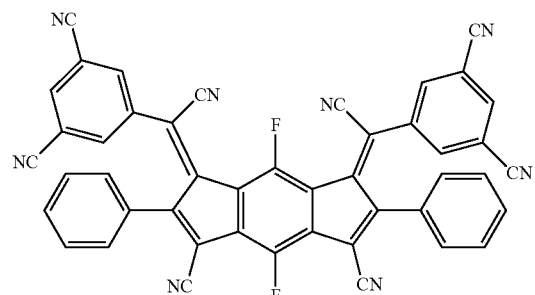
B11
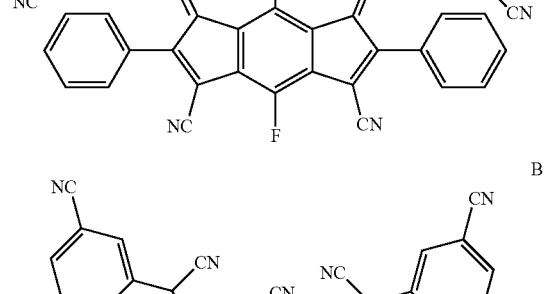
B12
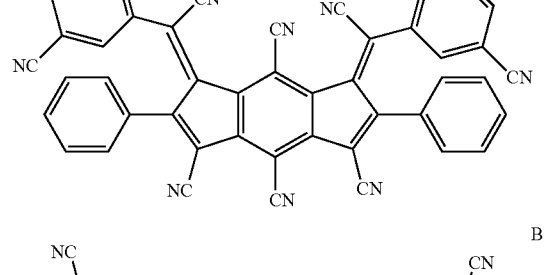
B13
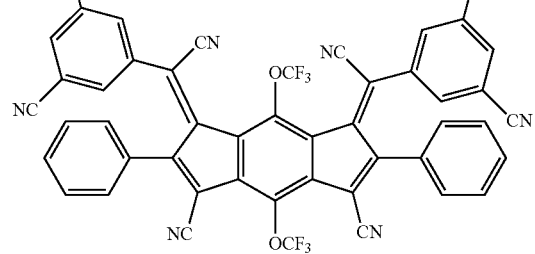
B14
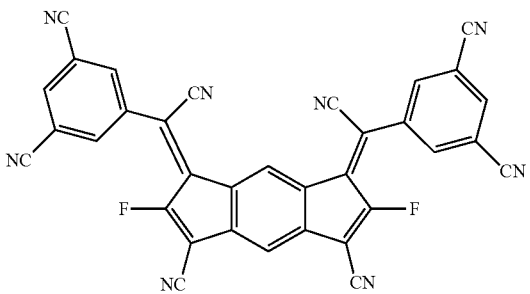
B15
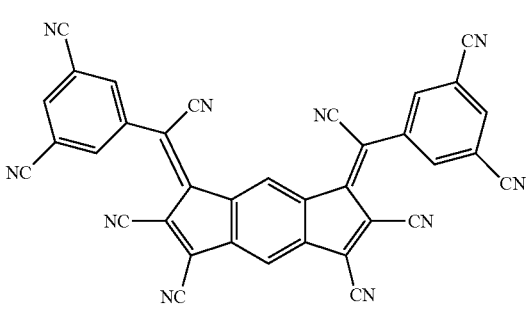
B16
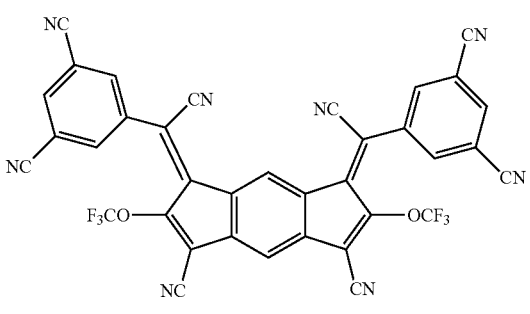
B17
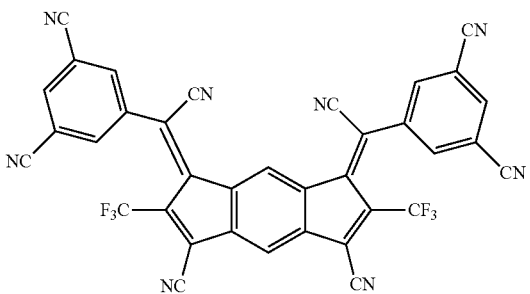
B18
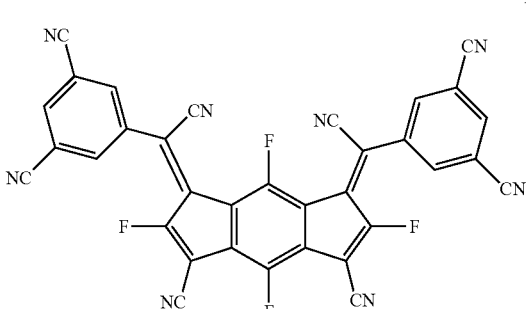
B19

B20
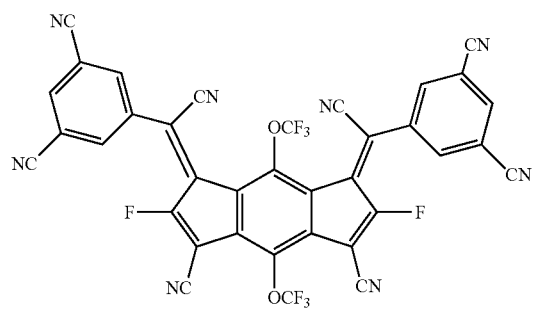
B21
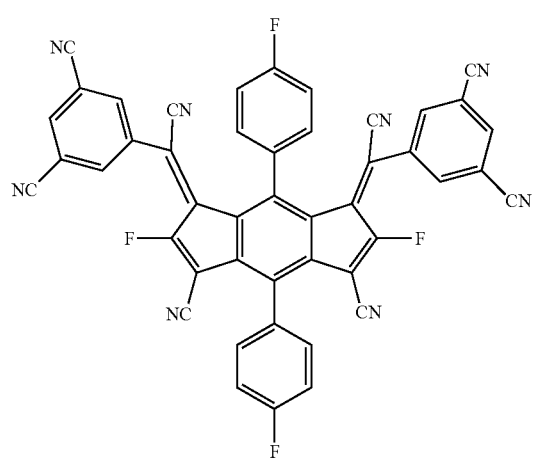
B22
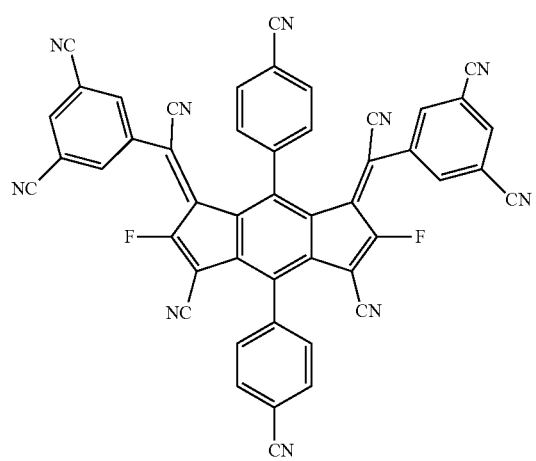
B23
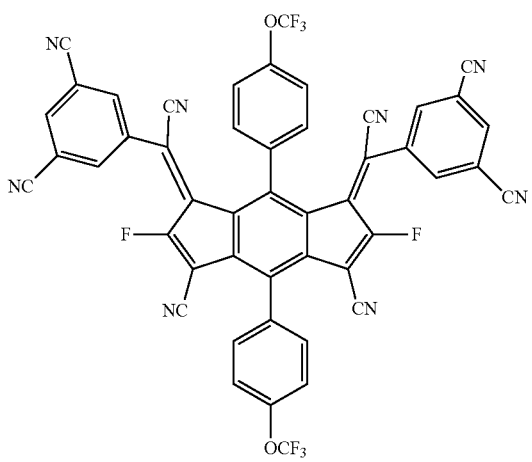
B24
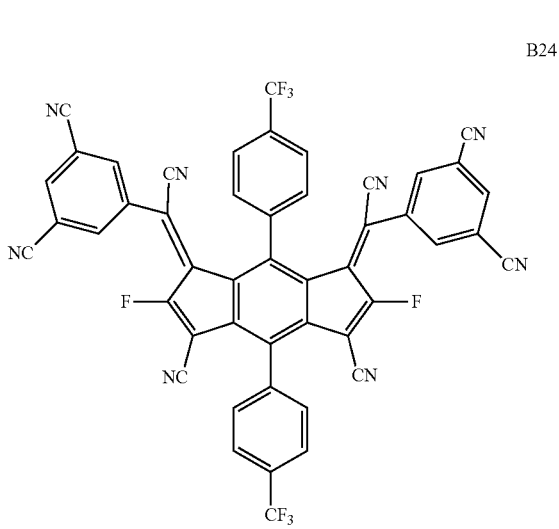
B25
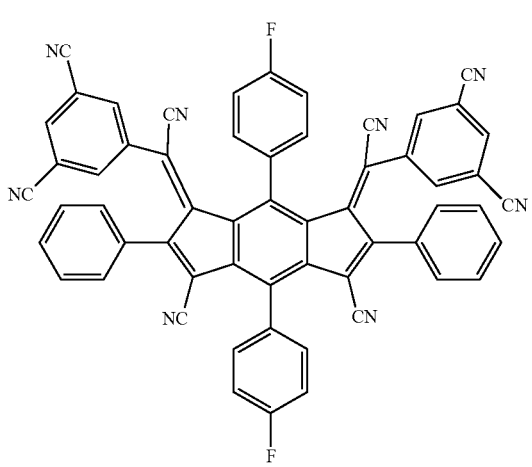

-continued
B26
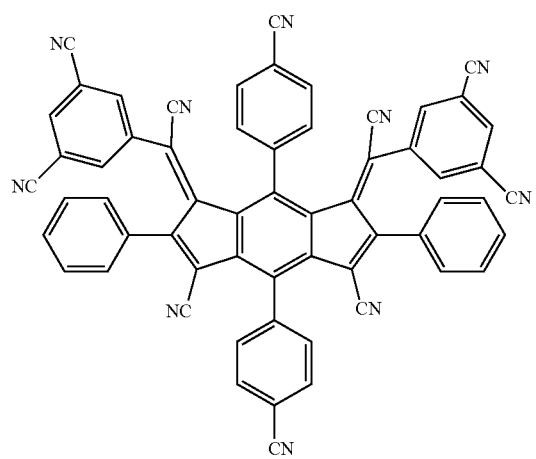
B27
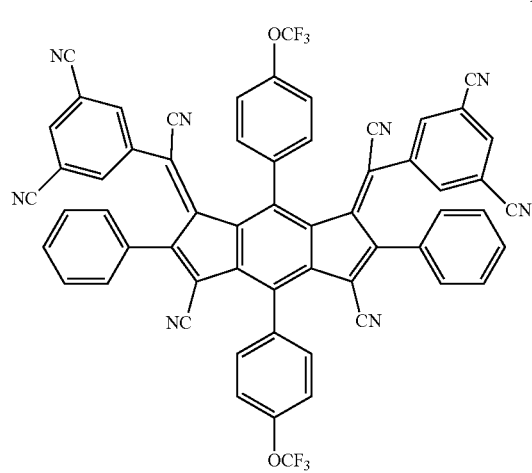
B28
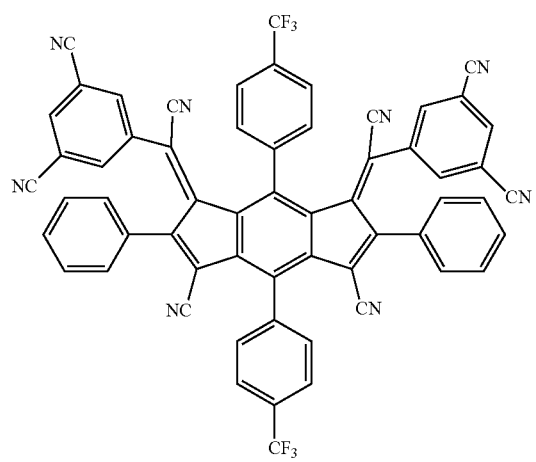
-continued
B29
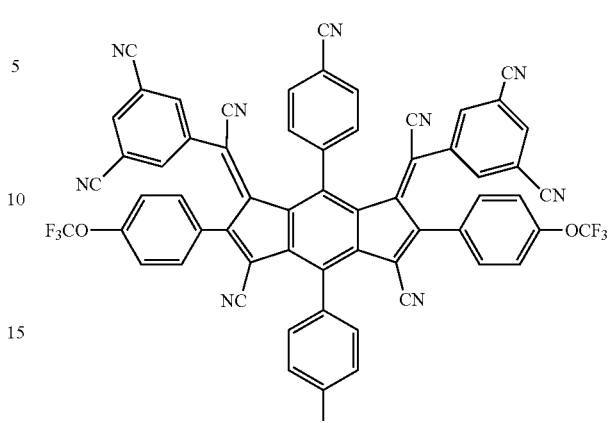
B30
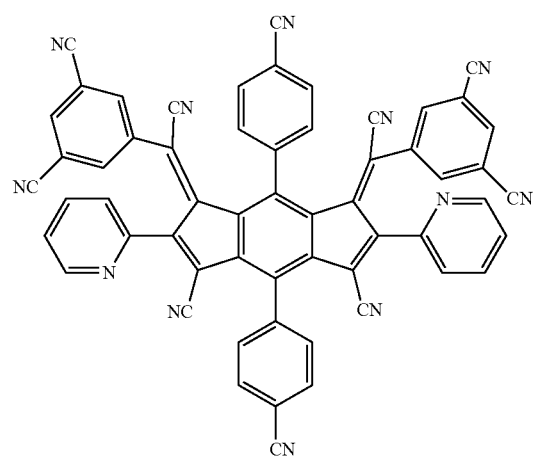
B31
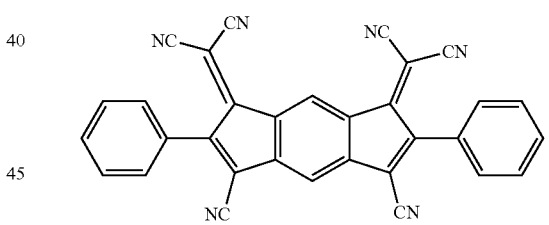
B32
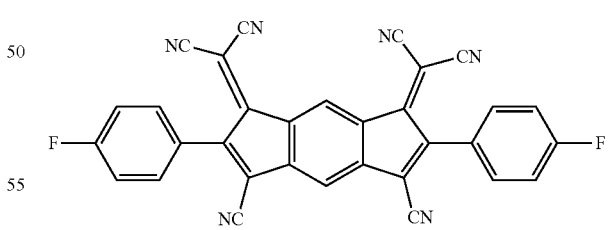
B33
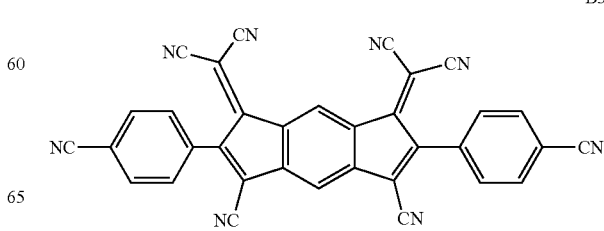

-continued
B34
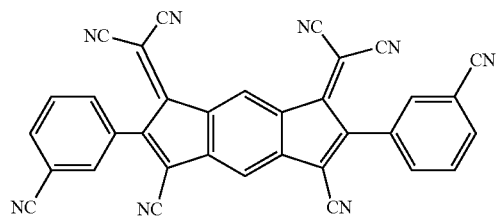
B35
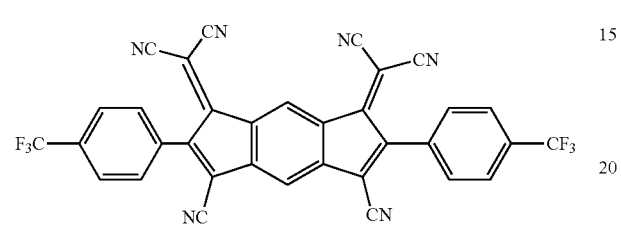
B36
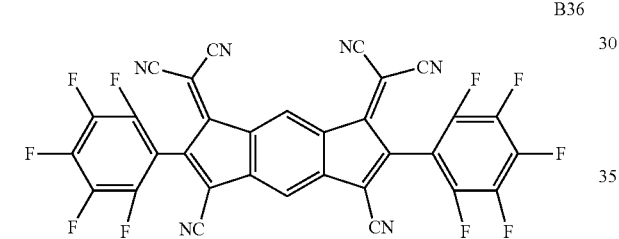
B37
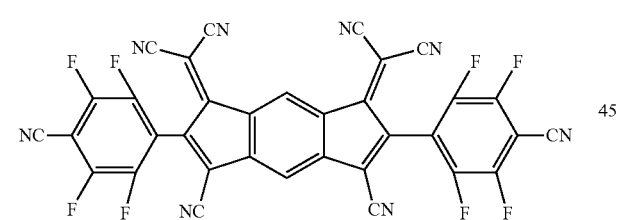
B38
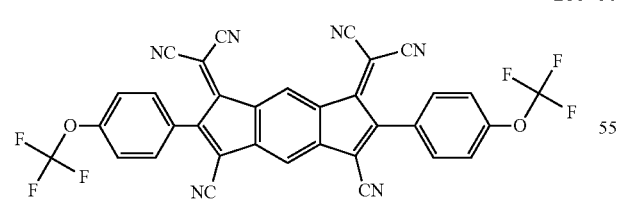
B39
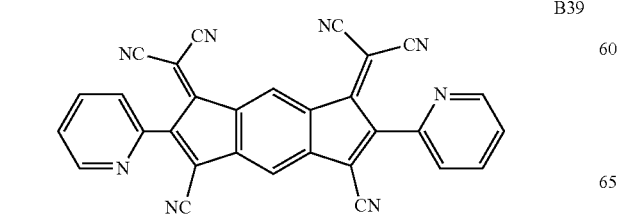
-continued
B40
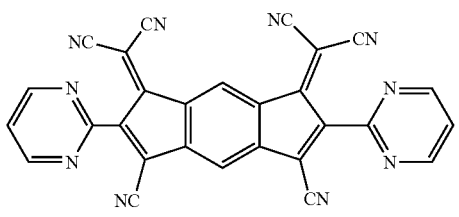
B41
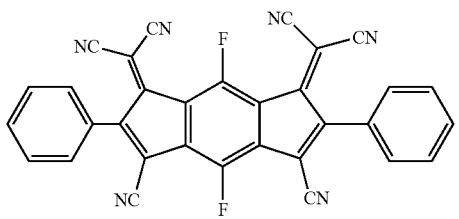
B42
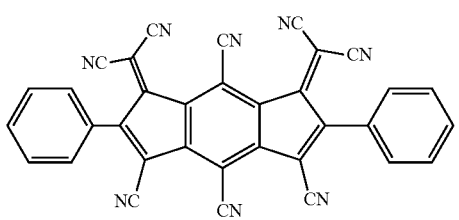
B43
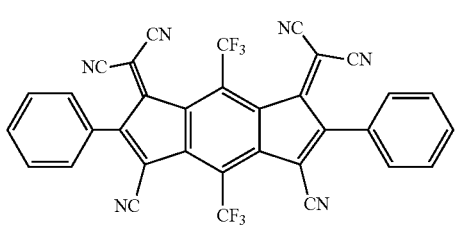
B44
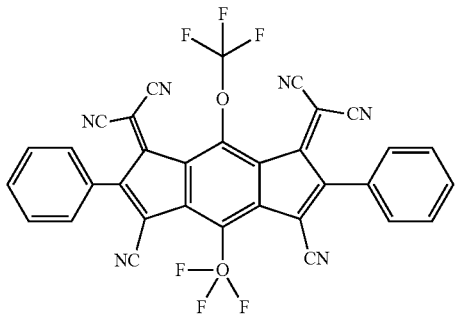
B45
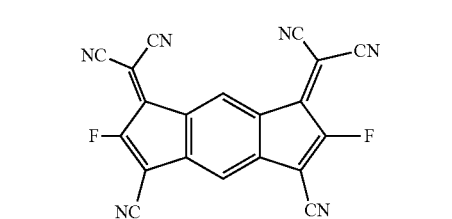
B46
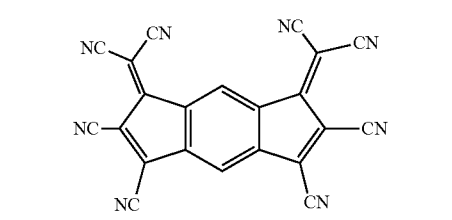

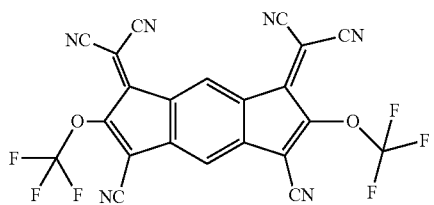

B47

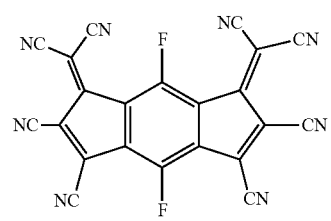

B48

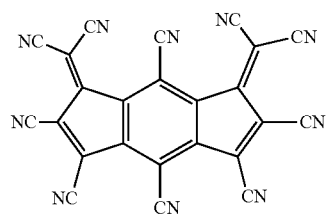

B49

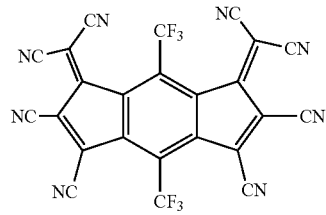

B50

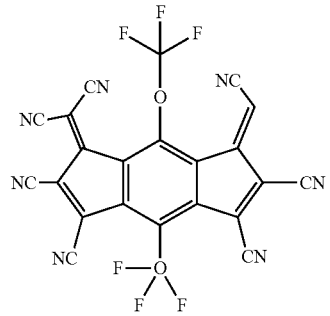

B51

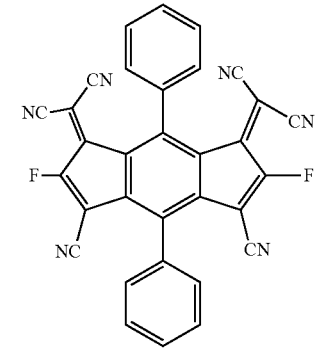

B52

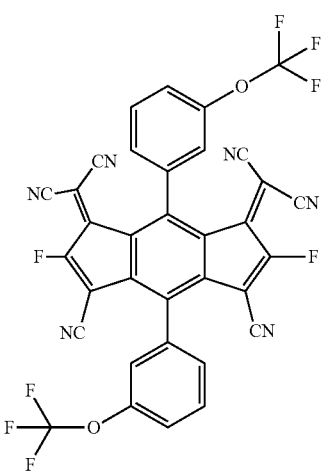

B53

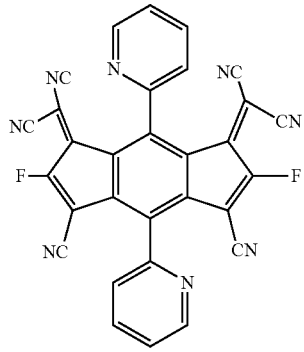

B54

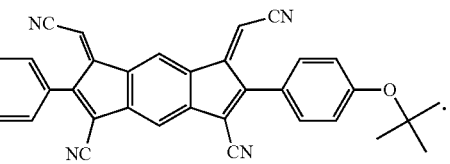

B55

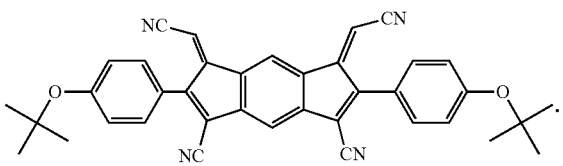

B56

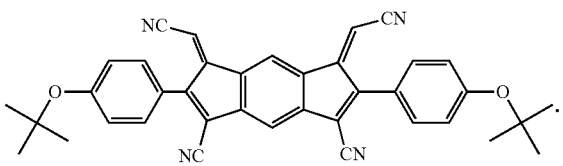

At least one of the first ETL 420, the n-type CGL 452 and the second ETL 440 includes the organic compound in Formula 1-1. For example, the first ETL 420 can include the organic compound of the present disclosure as a first electron transporting material 422. The second ETL 440 can include the organic compound of the present disclosure as a second electron transporting material 442. The n-type CGL 452 can include the organic compound of the present disclosure as an n-type charge generation material 456.

The first electron transporting material 422 in the first ETL 420, the second electron transporting material 442 in the second ETL 440 and the n-type charge generation material 456 in the n-type CGL 452 can be same or different.

When the n-type CGL 452 include the organic compound as the n-type charge generation material 456, the n-type CGL 452 can further include an auxiliary n-type charge generation material. For example, the auxiliary n-type charge generation material can be alkali metal, e.g., Li, Cs, K, Rb, Na or Fr, or alkali earth metal, e.g., Be, Mg, Ca, Sr, Ba or Ra. In the n-type CGL 452, the auxiliary n-type charge generation material can have a weight % of about 0.1 to 10, preferably about 0.5 to 5.

The OLED D including the first emitting part 410 providing blue light and the second emitting part 430 providing yellow-green light provides the white emission, and the CGL 450 is provided between the first and second emitting parts 410 and 430. As a result, the OLED D has advantages in the driving voltage, the emitting efficiency and the lifespan.

Referring to FIG. 6, the organic emitting layer 362 includes a first emitting part 510 including a first EML 516 and a first ETL 520, a second emitting part 530 including a second EML 534 and a second ETL 540, a third emitting part 550 including a third EML 554 and a third ETL 560, a first CGL 570 between the first and second emitting parts 510 and 530, and a second CGL 580 between the second and third emitting parts 530 and 550.

The first CGL 570 is positioned between the first and second emitting parts 510 and 530, and the second CGL 580 is positioned between the second and third emitting parts 530 and 550. Namely, the first emitting part 510, the first CGL 570, the second emitting part 530, the second CGL 580 and the third emitting part 550 are sequentially stacked on the first electrode 360. In other words, the first emitting part 510 is positioned between the first electrode 360 and the first CGL 570, the second emitting part 530 is positioned between the first and second CGLs 570 and 580, and the third emitting part 550 is positioned between the second electrode 364 and the second CGL 580.

In the first emitting part 510, the first ETL 520 is positioned on or over the first EML 516.

The first emitting part 510 can further include a first HTL 514 positioned between the first electrode 360 and the first EML 516. The first emitting part 510 can further include an HIL 512 between the first electrode 360 and the first HTL 514.

The first emitting part 510 can further include at least one of an EBL between the first HTL 514 and the first EML 516 and an HBL between the first EML 516 and the first ETL 520.

In the second emitting part 530, the second ETL 540 is positioned on or over the second EML 534.

The second emitting part 530 can further include a second HTL 532 under the second EML 534.

The second emitting part 530 can further include at least one of an EBL between the second HTL 532 and the second EML 534 and an HBL between the second EML 534 and the second ETL 540.

In the third emitting part 550, the third ETL 560 is positioned on or over the third EML 554.

The third emitting part 550 can further include a third HTL 552 between the third EML 554 and the second CGL 580. The third emitting part 550 can further include an EIL 556 between the third ETL 560 and the second electrode 364.

The third emitting part 550 can further include at least one of an EBL between the third HTL 552 and the third EML 554 and an HBL between the third EML 554 and the third ETL 560.

Each of the first and third EMLs 516 and 554 provides blue light, and the second EML 534 provides yellow-green light. For example, each of the first and third EMLs 516 and 554 can provide blue light and can include a host and a blue dopant. The second EML 534 can provide yellow-green light and can include a host and a yellow-green dopant. Alternatively, the second EML 534 can have a double-layered structure of a first layer emitting red light and a second layer emitting green light. In addition, the second EML 534 can have a triple-layered structure of a first layer including a host and a red dopant, a second layer including a host and a yellow-green dopant and a third layer including a host and a green dopant.

For example, in each of the first and third EMLs 516 and 554 emitting blue light, a host can be an anthracene derivative, and a blue dopant can be a pyrene derivative.

The first CGL 570 includes a first n-type CGL 572 and a first p-type CGL 574. The first n-type CGL 572 is positioned between the first ETL 520 and the second HTL 532, and the first p-type CGL 574 is positioned between the first n-type CGL 572 and the second HTL 532.

The second CGL 580 includes a second n-type CGL 582 and a second p-type CGL 584. The second n-type CGL 582 is positioned between the second ETL 540 and the third HTL 552, and the second p-type CGL 584 is positioned between the second n-type CGL 582 and the third HTL 552.

The first n-type CGL 572 provides the electron toward the first ETL 520, and the electron is transferred into the first EML 516 through the first ETL 520. The first p-type CGL 574 provides the hole toward the second HTL 532, and the hole is transferred into the second EML 534 through the second HTL 532.

The second n-type CGL 582 provides the electron toward the second ETL 540, and the electron is transferred into the second EML 534 through the second ETL 540. The second p-type CGL 584 provides the hole toward the third HTL 552, and the hole is transferred into the third EML 554 through the third HTL 552.

As a result, in the OLED D having a three-stack (triple-stack) structure, the driving voltage is reduced, and the emitting efficiency is improved.

For example, each of the first and second p-type CGLs 574 and 584 can include the compound in Formula 9-1 or 9-2. In addition, each of the first and second p-type CGLs 574 and 584 can further include metal or a p-type dopant.

At least one of the first ETL 520, the first n-type CGL 572, the second ETL 540, the second n-type CGL 582 and the third ETL 560 includes the organic compound in Formula 1-1. For example, the first ETL 520 can include the organic compound of the present disclosure as a first electron transporting material 522, the second ETL 540 can include the organic compound of the present disclosure as a second electron transporting material 542, and the third ETL 560 can include the organic compound of the present disclosure as a third electron transporting material 562. The first n-type CGL 572 can include the organic compound of the present disclosure as a first n-type charge generation material 576, and the second n-type CGL 582 can include the organic compound of the present disclosure as a second n-type charge generation material 586.

The first electron transporting material 522 in the first ETL 520, the second electron transporting material 542 in the second ETL 540, the third electron transporting material 562 in the third ETL 560, the first n-type charge generation material 576 in the first n-type CGL 572, and the second n-type charge generation material 586 in the second n-type CGL 582 can be same or different.

When each of the first and second n-type CGLs 572 and 582 include the organic compound as the first and second n-type charge generation materials 576 and 586, respectively, each of the first and second n-type CGLs 572 and 582 can further include an auxiliary n-type charge generation material. For example, the auxiliary n-type charge generation material can be alkali metal, e.g., Li, Cs, K, Rb, Na or Fr, or alkali earth metal, e.g., Be, Mg, Ca, Sr, Ba or Ra. In each of the first and second n-type CGLs 572 and 582, the auxiliary n-type charge generation material can have a weight % of about 0.1 to 10, preferably about 0.5 to 5.

The OLED D including the first and third emitting parts 510 and 550 each providing blue light and the second emitting part 530 providing yellow-green light provides the white emission, and the first and second CGLs 570 and 580 is provided between the first and second emitting parts 510 and 530 and between the second and third emitting parts 530 and 550, respectively. As a result, the OLED D has advantages in the driving voltage, the emitting efficiency and the lifespan.

Referring to FIG. 4 again, a second electrode 364 is formed over the substrate 310 where the organic emitting layer 362 is formed.

In the organic light emitting display device 300, since the light emitted from the organic emitting layer 362 is incident to the color filter layer 380 through the second electrode 364, the second electrode 364 has a thin profile for transmitting the light.

The first electrode 360, the organic emitting layer 362 and the second electrode 364 constitute the OLED D.

The color filter layer 380 is positioned over the OLED D and includes a red color filter 382, a green color filter 384 and a blue color filter 386 respectively corresponding to the red, green and blue pixels RP, GP and BP. The red color filter 382 can include at least one of red dye and red pigment, the green color filter 384 can include at least one of green dye and green pigment, and the blue color filter 386 can include at least one of blue dye and blue pigment.

The color filter layer 380 can be attached to the OLED D by using an adhesive layer. Alternatively, the color filter layer 380 can be formed directly on the OLED D.

An encapsulation film can be formed to prevent penetration of moisture into the OLED D. For example, the encapsulation film can include a first inorganic insulating layer, an organic insulating layer and a second inorganic insulating layer sequentially stacked, but it is not limited thereto. The encapsulation film can be omitted.

A polarization plate for reducing an ambient light reflection can be disposed over the top-emission type OLED D. For example, the polarization plate can be a circular polarization plate.

In the OLED of FIG. 4, the first and second electrodes 360 and 364 are a reflection electrode and a transparent (or semi-transparent) electrode, respectively, and the color filter layer 380 is disposed over the OLED D. Alternatively, when the first and second electrodes 360 and 364 are a transparent (or semi-transparent) electrode and a reflection electrode, respectively, the color filter layer 380 can be disposed between the OLED D and the first substrate 310.

A color conversion layer can be formed between the OLED D and the color filter layer 380. The color conversion layer can include a red color conversion layer, a green color conversion layer and a blue color conversion layer respectively corresponding to the red, green and blue pixels RP, GP and BP. The white light from the OLED D is converted into the red light, the green light and the blue light by the red, green and blue color conversion layer, respectively. For example, the color conversion layer can include a quantum dot. Accordingly, the color purity of the organic light emitting display device 300 can be further improved.

The color conversion layer can be included instead of the color filter layer 380.

As described above, in the organic light emitting display device 300, the OLED D in the red, green and blue pixels RP, GP and BP emits the white light, and the white light from the organic light emitting diode D passes through the red color filter 382, the green color filter 384 and the blue color filter 386. As a result, the red light, the green light and the blue light are provided from the red pixel RP, the green pixel GP and the blue pixel BP, respectively.

In FIG. 4, the OLED D emitting the white light is used for a display device. Alternatively, the OLED D can be formed on an entire surface of a substrate without at least one of the driving element and the color filter layer to be used for a lightening device. The display device and the lightening device each including the OLED D of the present disclosure can be referred to as an organic light emitting device.

In the OLED D and the organic light emitting display device 300, at least one of the ETL and the n-type CGL includes the organic compound of the present disclosure such that the electron transporting property (efficiency) toward the EML is improved. Accordingly, in the OLED and the display device 300, the driving voltage is decreased, and the emitting efficiency and the lifespan are increased.

It will be apparent to those skilled in the art that various modifications and variations can be made in the embodiments of the present disclosure without departing from the spirit or scope of the present disclosure. Thus, it is intended that the modifications and variations cover this disclosure provided they come within the scope of the appended claims and their equivalents.

What is claimed is:

1. An organic compound in Formula 1-1:

[Formula 1-1]

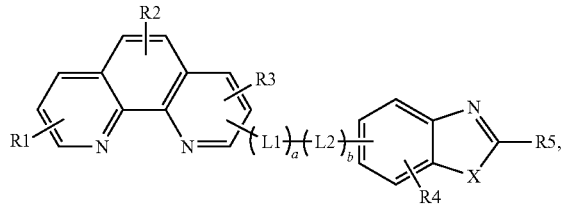

wherein X is oxygen or sulfur, and each of R1 to R4 is independently selected from the group consisting of hydrogen (H), deuterium (D), C1 to C10 alkyl group, C1 to C10 alkoxy group, C3 to C30 cycloalkyl group, C6 to C30 aryl group, C6 to C30 arylamino group and C5 to C30 heteroaryl group unsubstituted or substituted with phenyl, wherein R5 is selected from the group consisting of C1 to C10 alkyl group, C1 to C10 alkoxy group, C3 to C30 cycloalkyl group, C6 to C30 aryl group, C6 to C30 arylamino group and C5 to C30 heteroaryl group unsubstituted or substituted with phenyl, and wherein each of L1 and L2 is independently selected from the group consisting of C6 to C30 arylene group and C5 to C30 heteroarylene group, and each of a and b is 0 or 1.

2. The organic compound according to claim 1, wherein the organic compound is represented by Formula 1-2:

[Formula 1-2]

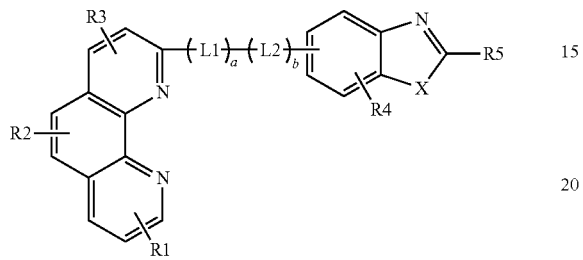

wherein each of X, R1, R2, R3, R4, R5, L1 and L2 is identical as defined in Formula 1-1, and each of a and b is 0 or 1.

3. The organic compound according to claim 1, wherein the organic compound is one of compounds in Formula 2:

[Formula 2]

C1

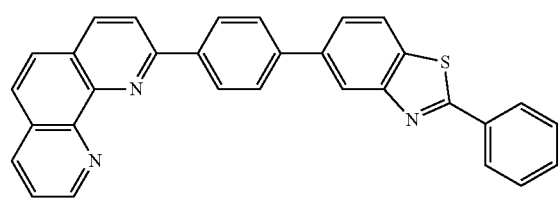

C2

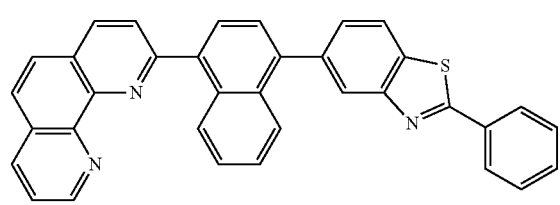

C3

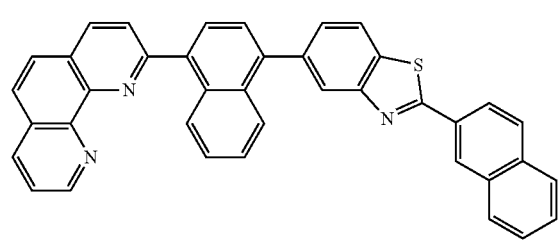

-continued

C4

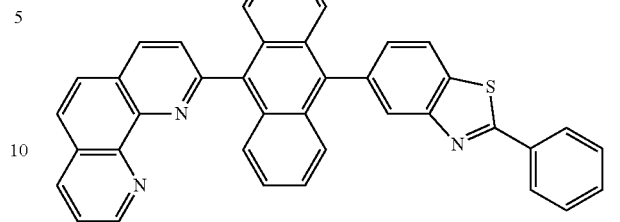

C5

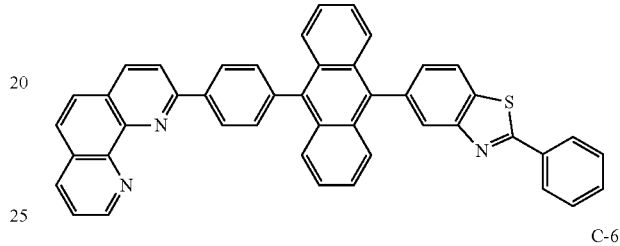

C-6

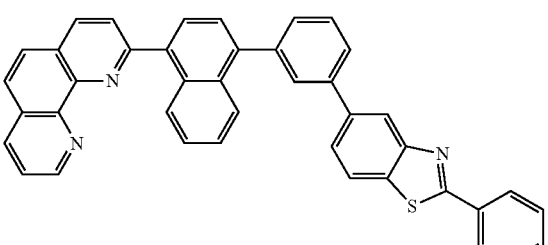

C7

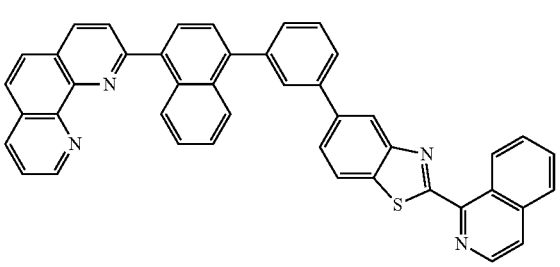

C8

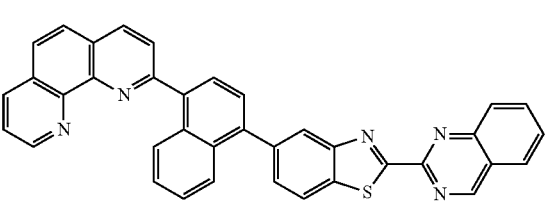

C9

C10
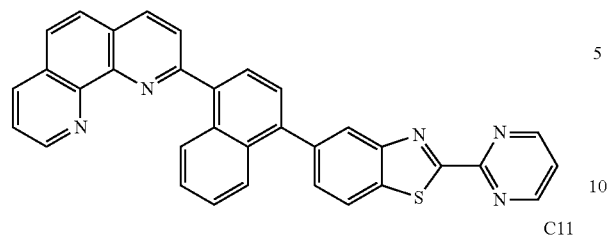
C11
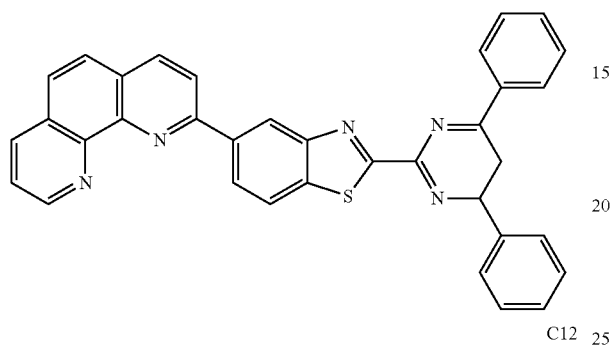
C12
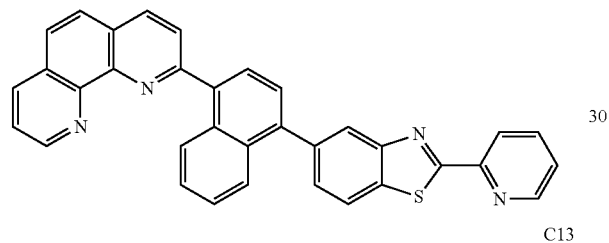
C13
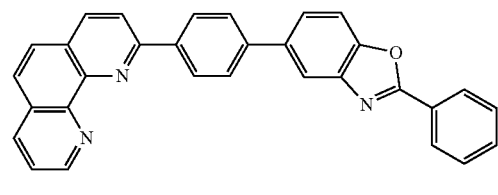
C14
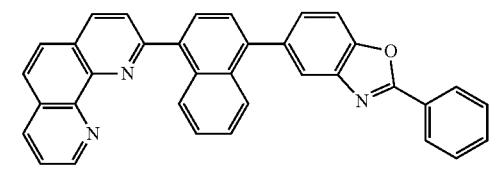
C15
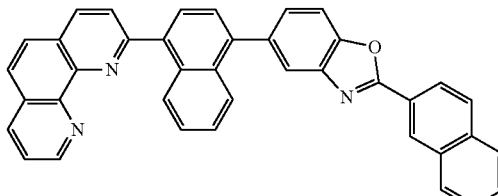
C16
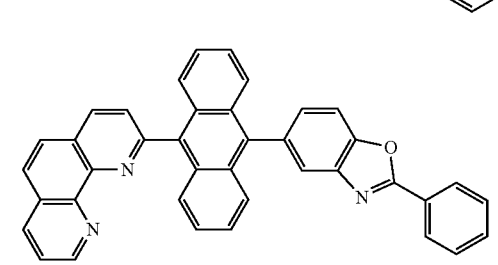
C17
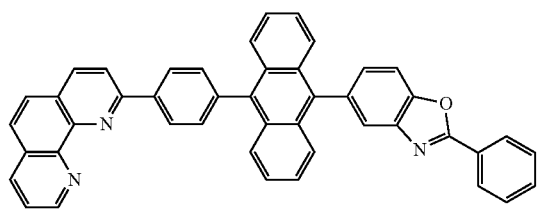
C18
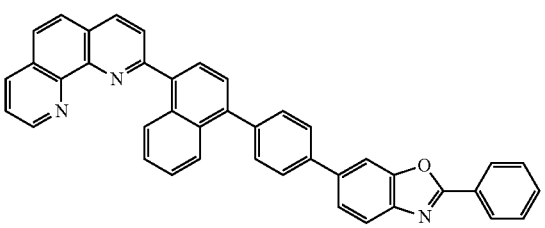
C19
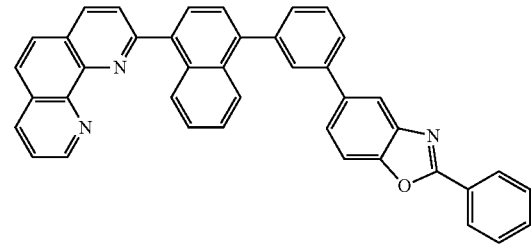
C20
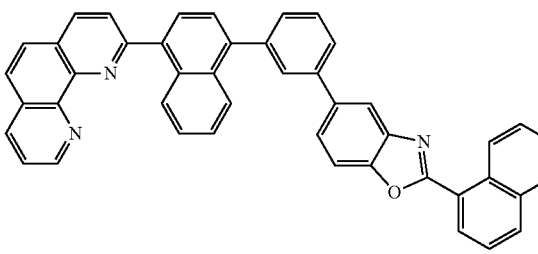
C21
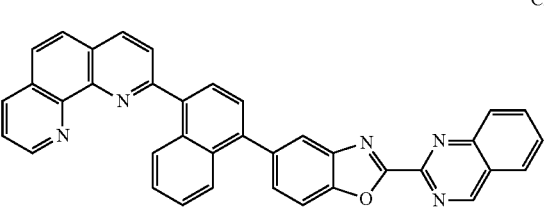
C22
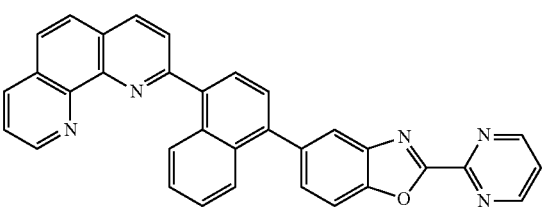

-continued

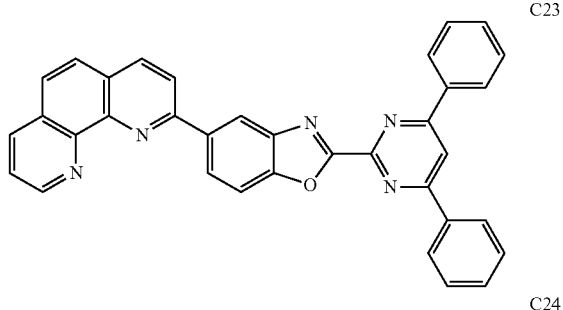

C23

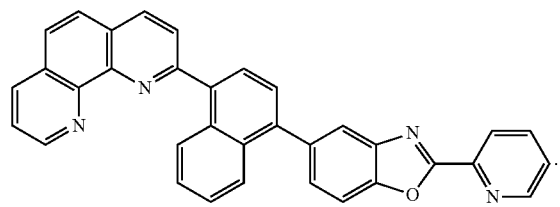

C24

4. An organic light emitting diode, comprising:
a first electrode;
a second electrode facing the first electrode; and
a first emitting part including a first emitting material layer and a first electron transporting layer and positioned between the first and second electrodes,
wherein the first electron transporting layer is positioned between the first emitting material layer and the second electrode and includes a first electron transporting material,
wherein the first electron transporting material is an organic compound in Formula 1-1:

[Formula 1-1]

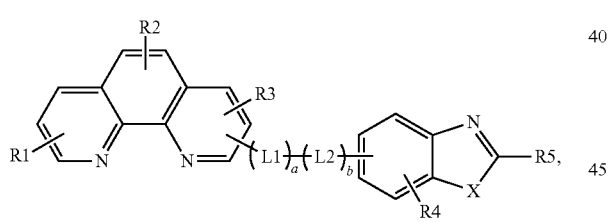

wherein X is oxygen or sulfur, and each of R1 to R4 is independently selected from the group consisting of hydrogen (H), deuterium (D), C1 to C10 alkyl group, C1 to C10 alkoxy group, C3 to C30 cycloalkyl group, C6 to C30 aryl group, C6 to C30 arylamino group and C5 to C30 heteroaryl group unsubstituted or substituted with phenyl,
wherein R5 is selected from the group consisting of C1 to C10 alkyl group, C1 to C10 alkoxy group, C3 to C30 cycloalkyl group, C6 to C30 aryl group, C6 to C30 arylamino group and C5 to C30 heteroaryl group unsubstituted or substituted with phenyl, and
wherein each of L1 and L2 is independently selected from the group consisting of C6 to C30 arylene group and C5 to C30 heteroarylene group, and each of a and b is 0 or 1.

5. The organic light emitting diode according to claim 4, wherein the organic compound is represented by Formula 1-2:

[Formula 1-2]

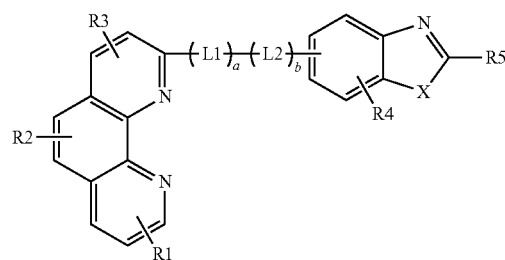

wherein each of X, R1, R2, R3, R4, R5, L1 and L2 is identical as defined in Formula 1-1, and each of a and b is 0 or 1.

6. The organic light emitting diode according to claim 4, wherein the organic compound is one of compounds in Formula 2:

[Formula 2]

C1

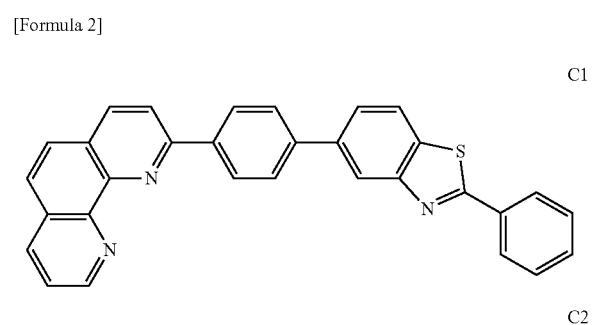

C2

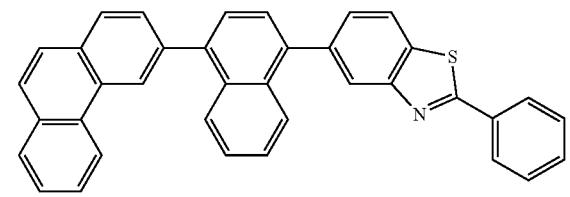

C3

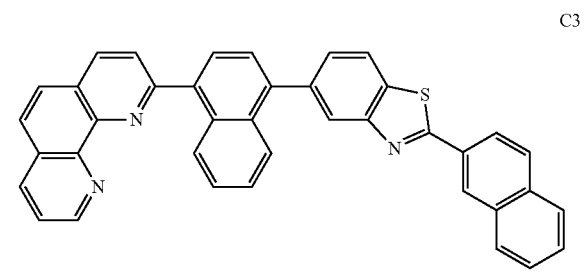

C4

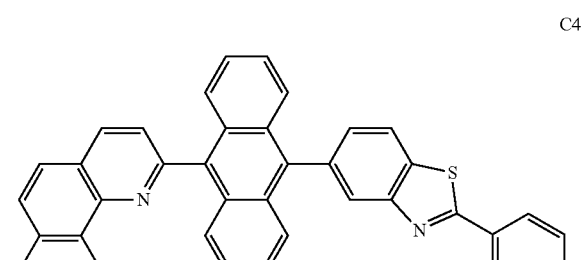
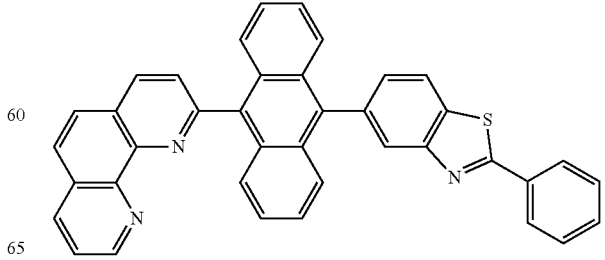

C5
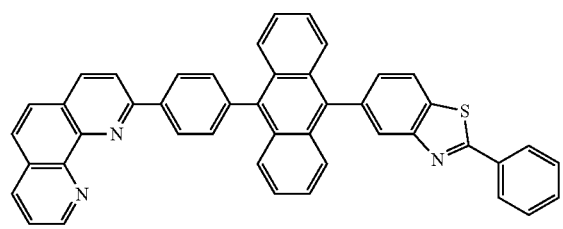
C-6
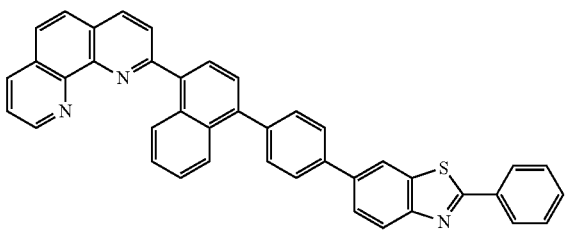
C7
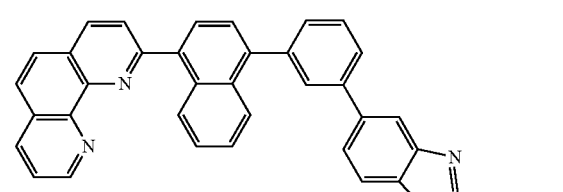
C8
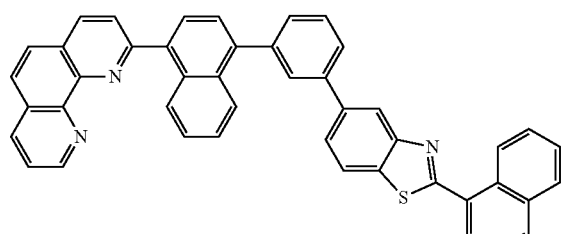
C9
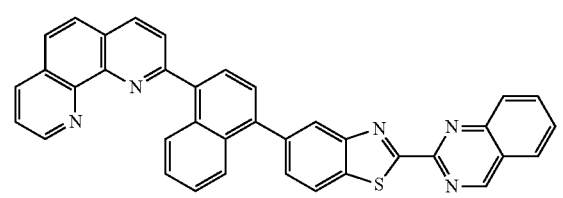
C10
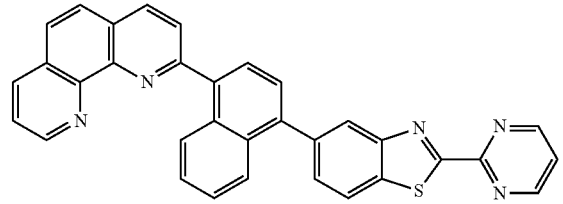
C11
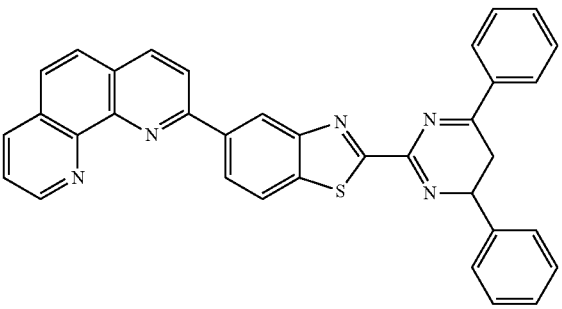
C12
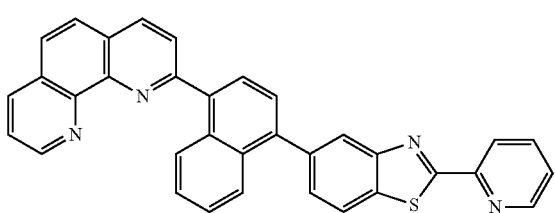
C13
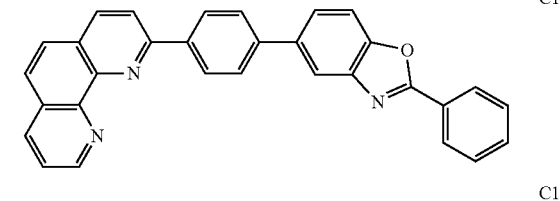
C14
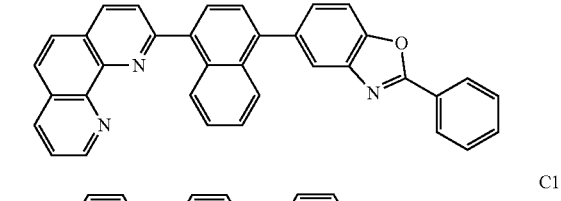
C15
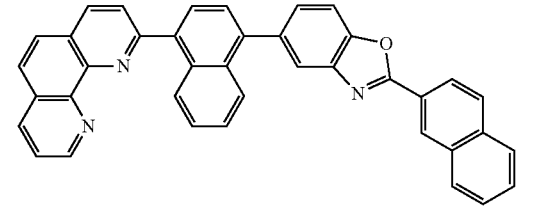
C16
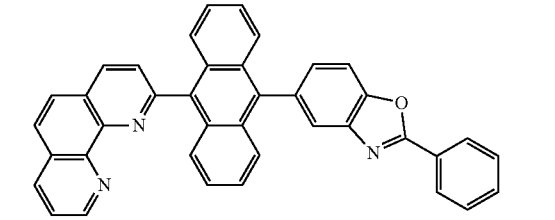
C17
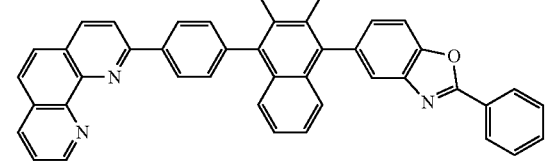

-continued

C18
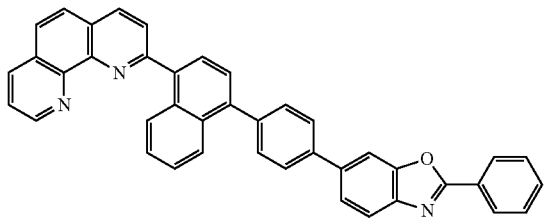

C19
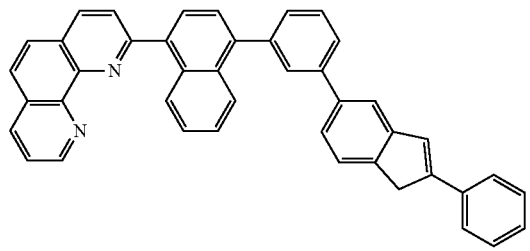

C20
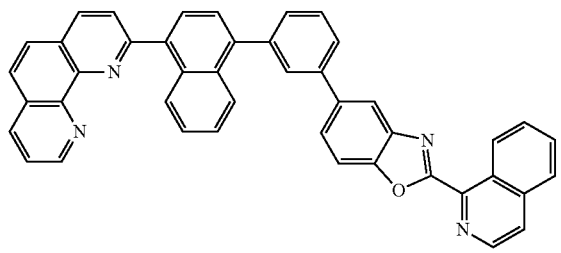

C21
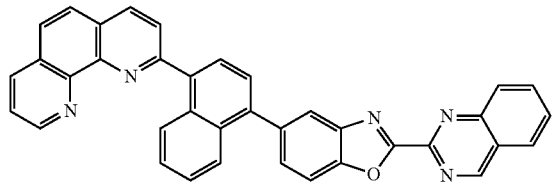

C22
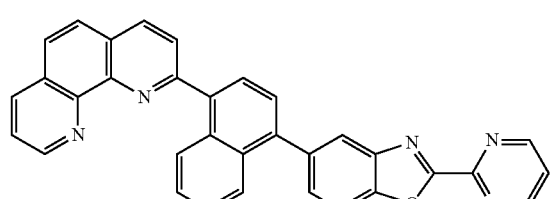

C23
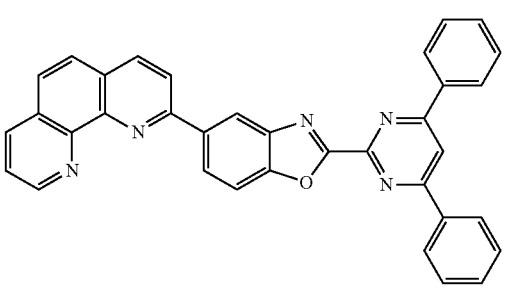

-continued

C24
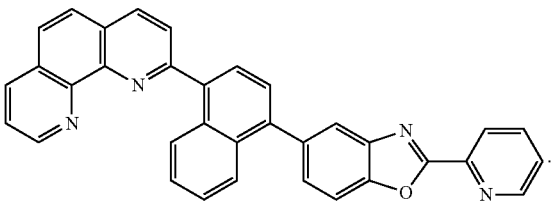

7. The organic light emitting diode according to claim 4, further comprising:
a second emitting part including a second emitting material layer and a second electron transporting layer and positioned between the first emitting part and the second electrode; and
a first n-type charge generation layer including a first n-type charge generation material and positioned between the first and second emitting parts,
wherein the second electron transporting layer is positioned between the second emitting material layer and the second electrode and includes a second electron transporting material.

8. The organic light emitting diode according to claim 7, wherein at least one of the second electron transporting material and the first n-type charge generation material is the organic compound in Formula 1-1.

9. The organic light emitting diode according to claim 7, wherein the first emitting material layer provides a blue light, and the second emitting material layer provides a yellow-green light.

10. The organic light emitting diode according to claim 7, wherein the first emitting material layer provides a blue light, and the second emitting material layer includes a first layer providing a red light and a second layer providing a green light.

11. The organic light emitting diode according to claim 7, further comprising:
a third emitting part including a third emitting material layer and a third electron transporting layer and positioned between the second emitting part and the second electrode; and
a second n-type charge generation layer including a second n-type charge generation material and positioned between the second and third emitting parts,
wherein the third electron transporting layer is positioned between the third emitting material layer and the second electrode and includes a third electron transporting material.

12. The organic light emitting diode according to claim 11, wherein at least one of the second electron transporting material, the third electron transporting material, the first n-type charge generation material and the second n-type charge generation material is the organic compound in Formula 1-1.

13. The organic light emitting diode according to claim 11, wherein each of the first and third emitting material layer provides a blue light, and the second emitting material layer includes a first layer providing a red light and a second layer providing a green light.

14. An organic light emitting diode, comprising:
a first electrode;
a second electrode facing the first electrode;

a first emitting part including a first emitting material layer and positioned between the first and second electrodes;

a second emitting part including a second emitting material layer and positioned between the first emitting part and the second electrode; and a first n-type charge generation layer including a first n-type charge generation material and positioned between the first and second emitting parts, wherein the first n-type charge generation material is an organic compound in Formula 1-1:

[Formula 1-1]

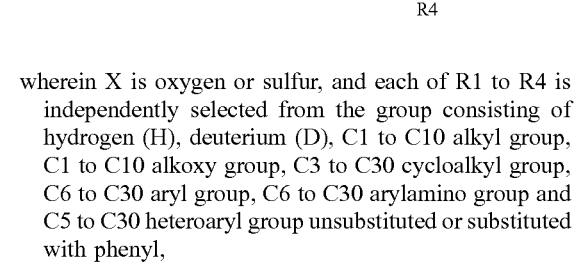

wherein X is oxygen or sulfur, and each of R1 to R4 is independently selected from the group consisting of hydrogen (H), deuterium (D), C1 to C10 alkyl group, C1 to C10 alkoxy group, C3 to C30 cycloalkyl group, C6 to C30 aryl group, C6 to C30 arylamino group and C5 to C30 heteroaryl group unsubstituted or substituted with phenyl, wherein R5 is selected from the group consisting of C1 to C10 alkyl group, C1 to C10 alkoxy group, C3 to C30 cycloalkyl group, C6 to C30 aryl group, C6 to C30 arylamino group and C5 to C30 heteroaryl group unsubstituted or substituted with phenyl, and wherein each of L1 and L2 is independently selected from the group consisting of C6 to C30 arylene group and C5 to C30 heteroarylene group, and each of a and b is 0 or 1.

15. The organic light emitting diode according to claim 14, wherein the organic compound is represented by Formula 1-2:

[Formula 1-2]

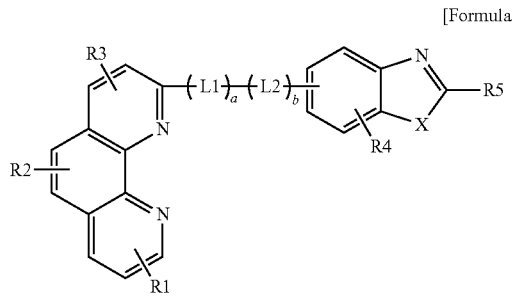

wherein each of X, R1, R2, R3, R4, R5, L1 and L2 is identical as defined in Formula 1-1, and each of a and b is 0 or 1.

16. The organic light emitting diode according to claim 14, wherein the organic compound is one of compounds in Formula 2:

[Formula 2]

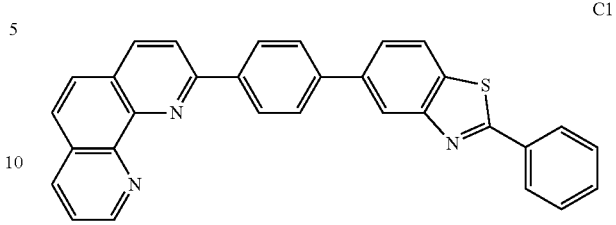
C1

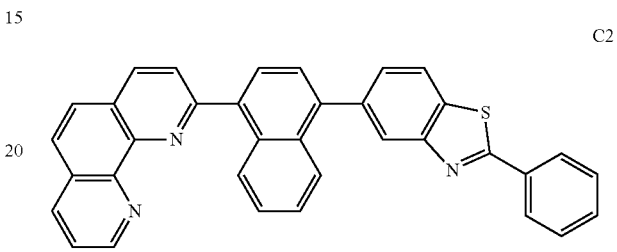
C2

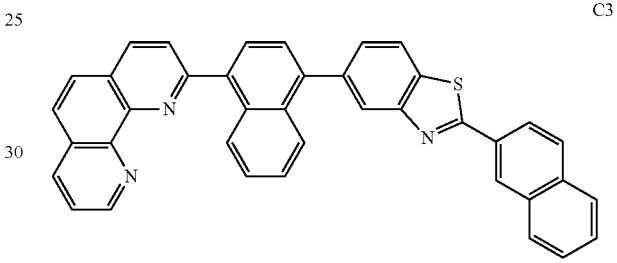
C3

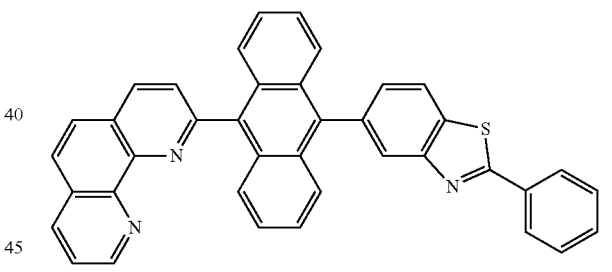
C4

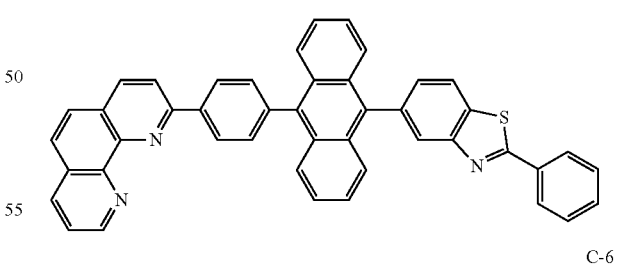
C5

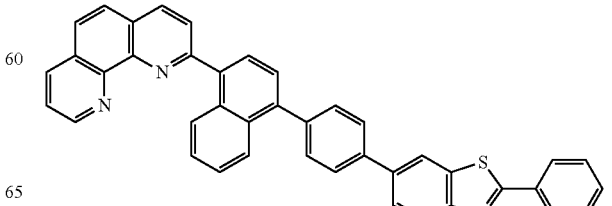
C-6

C7
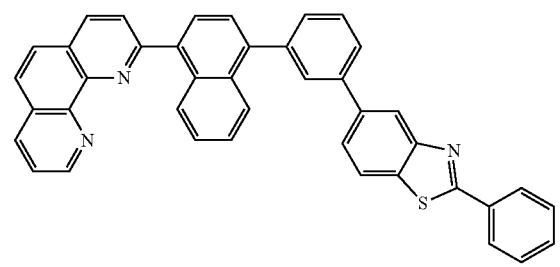
C8
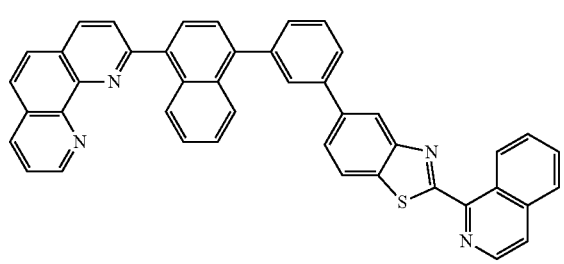
C9
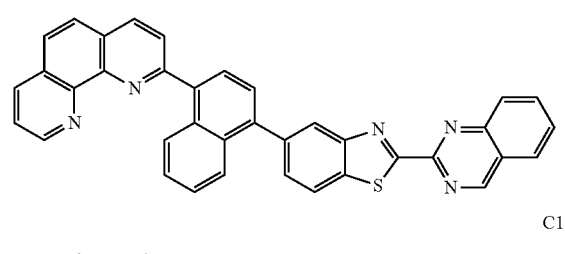
C10
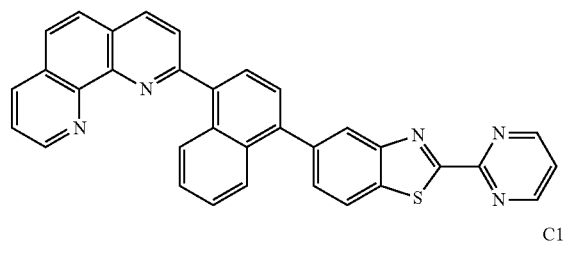
C11
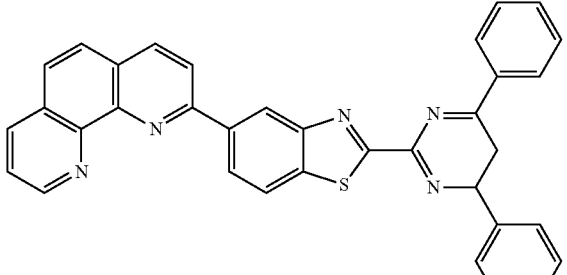
C12
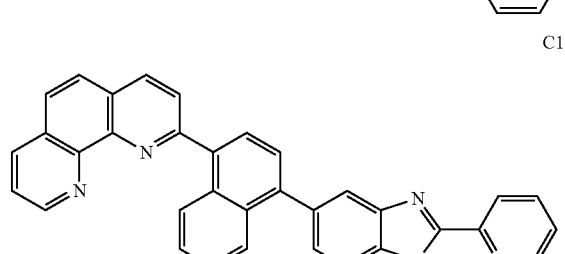
C13
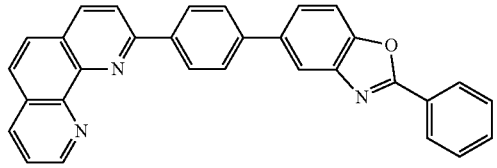
C14
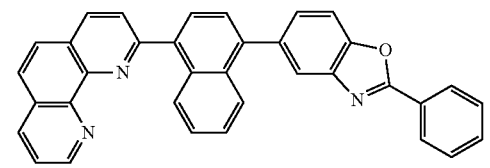
C15
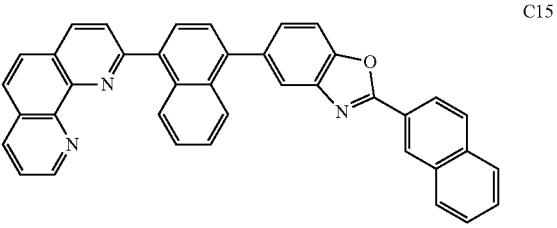
C16
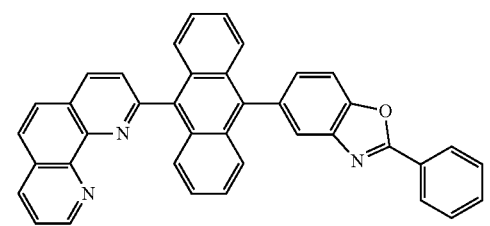
C17
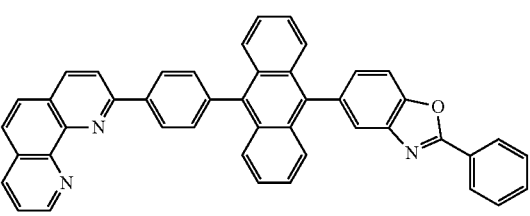
C18
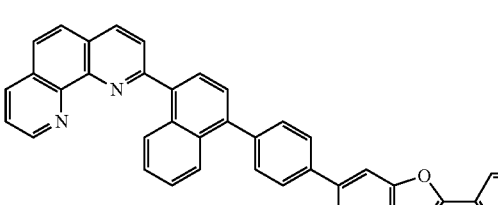
C19
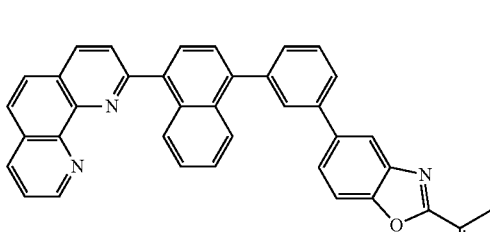

-continued

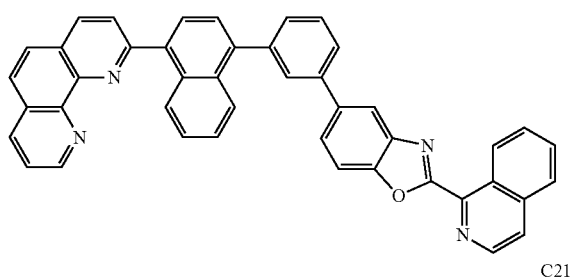
C20

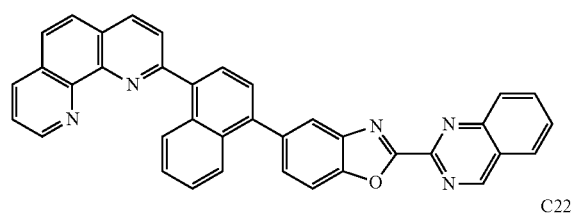
C21

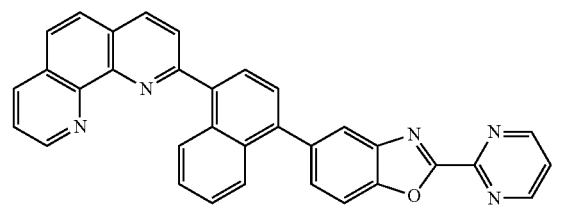
C22

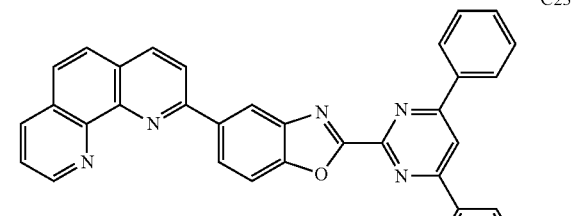
C23

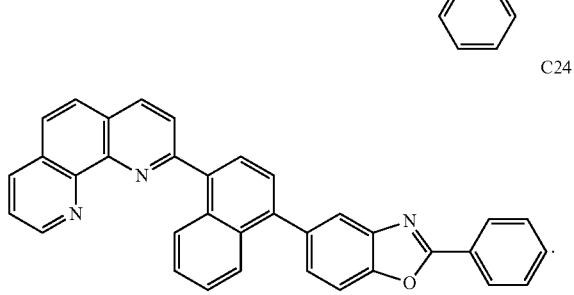
C24

17. The organic light emitting diode according to claim 14, wherein the first n-type charge generation layer further includes an alkali metal or an alkali earth metal.

18. The organic light emitting diode according to claim 17, wherein the alkali metal or the alkali earth metal has a weight % of approximately 0.1 to 10.

19. The organic light emitting diode according to claim 14, further comprising:
   a third emitting part including a third emitting material layer and positioned between the second emitting part and the second electrode; and
   a second n-type charge generation layer including a second n-type charge generation material and positioned between the second and third emitting parts.

20. The organic light emitting diode according to claim 19, wherein the second n-type charge generation material is the organic compound in Formula 1-1.

21. An organic light emitting device, comprising:
   a substrate;
   the organic light emitting diode of claim 4 and positioned on the substrate; and
   an encapsulation film covering the organic light emitting diode.

22. An organic light emitting device, comprising:
   a substrate;
   the organic light emitting diode of claim 14 and positioned on the substrate; and
   an encapsulation film covering the organic light emitting diode.

23. The organic compound according to claim 1, wherein R5 is selected from C6 to C30 aryl group.

24. The organic compound according to claim 23, wherein the organic compound is one of compounds in Formula 2:

[Formula 2]

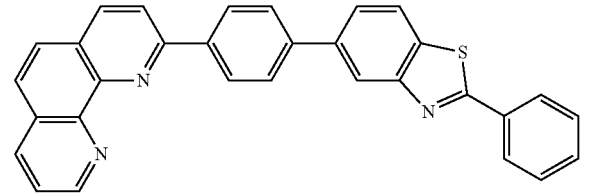
C1

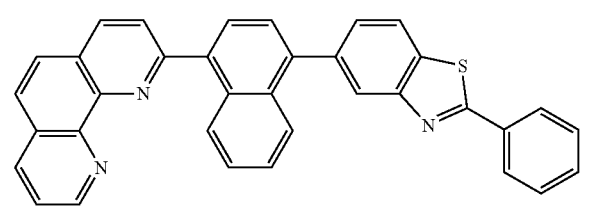
C2

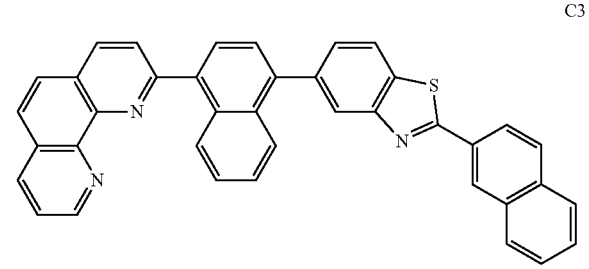
C3

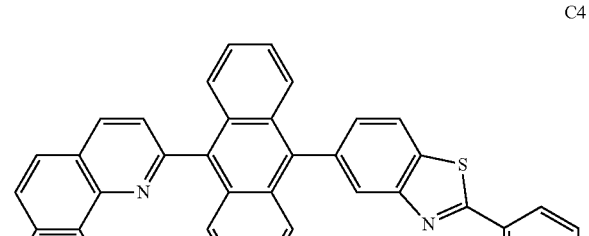
C4

C5
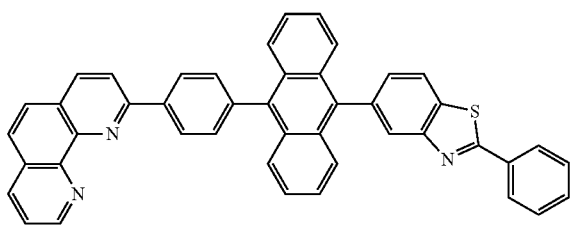
C6
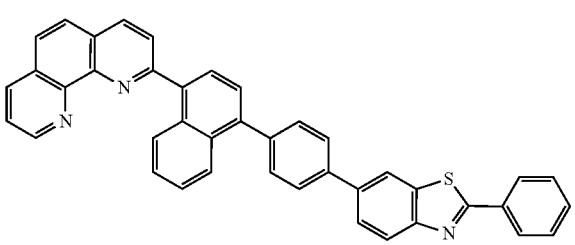
C7
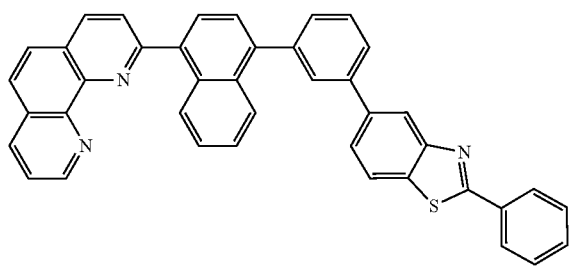
C13
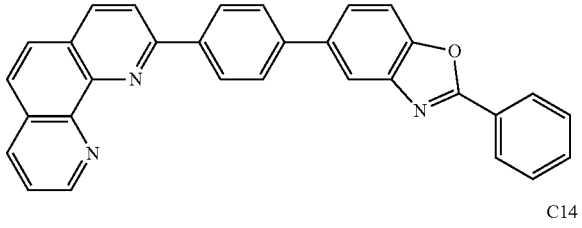
C14
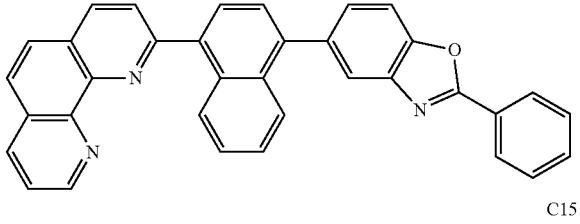
C15
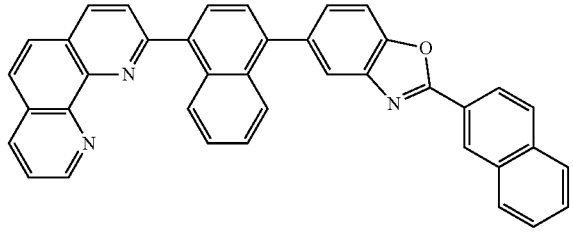
C16
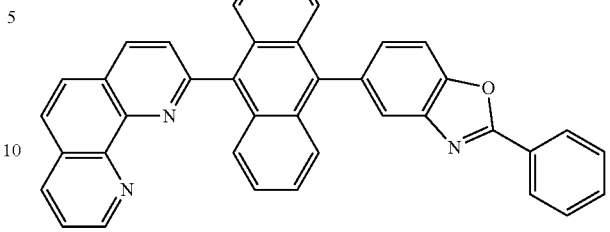
C17
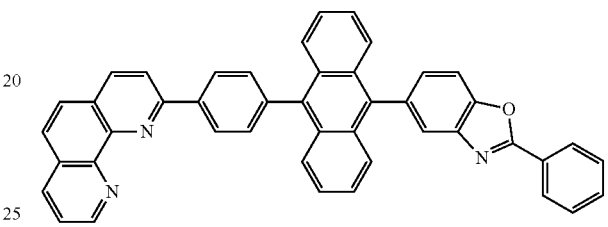
C18
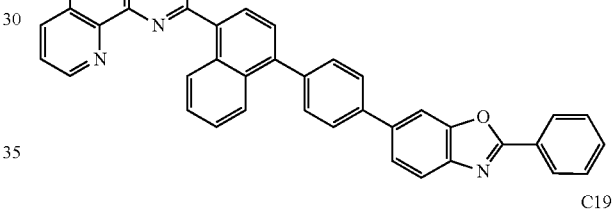
C19
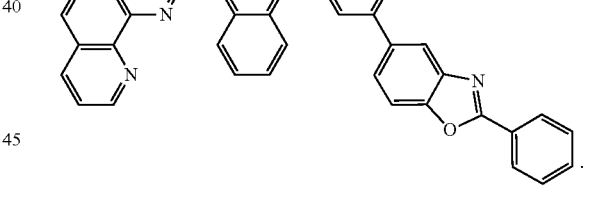
25. The organic light emitting diode according to claim 4, wherein R5 is selected from C6 to C30 aryl group.
26. The organic light emitting diode according to claim 25, wherein the organic compound is one of compounds in Formula 2:
[Formula 2]
C1
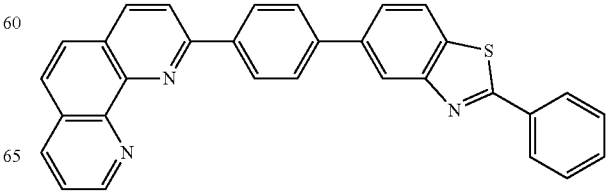

C2
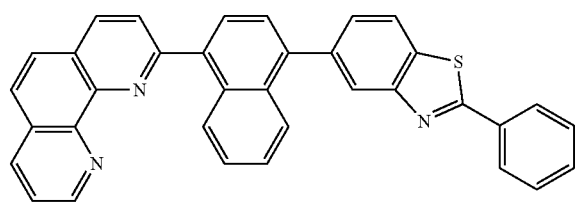
C3
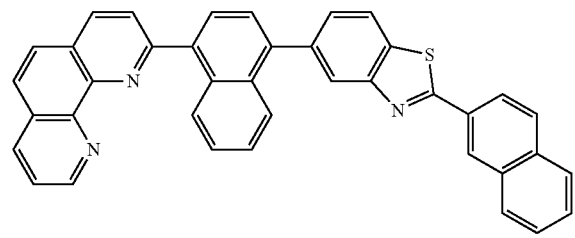
C4
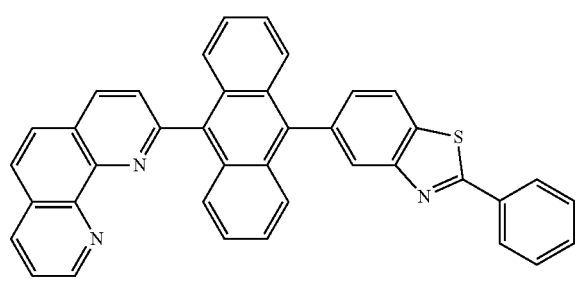
C5
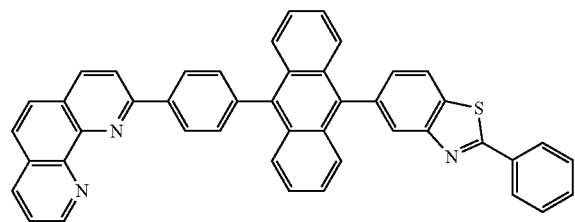
C6
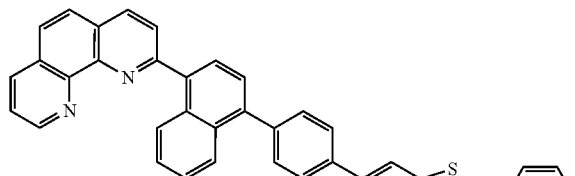
C7
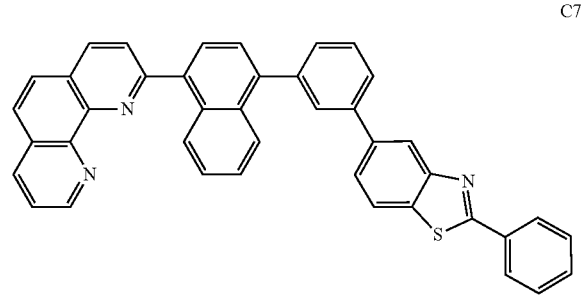
C13
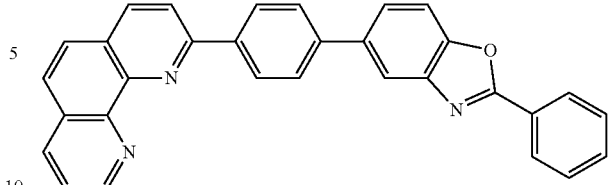
C14
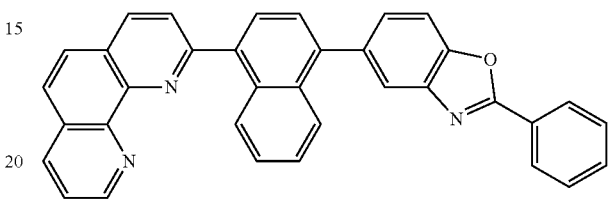
C15
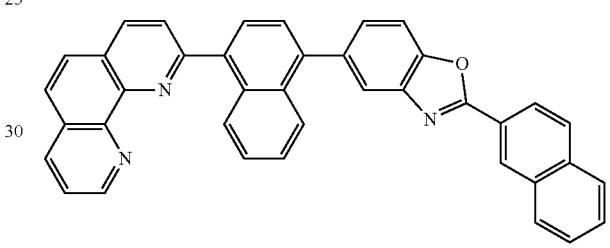
C16
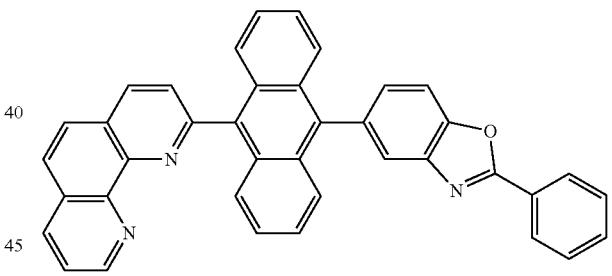
C17
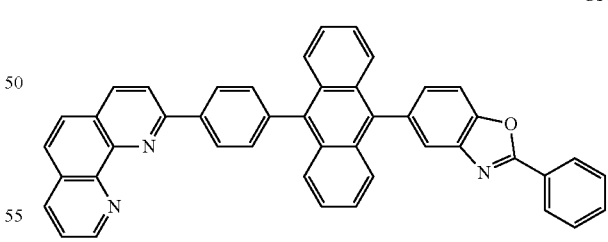
C18
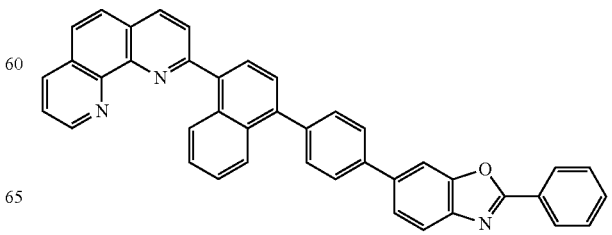

-continued

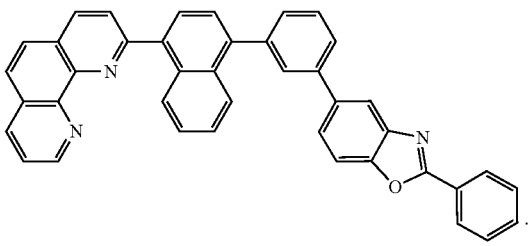
C19

27. The organic light emitting diode according to claim 14, further comprising:
  a first p-type charge generation layer including a p-type charge generation material and positioned between the first n-type charge generation layer and the second emitting part,
  wherein the p-type charge generation material is represented by p-type charge generation material:

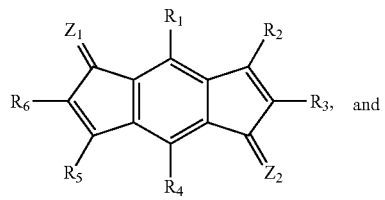
[Formula 9-1]

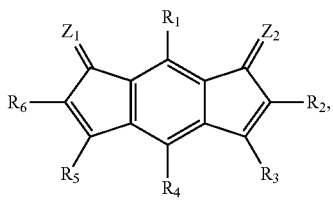
[Formula 9-2]

wherein each of $R_1$ to $R_6$ is independently selected from the group consisting of H, C6 to C30 aryl group, C6 to C30 heteroaryl group, C1 to C12 alkyl group, C1 to C12 alkoxy group, C2 to C12 ether group, cyano, fluorine, trifluoromethyl, trifluoromethoxy and trimethylsilyl, and at least one of $R_1$ to $R_6$ is cyano,
wherein each of Z1 and Z2 is independently represented by Formula 10:

[Formula 10]

wherein each of A and B is independently selected from the group consisting of H, C6 to C30 aryl group, C6 to C30 heteroaryl group, C1 to C12 alkyl group, C1 to C12 alkoxy group, C2 to C12 ether group, cyano, fluorine, trifluoromethyl, trifluoromethoxy and trimethylsilyl, and wherein Formula 10 attaches to the structure of Formula 9-1 or 9-2 at a carbon between A and B of Formula 10 through a double bond of Formula 9-1 or 9-2.

28. The organic light emitting diode according to claim 27, wherein the p-type charge generation material is one of compounds in Formula 11:

[Formula 11]

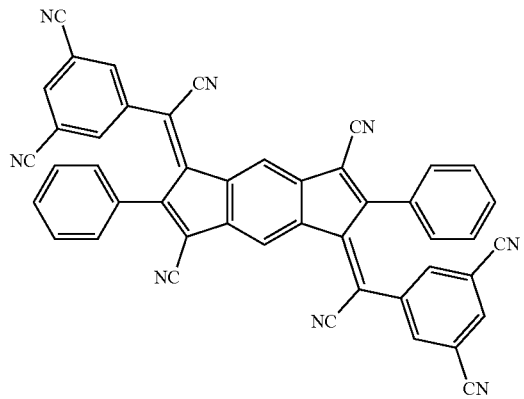
A01

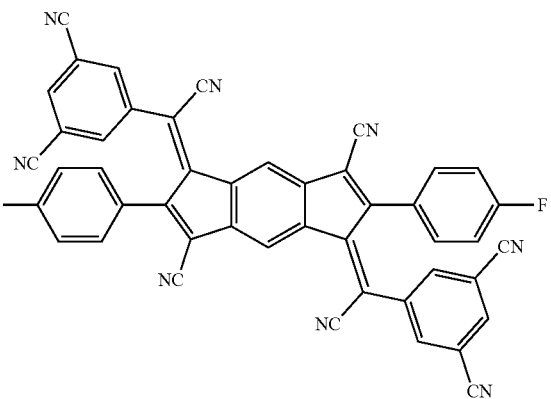
A02

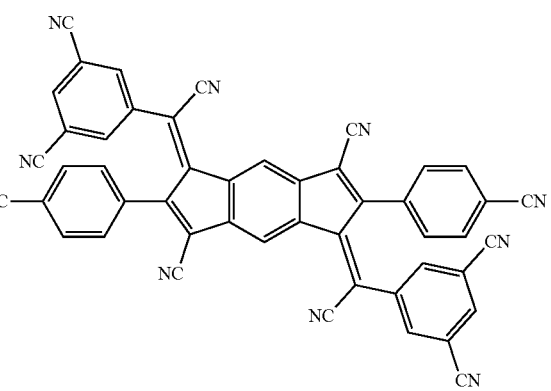
A03

-continued
A04
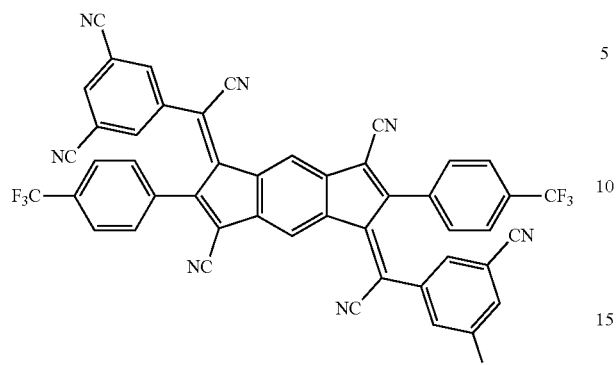
A05
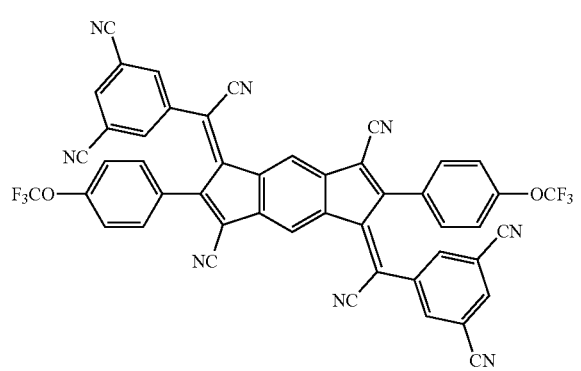
A06
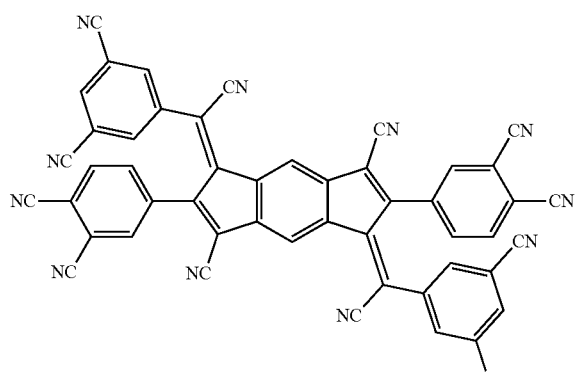
A07
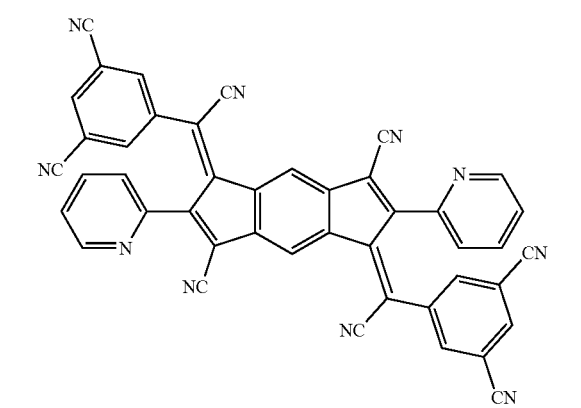
-continued
A08
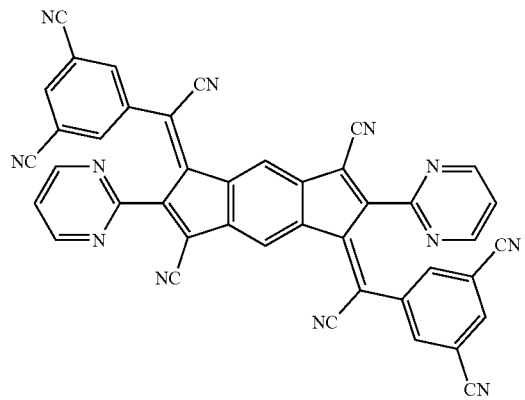
A09
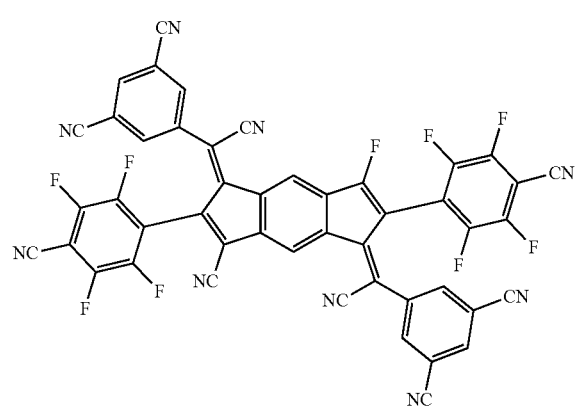
A10
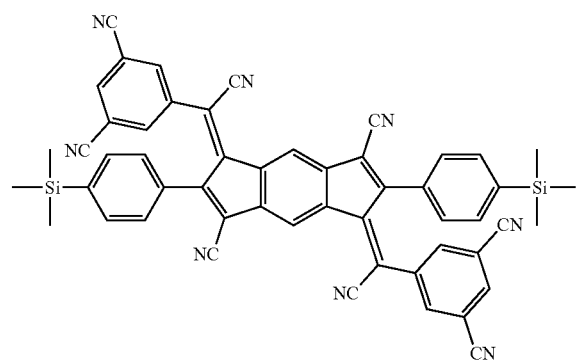
A11
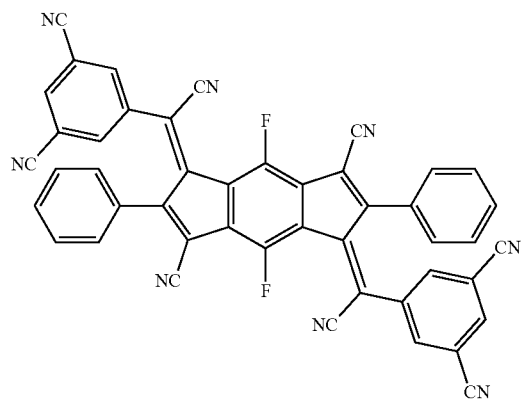

-continued
A12
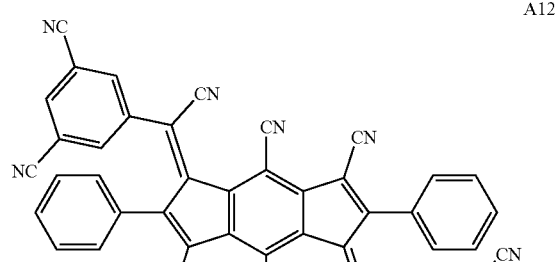
A13
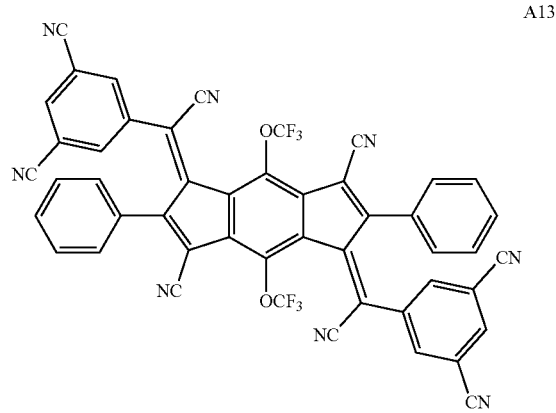
A14
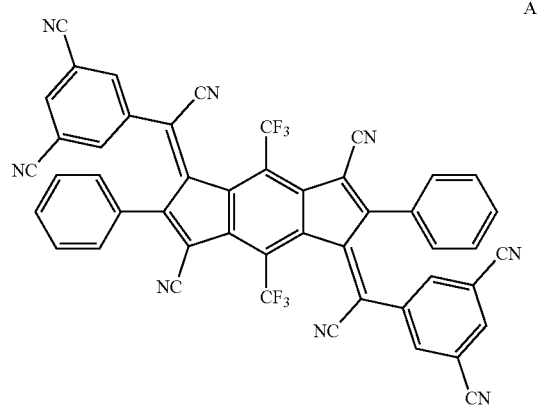
A15
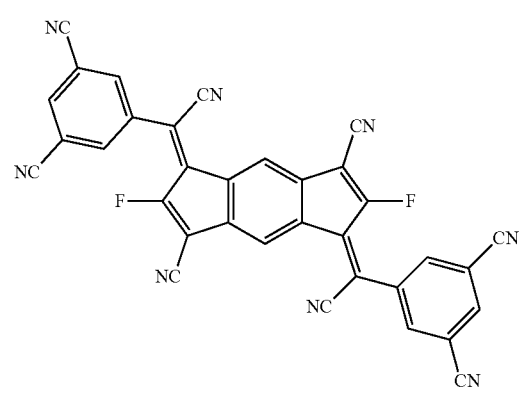
-continued
A16
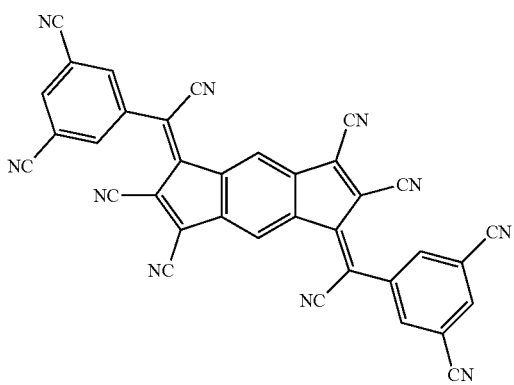
A17
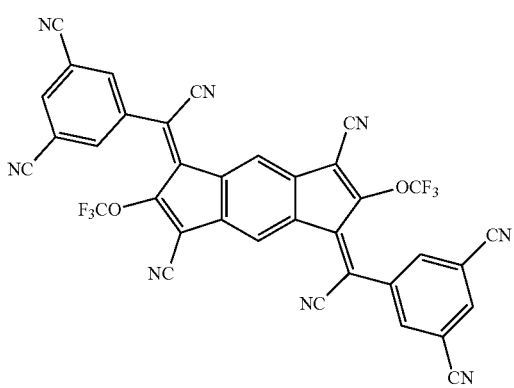
A18
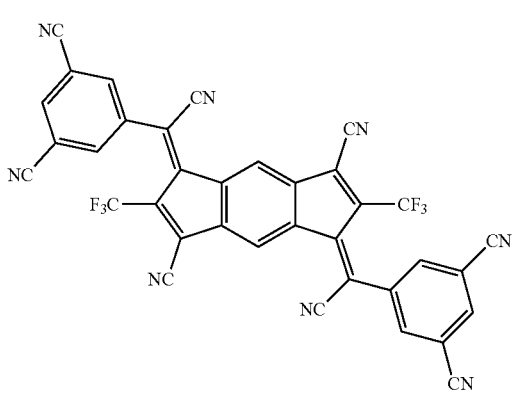
A19
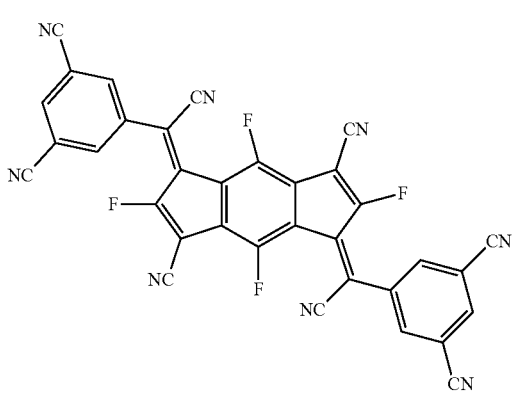

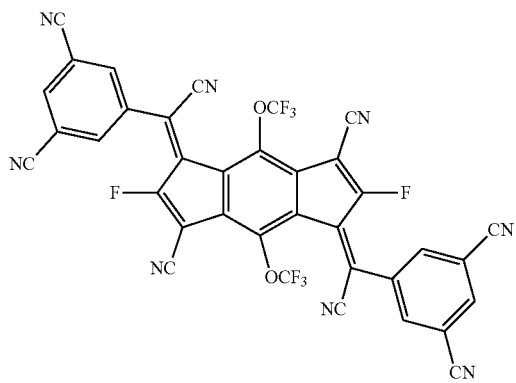
A20
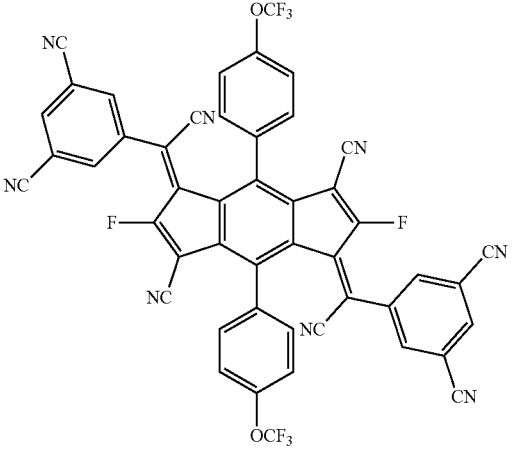
A23
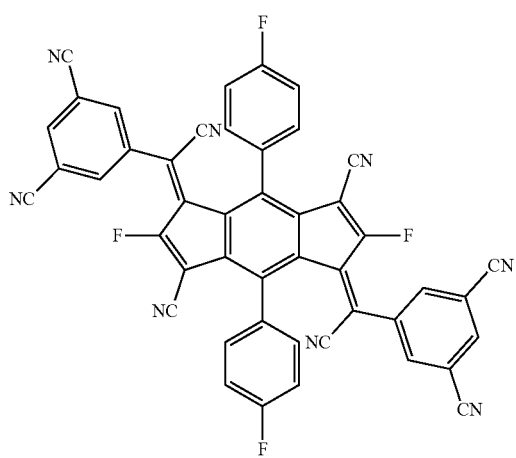
A21
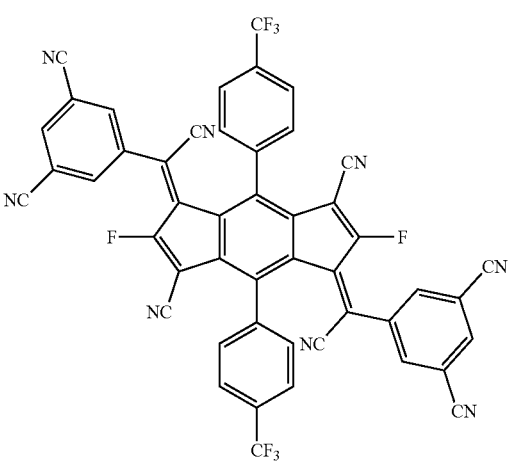
A24
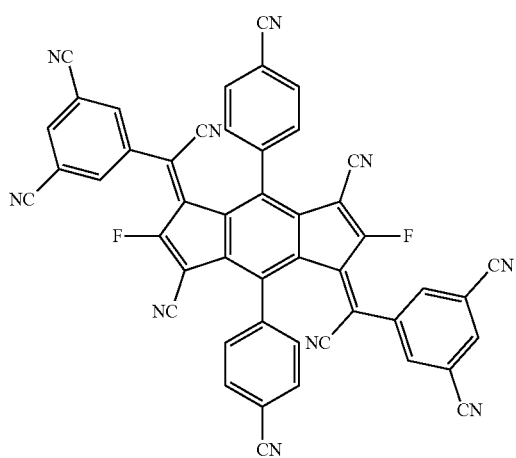
A22
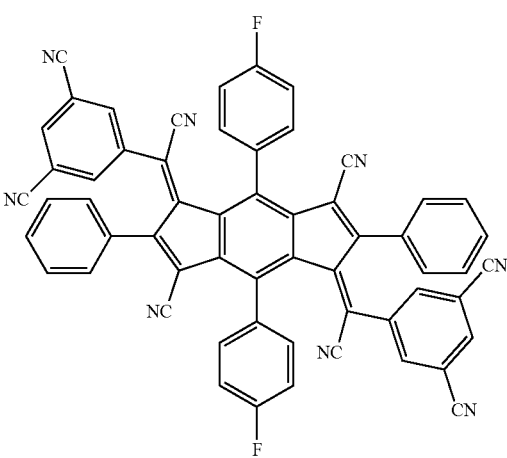
A25

-continued
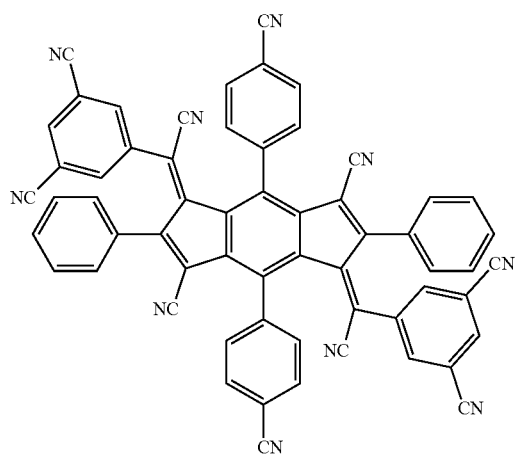
A26
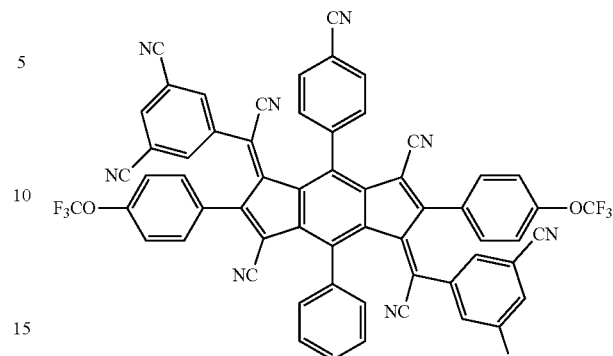
A29
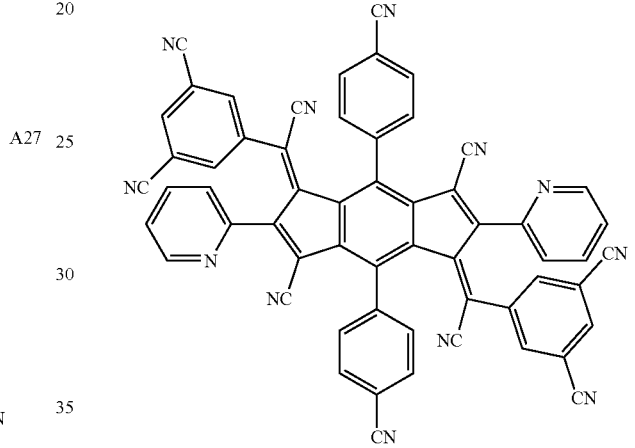
A30
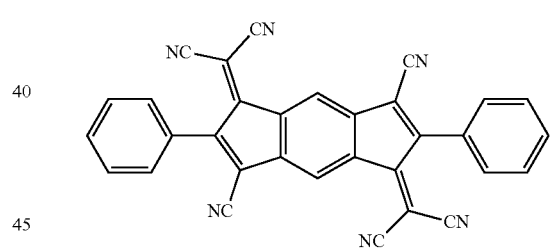
A31
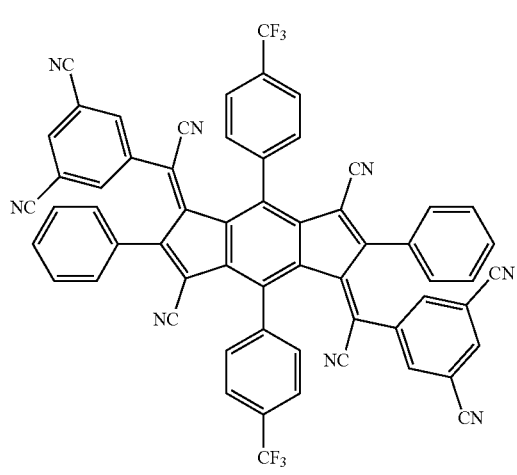
A27
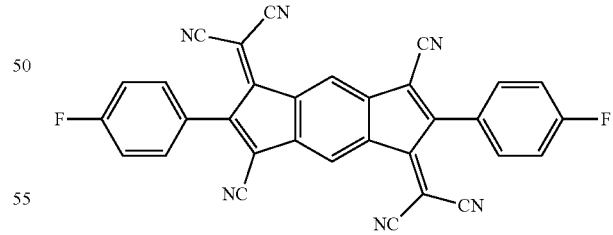
A32
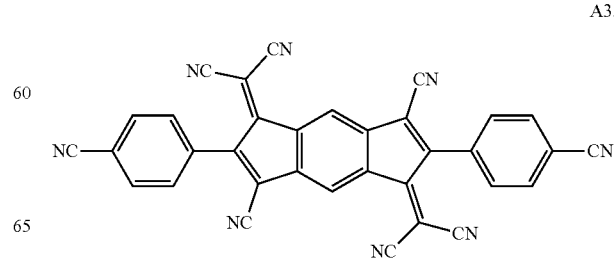
A33
A28

-continued
A34
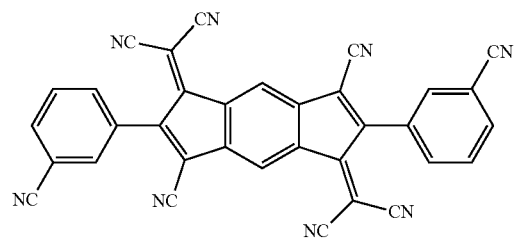
A35
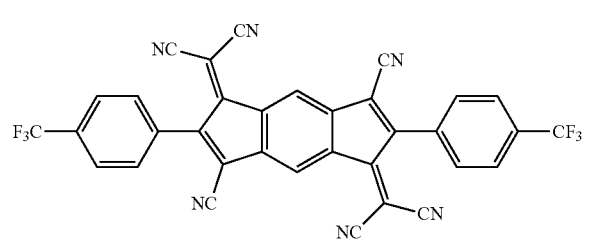
A36
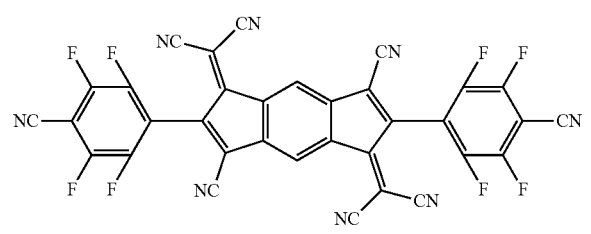
A37
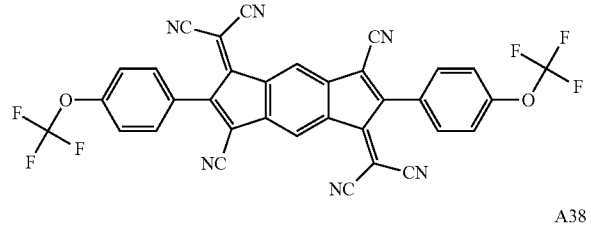
A38
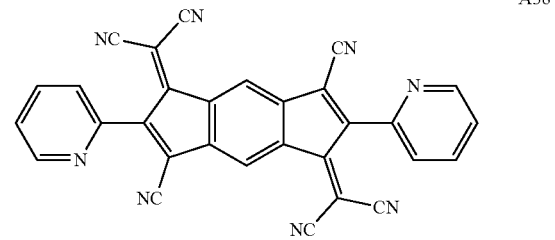
A39
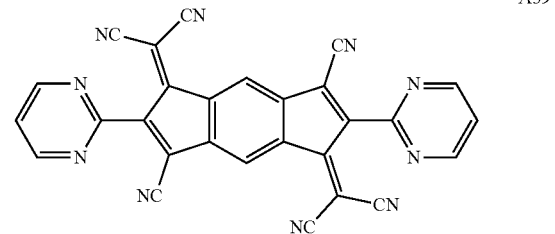
-continued
A40
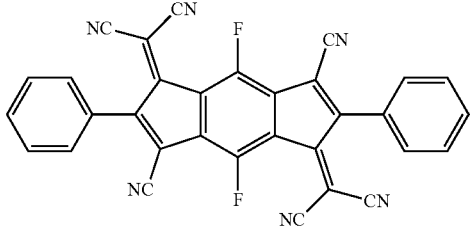
A41
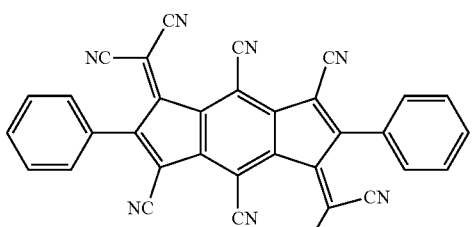
A42
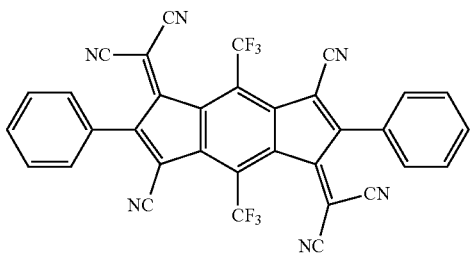
A43
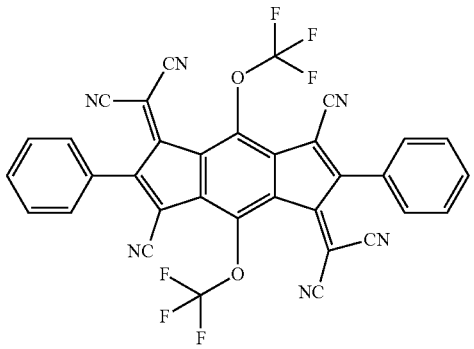
A44
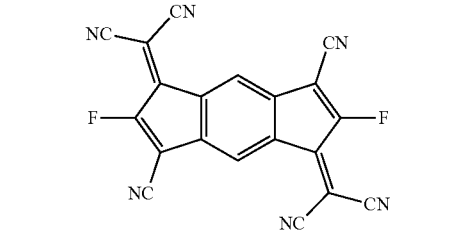
A45
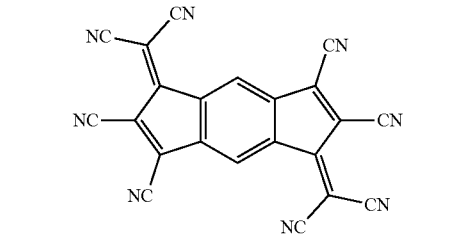

-continued
A46
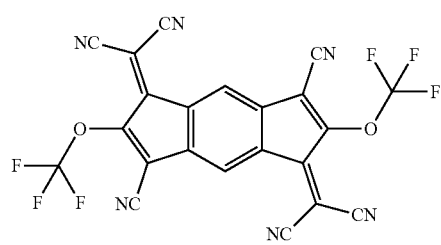
A47
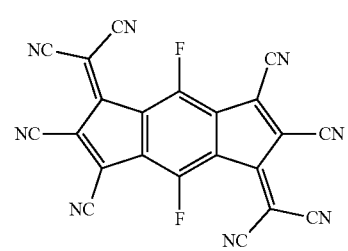
A48
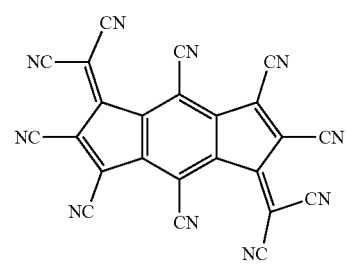
A49
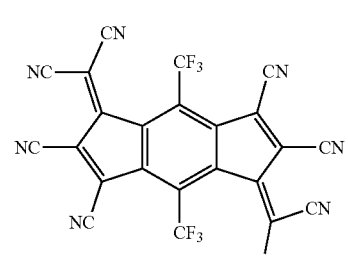
A50
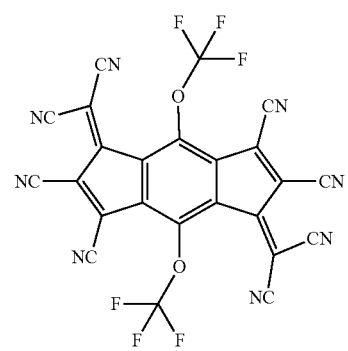
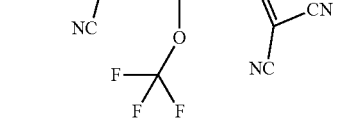
-continued
A51
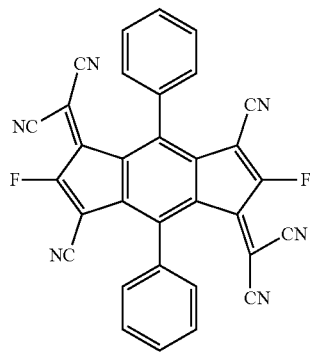
A52
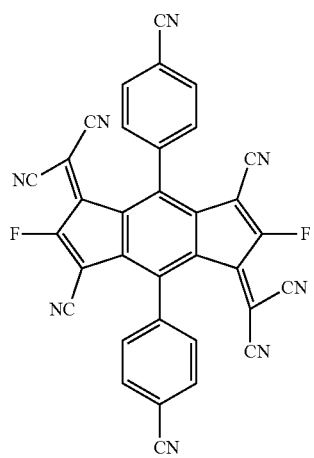
A53
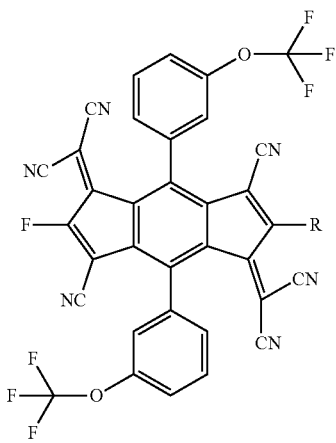
A54
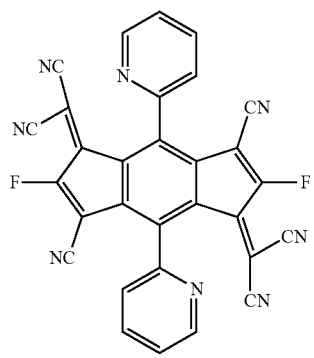

-continued
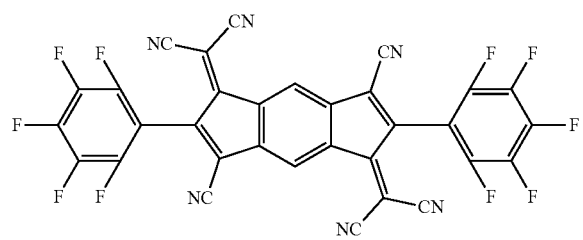
A55
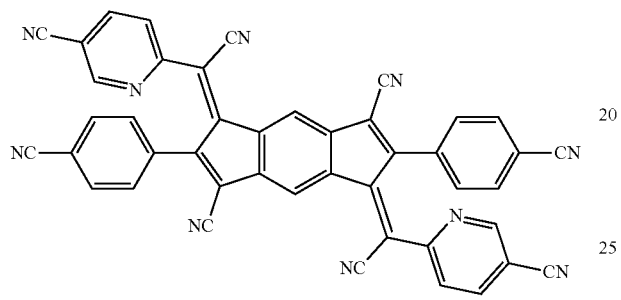
A56
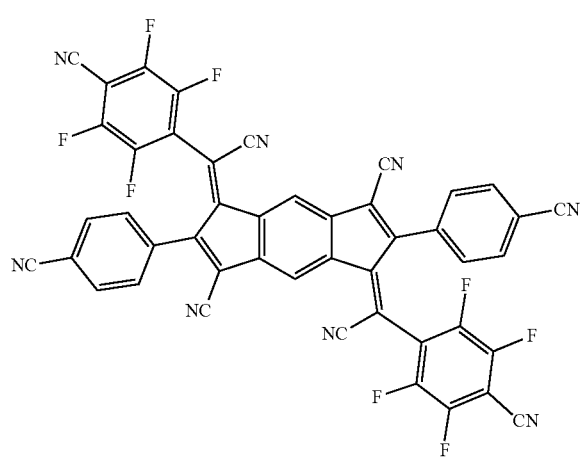
A57
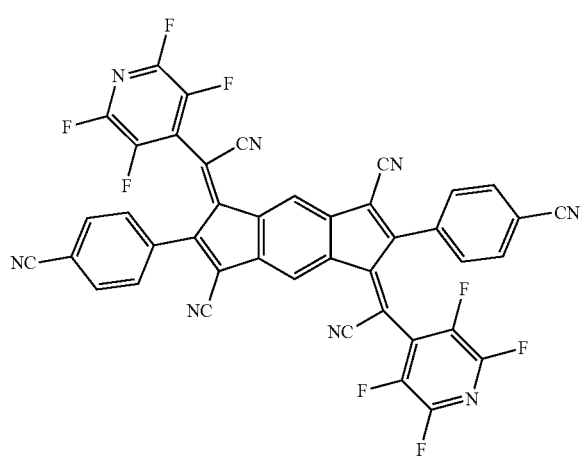
A58
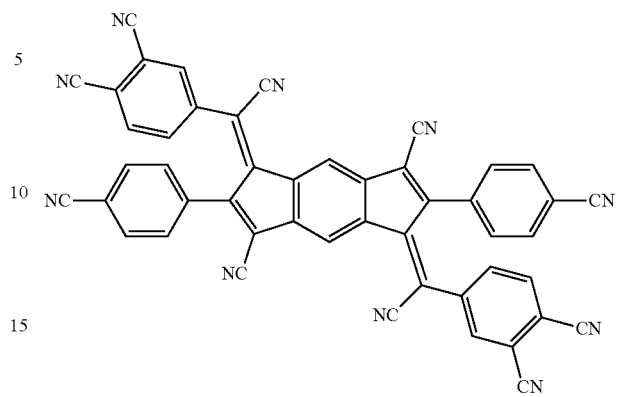
A59
A60
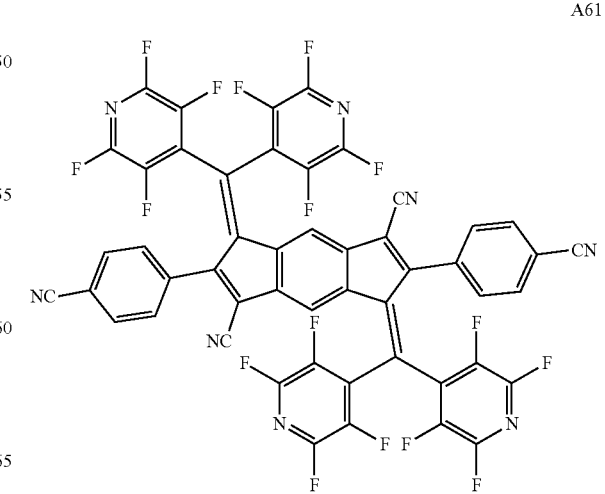
A61

A62
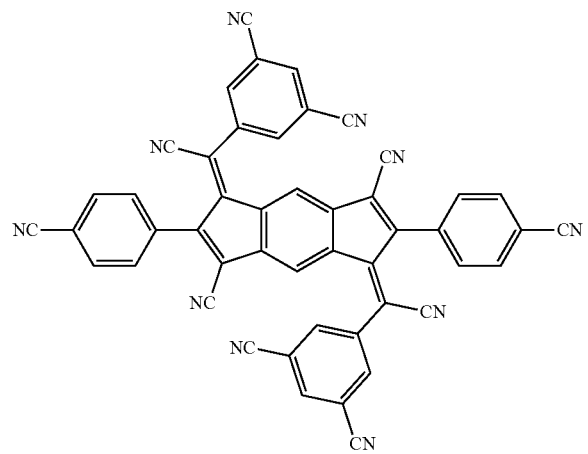
A63
B1
B2
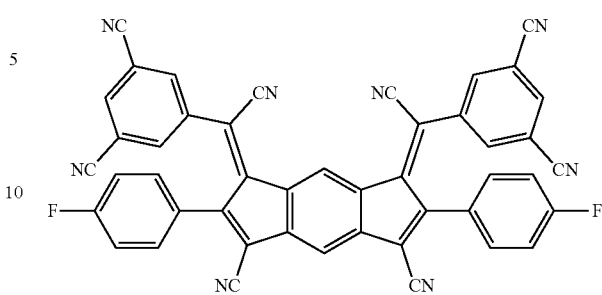
B3
B4
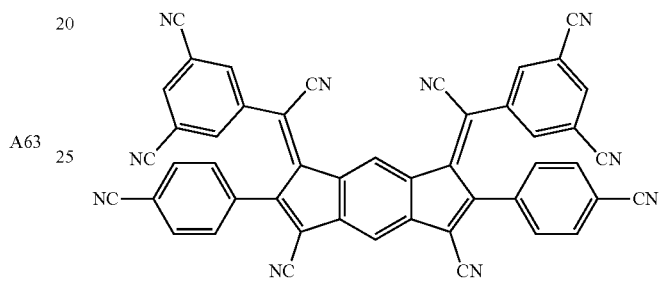
B5
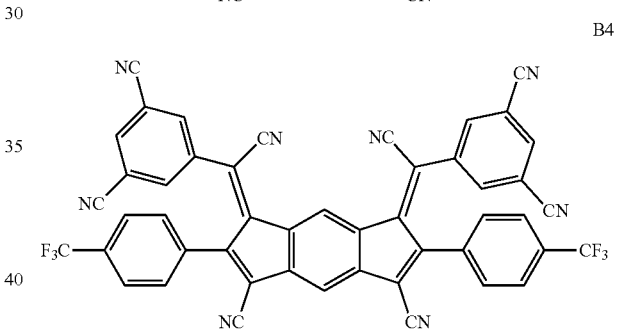
B6
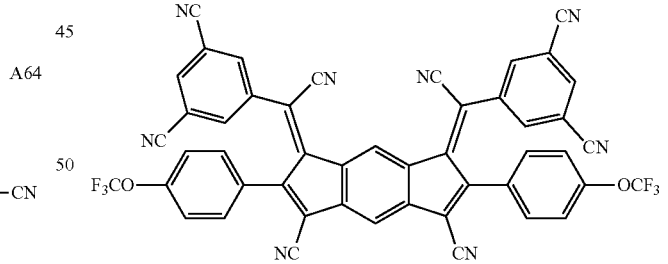
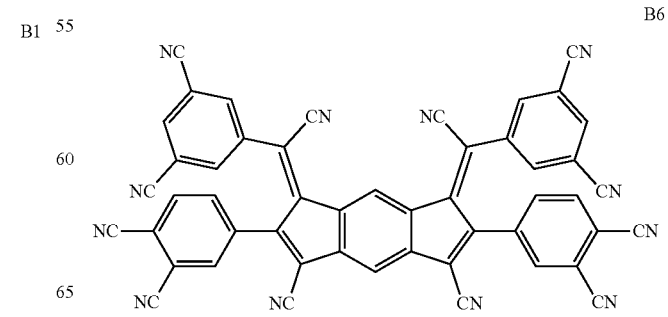

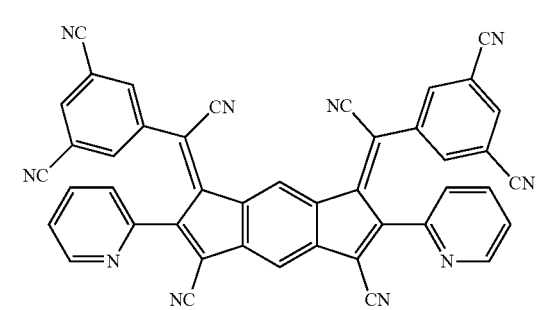
B7
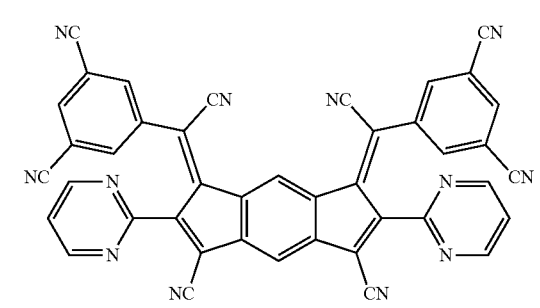
B8
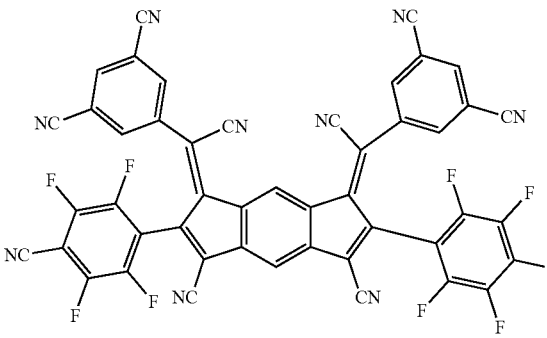
B9
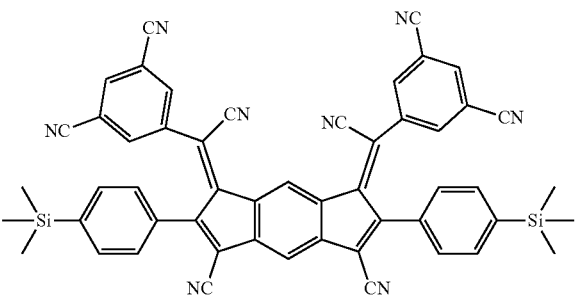
B10
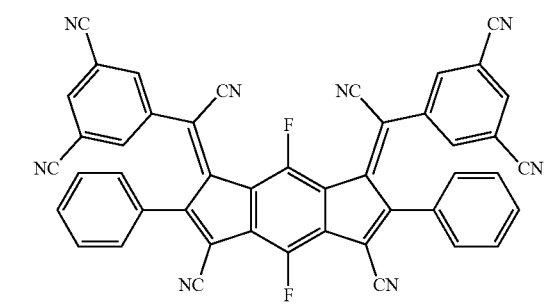
B11
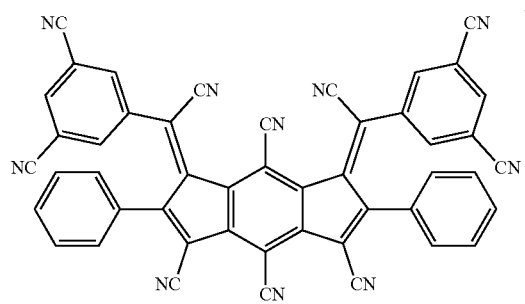
B12
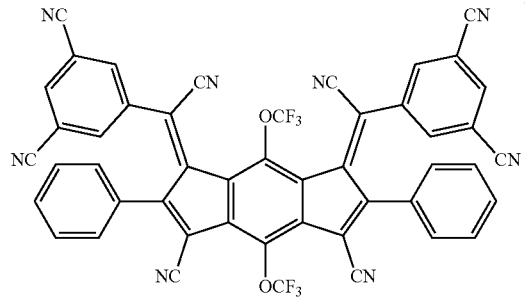
B13
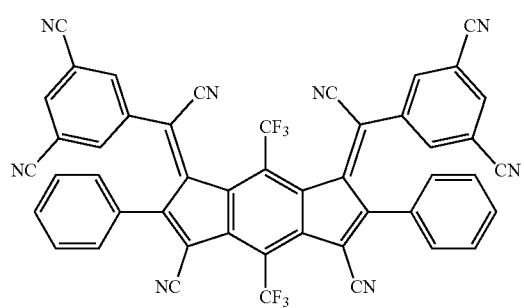
B14
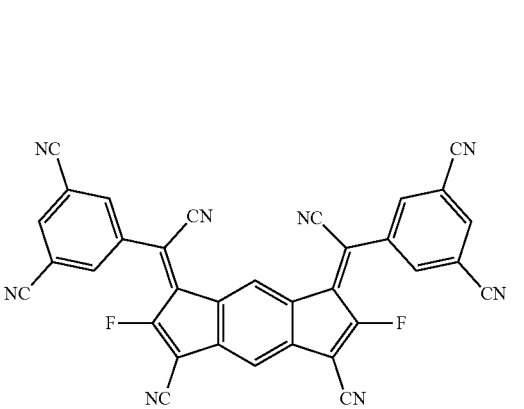
B15
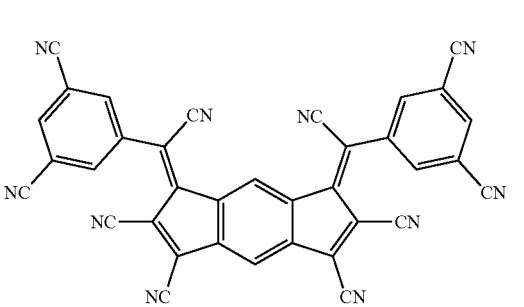
B16

-continued
B17
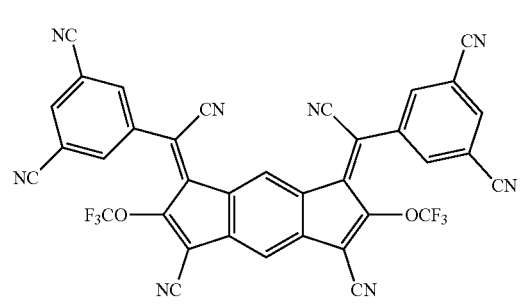
B18
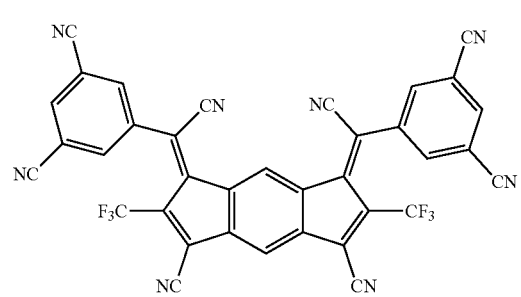
B19
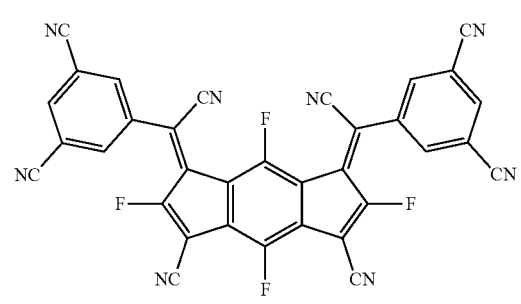
B20
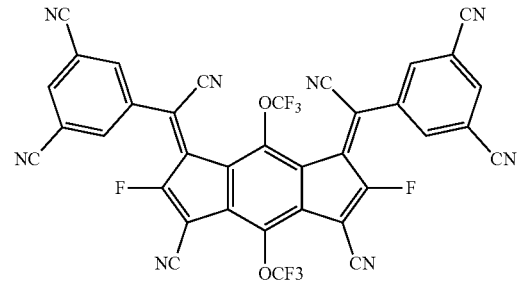
B21
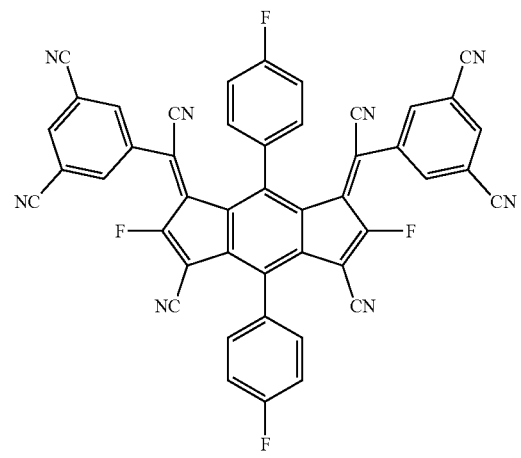
-continued
B22
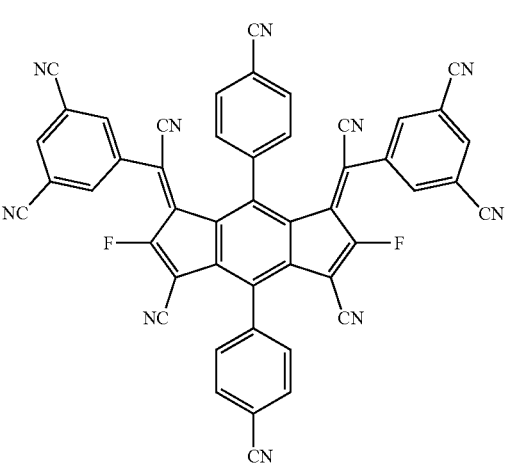
B23
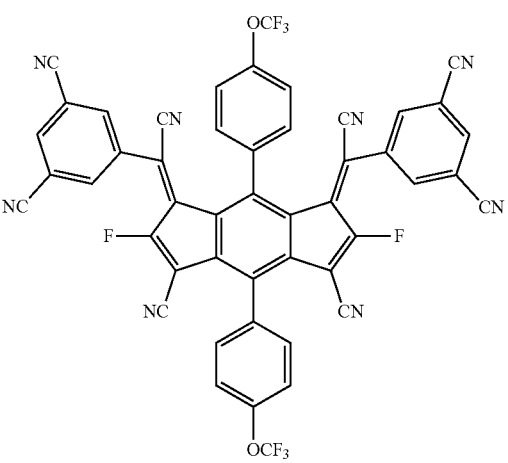
B24
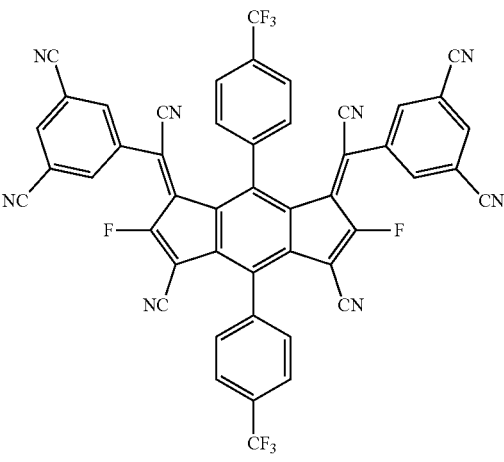

-continued
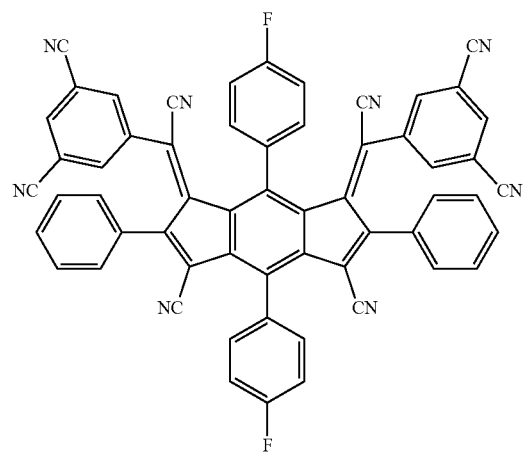
B25
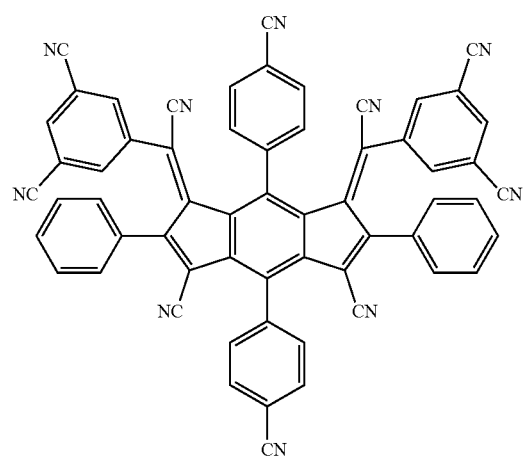
B26
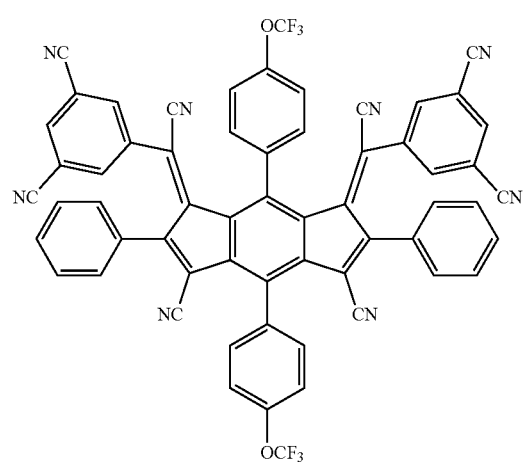
B27
-continued
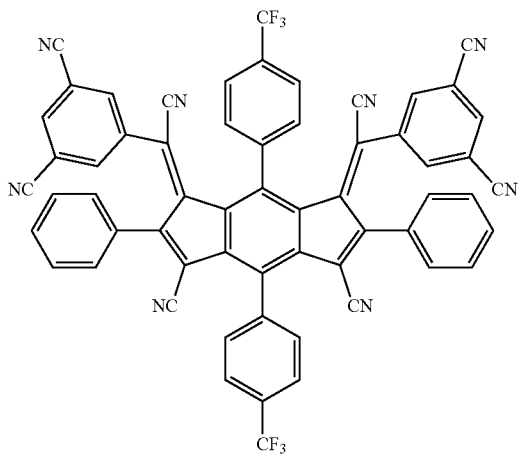
B28
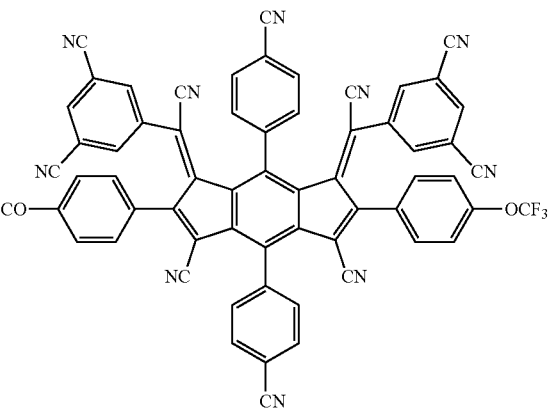
B29
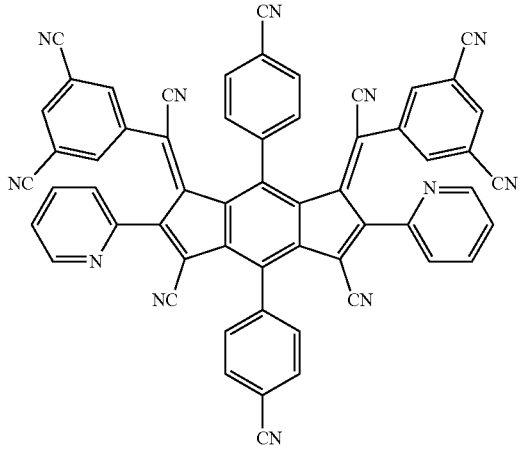
B30
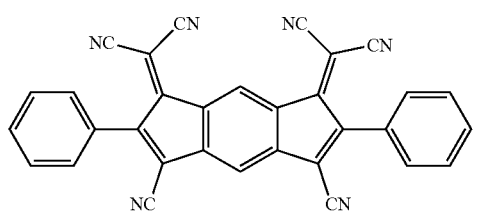
B31

-continued
B32
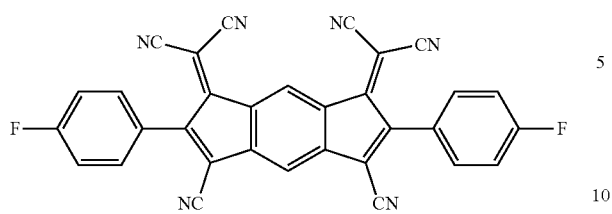
B33
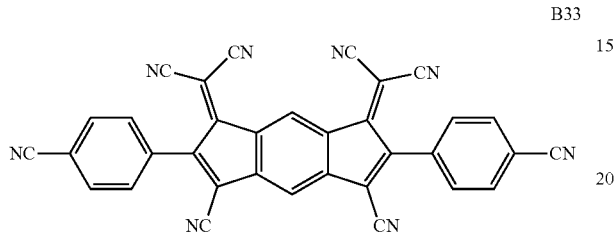
B34
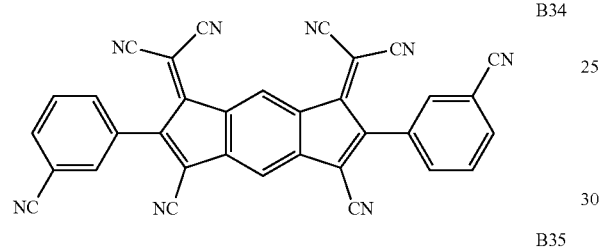
B35
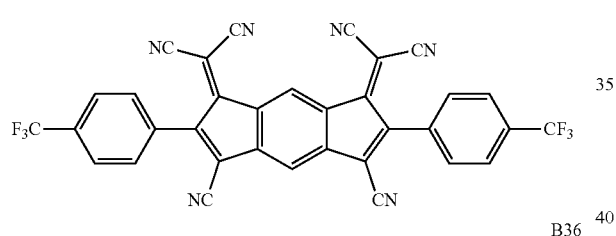
B36
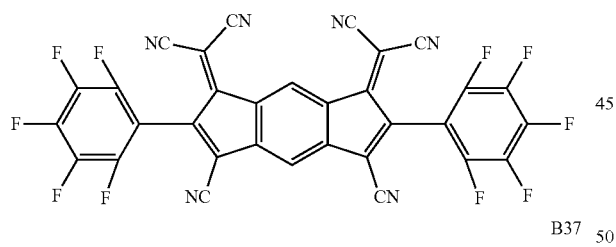
B37
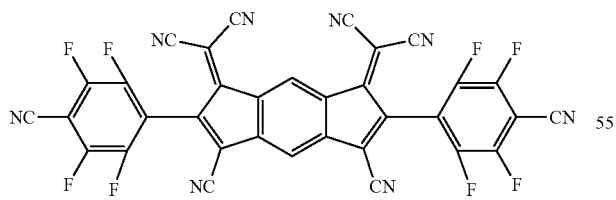
B38
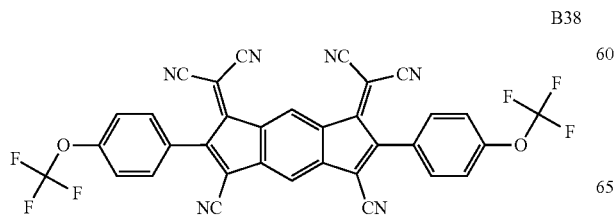
-continued
B39
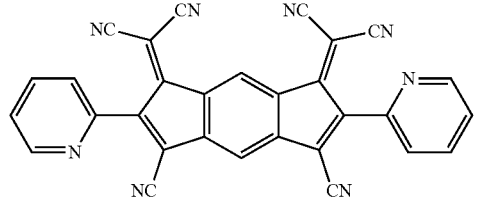
B40
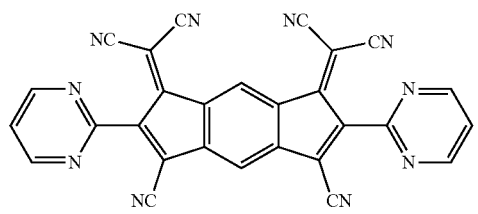
B41
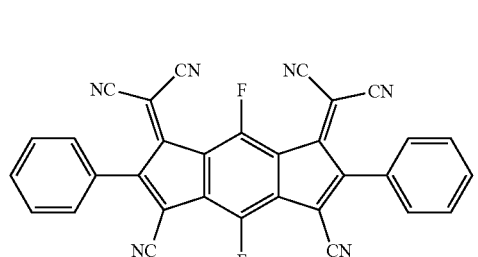
B42
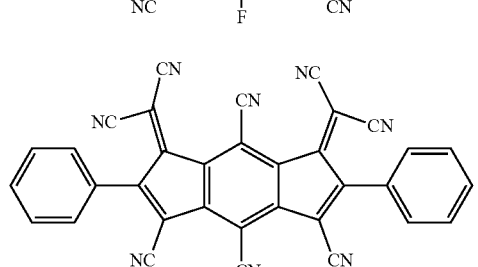
B43
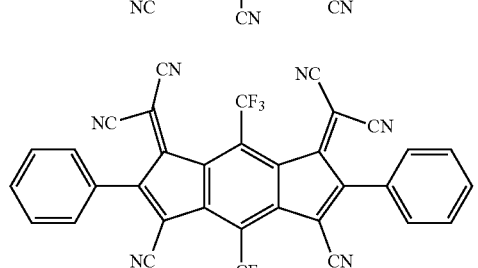
B44
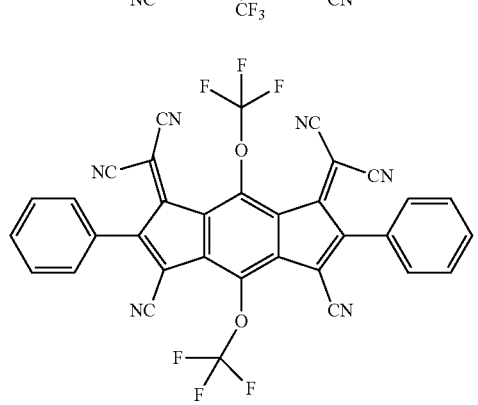

-continued
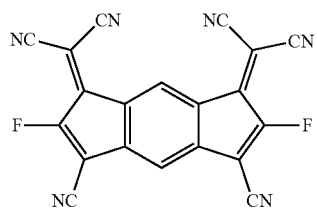
B45
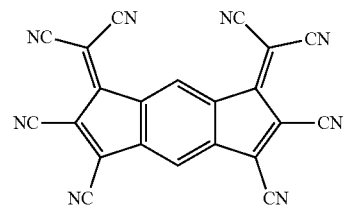
B46
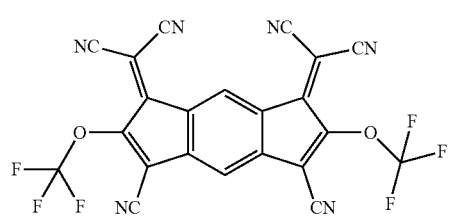
B47
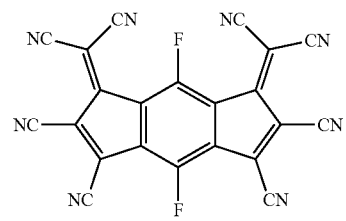
B48
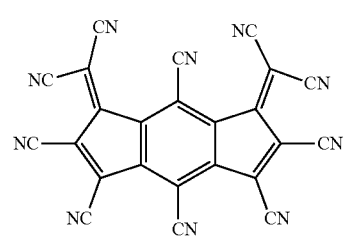
B49
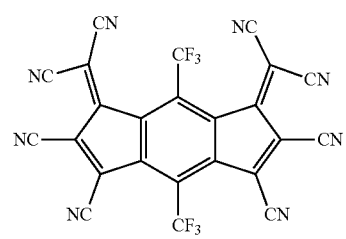
B50
-continued
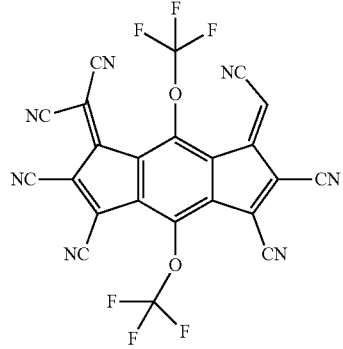
B51
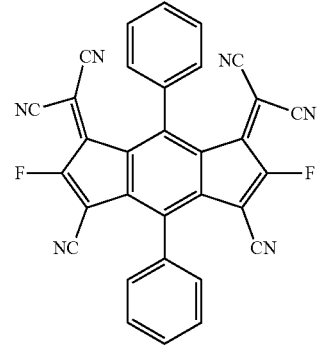
B52
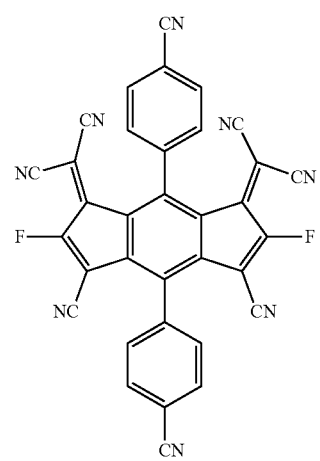
B53
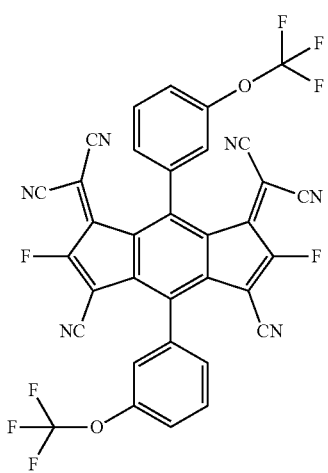
B54

-continued
B55
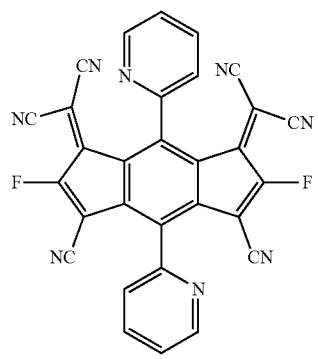
B56
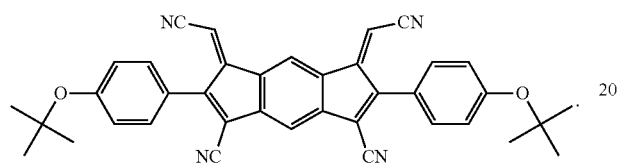
* * * * *